United States Patent
Zheng et al.

(10) Patent No.: US 9,951,024 B2
(45) Date of Patent: Apr. 24, 2018

(54) SMALL-MOLECULE INHIBITORS TARGETING G-PROTEIN-COUPLED RHO GUANINE NUCLEOTIDE EXCHANGE FACTORS

(71) Applicants: Children's Hospital Medical Center, Cincinnati, OH (US); University of Cincinnati, Cincinnati, OH (US)

(72) Inventors: Yi Zheng, Cincinnati, OH (US); Matthew Wortman, Ft Wright, KY (US)

(73) Assignees: Children's Hospital Medical Center, Cincinnati, OH (US); Univeristy of Cincinnati, Cincinnati, OH (US)

( * ) Notice: Subject to any disclaimer, the term of this patent is extended or adjusted under 35 U.S.C. 154(b) by 0 days.

(21) Appl. No.: 15/644,476

(22) Filed: Jul. 7, 2017

(65) Prior Publication Data

US 2017/0349553 A1    Dec. 7, 2017

Related U.S. Application Data

(62) Division of application No. 14/764,129, filed as application No. PCT/US2014/013444 on Jan. 28, 2014, now abandoned.

(60) Provisional application No. 61/758,174, filed on Jan. 29, 2013.

(51) Int. Cl.
| | | |
|---|---|---|
| C07D 231/36 | (2006.01) | |
| A61K 31/4152 | (2006.01) | |
| A61K 31/498 | (2006.01) | |
| C07D 403/06 | (2006.01) | |
| C12Q 1/34 | (2006.01) | |

(52) U.S. Cl.
CPC ........ *C07D 231/36* (2013.01); *A61K 31/4152* (2013.01); *A61K 31/498* (2013.01); *C07D 403/06* (2013.01); *C12Q 1/34* (2013.01); *G01N 2500/00* (2013.01)

(58) Field of Classification Search
None
See application file for complete search history.

(56) References Cited

U.S. PATENT DOCUMENTS

| | | |
|---|---|---|
| 2004/0176372 A1 | 9/2004 | Suto et al. |
| 2007/0203236 A1 | 8/2007 | Smith et al. |

FOREIGN PATENT DOCUMENTS

| | | |
|---|---|---|
| JP | 2010-018687 A | 1/2010 |
| WO | WO 03/074550 A2 | 9/2003 |

OTHER PUBLICATIONS

Deng et al., "Pyrazolidine-3,5-dione derivatives as potent non-steroidal agonists of farnesoid X receptor: Virtual screening, synthesis, and biological evaluation," *Bioorganic and Medical Chemistry Letter*, (2008), 18(20): 5497-5502.

Koo, K.A., et al., "QSAR analysis of pyrazolidine-3, 5-diones derivatives as Dyrk1A inhibitors," *Bioorganic & Medicinal Chemistry Letters*, (2009), 19(8): 2324-2328.

Nishikimi, A., et al., "Blockade of Inflammatory Responses by a Small-Molecule Inhibitor of the Rac Activator DOCK2," *Chemistry & Biology*, (2012), 19(4): 488-497.

International Search Report and Written Opinion dated May 30, 2014 received in PCT/US2014/013444.

*Primary Examiner* — Kamal Saeed
(74) *Attorney, Agent, or Firm* — Knobbe Martens Olson & Bear LLP

(57) ABSTRACT

Provided are inhibitors of Rho GTPase activation, and, in particular, compounds that inhibit RhoA activation by an RhoGEF. Also provided are related pharmaceutical compositions and methods. Also provided are methods of inhibiting Rho GTPase activation. Also provided are methods of screening for compounds that inhibit Rho GTPase activation by a RhoGEF.

19 Claims, 18 Drawing Sheets

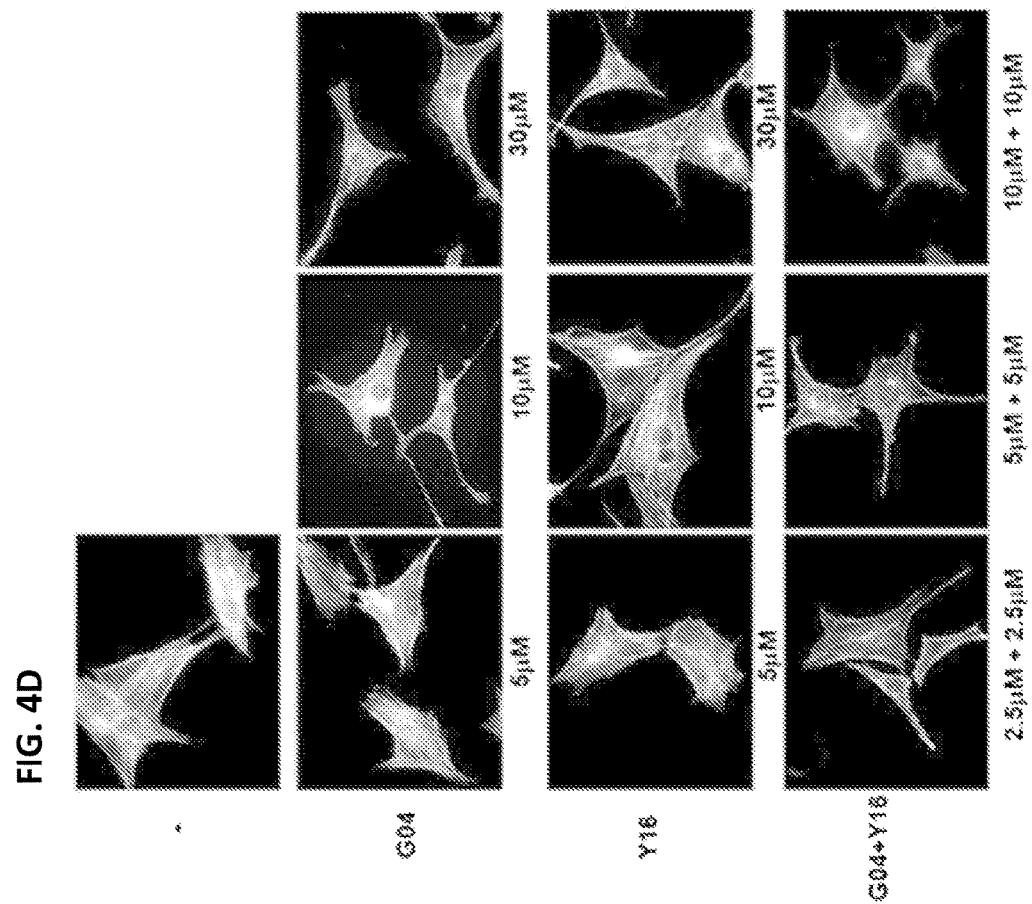

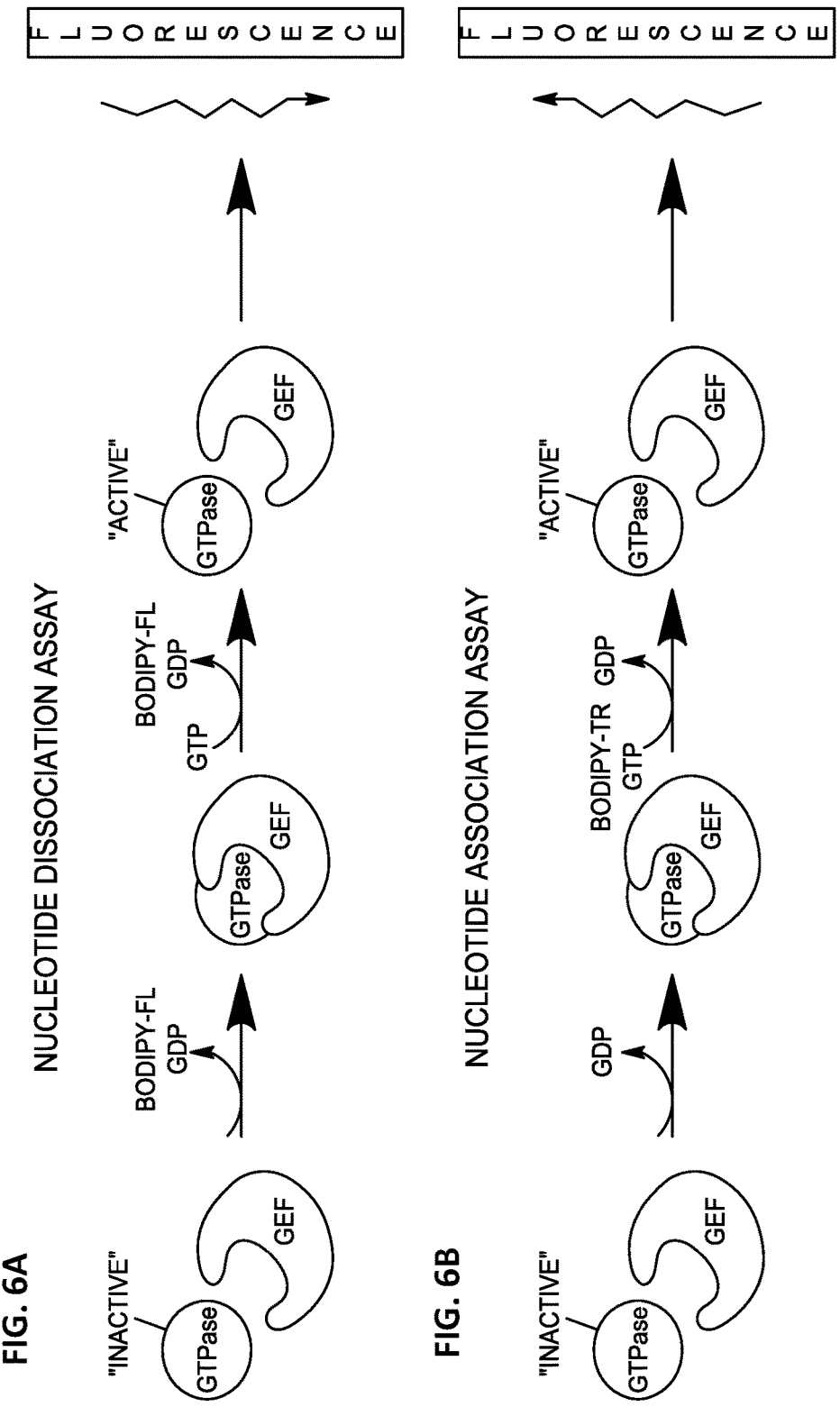

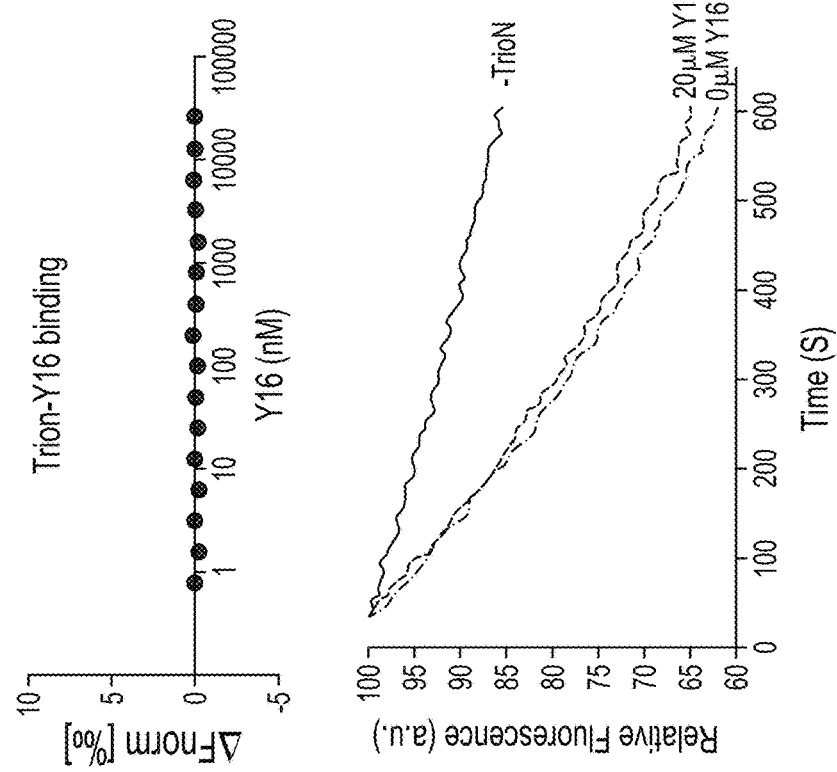
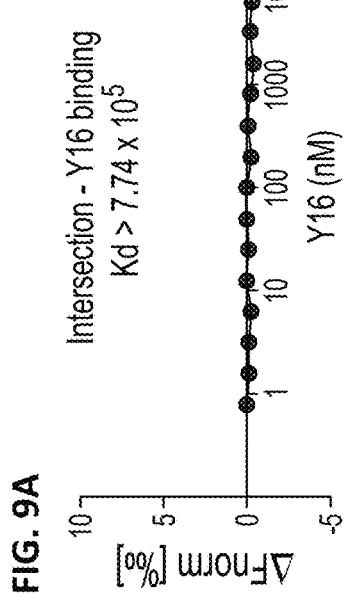
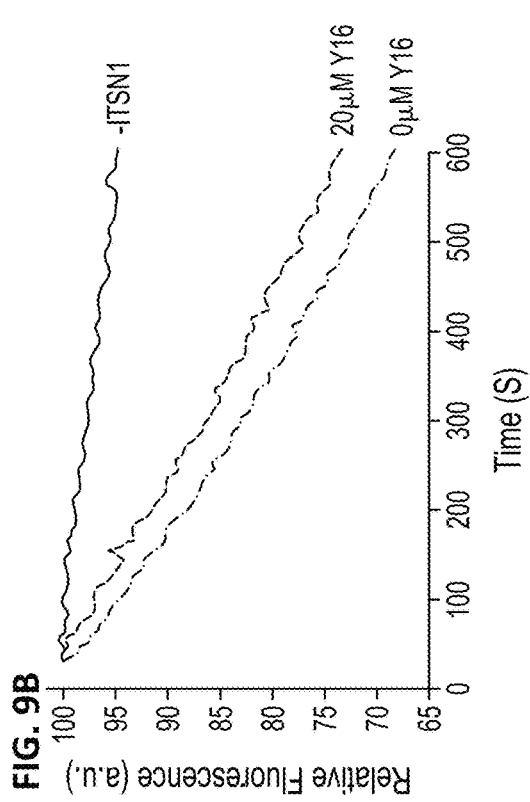
FIG. 9A
FIG. 9B

SMALL-MOLECULE INHIBITORS TARGETING G-PROTEIN-COUPLED RHO GUANINE NUCLEOTIDE EXCHANGE FACTORS

CROSS REFERENCE TO RELATED APPLICATIONS

Any and all priority claims identified in the Application Data Sheet, or any correction thereto, are hereby incorporated by reference under 37 CFR 1.57. For example, this application is a divisional of U.S. patent application Ser. No. 14/764,129, filed on Jul. 28, 2015, which is a U.S. National Phase of International Application No. PCT/US2014/013444, filed on Jan. 28, 2014 and published on Aug. 7, 2014 as WO 2014/120683, which claims the benefit of U.S. Provisional Application 61/758,174, filed on Jan. 29, 2013, which is incorporated herein by reference in its entirety.

STATEMENT REGARDING FEDERALLY SPONSORED R&D

This invention was made with government support under DK090971, CA150547 and CA141341, awarded by the National Institutes of Health. The government has certain rights in the invention.

BACKGROUND

Field

The present application is directed to inhibitors of Rho GTPase activation, and, in particular, compounds that inhibit RhoA activation by an RGS domain-containing RhoGEF.

Description of the Related Technology

Rho family GTPases are intracellular signaling molecules that regulate cytoskeleton organization, gene expression, cell cycle progression, cell motility, and other cellular processes (1-4). The activities of many Rho family members hinge upon a balance between the GTP-bound, active state and the GDP-bound, inactive state, which is subject to regulation in cells in response to physiologic and pathologic signals. Rho guanine nucleotide exchange factors (GEFs) represent the major class of activating enzymes of Rho GTPases by serving to relay a variety of signals to catalyze GDP/GTP exchange of specific Rho GTPases. To date, >80 RhoGEFs have been discovered that regulate the activities of over a dozen Rho GTPases in mammals (5). The overabundance of RhoGEFs vs. Rho GTPase substrates allows the GEFs to function in a tissue/cell type- and signaling pathway-specific manner, even though multiple RhoGEFs may possess the activating potential for a given Rho GTPase.

Consistent with a broad association of abnormal Rho GTPase activities in human cancers, a number of RhoGEFs have been reported to be overexpressed and/or hyperactivated in cancer cells, and they may be causal for tumor cell invasion and/or proliferation (6). The DH-PH domains shared among the DBL RhoGEF family, which constitutes the major class of RhoGEFs (7), have been characterized as the critical binding and catalytic motif required for Rho GTPase activation, and in-depth knowledge of the mechanism of DH-PH-mediated GEF reaction has been obtained in the last two decades (8-10). Among the DBL-like RhoGEFs, the heterotrimeric G-protein-regulated LARG, p115RhoGEF, and PDZRhoGEF form a unique RhoGEF subfamily that transduce signals from Gα12/13-coupled chemokine or mitogen receptors to RhoA through their RGS and DH-PH domains (11-15). The Gα12/13-RhoGEF-RhoA signaling cascade has been proposed as a useful target in cancer or neurologic diseases (16).

Small-molecule chemicals, as a major structural class of drugs, are broadly pursued in targeting oncoproteins and their signaling pathways. However, only proteins containing suitable hydrophobic pockets are considered druggable (17-20), which significantly limits the scope of drug discovery effort. In the Gα12/13-Rho-GEF-RhoA signaling cascade, the G proteins and Rho GTPases are considered difficult to target in part because they have globular structures with limited druggable surface areas.

SUMMARY

Some embodiments provide a compound having the structure of Formula I:

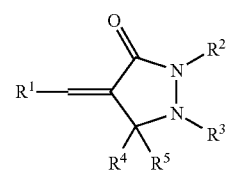

or a pharmaceutically acceptable salt thereof or tautomer thereof,
wherein:
$R^1$ is aryl, heteroaryl, or heterocyclyl, each optionally substituted with one or more $R^{1A}$ with the proviso that $R^1$ is not furanyl or furanyl substituted with optionally substituted aryl;
each $R^{1A}$ is independently selected from the group consisting of hydroxy, halo, cyano, nitro, —SO$_2$OH, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;
each $R^{1B}$ is independently selected from the group consisting of —OR$^{1C}$, C-carboxy, O-carboxy, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is H (hydrogen), aryl, or heteroaryl, said aryl or heteroaryl each optionally substituted with one or more $R^{2A}$;

each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);

each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^4$ is H (hydrogen), or $C_{1-6}$ alkyl; and $R^5$ is H (hydrogen), or $C_{1-6}$ alkyl, or optionally $R^4$ and $R^5$ together are oxo, with the proviso that the compound is not:

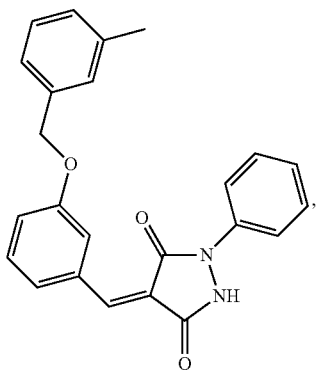 [SMILES: Cc1cccc(COc2cccc(/C=C3/C(=O)NN(c4ccccc4)C3=O)c2)c1]

4-(4-Iodo-benzylidene)-1-(4-iodo-phenyl)-pyrazolidine-3,5-dione,
4-(Dimethyl-furan-2-ylmethylene)-1-(3-trifluoromethyl-phenyl)-pyrazolidine-3,5-dione,
Acetic acid 5-[1-(4-iodo-phenyl)-3,5-dioxo-pyrazolidin-4-ylidenemethyl]-furan-2-ylmethyl ester,
4-(4-Bromo-furan-2-ylmethylene)-1-(4-iodo-phenyl)-pyrazolidine-3,5-dione,
1-(4-Iodo-phenyl)-4-(5-methyl-furan-2-ylmethylene)-pyrazolidine-3,5-dione,
4-(5-Bromo-furan-2-ylmethylene)-1-(4-iodo-phenyl)-pyrazolidine-3,5-dione,
1-(4-Iodo-phenyl)-4-[5-(2-methoxy-phenyl)-thiophen-2-ylmethylene]-pyrazolidine-3,5-dione,
1-(4-Iodo-phenyl)-4-thiophen-3-ylmethylene-pyrazolidine-3,5-dione,
1-(4-Iodo-phenyl)-4-(5-phenyl-thiophen-2-ylmethylene)-pyrazolidine-3,5-dione,
4-(5-Methyl-furan-2-ylmethylene)-1-(3-trifluoromethyl-phenyl)-pyrazolidine-3,5-dione,
4-Thiophen-2-ylmethylene-1-(3-trifluoromethyl-phenyl)-pyrazolidine-3,5-dione,
4-(4-Bromo-furan-2-ylmethylene)-1-(3-trifluoromethyl-phenyl)-pyrazolidine-3, 5-dione,
Acetic acid 5-[3,5-dioxo-1-(3-trifluoromethyl-phenyl)-pyrazolidin-4-ylidenemethyl]-furan-2-ylmethyl ester,
4-(7-Bromo-8-hydroxy-quinolin-5-ylmethylene)-1-(4-iodo-phenyl)-pyrazolidine-3,5-dione,
1-(4-Iodo-phenyl)-4-[5-(4-nitro-phenyl)-furan-2-ylmethylene]-pyrazolidine-3,5-dione,
1-(4-Iodo-phenyl)-4-[5-(2-nitro-phenyl)-furan-2-ylmethylene]-pyrazolidine-3, 5-dione,
4-(5-Hydroxymethyl-furan-2-ylmethylene)-1-(4-iodo-phenyl)-pyrazolidine-3,5-dione,
1-(4-Iodo-phenyl)-4-(5-nitro-thiophen-2-ylmethylene)-pyrazolidine-3,5-dione,
4-(5-Hydroxymethyl-furan-2-ylmethylene)-1-(3-trifluoromethyl-phenyl)-pyrazolidine-3,5-dione,
4-(5-Nitro-thiophen-2-ylmethylene)-1-(3-trifluoromethyl-phenyl)-pyrazolidine-3,5-dione,
1-(4-Iodo-phenyl)-4-(5-nitro-furan-2-ylmethylene)-pyrazolidine-3,5-dione,
4-(4, 5-Dimethyl-furan-2-ylmethylene)-1-(4-iodo-phenyl)-pyrazolidine-3,5-dione,
5-[1-(4-Iodo-phenyl)-3,5-dioxo-pyrazolidin-4-ylidenemethyl]-furan-2-sulfonic acid,
4-[1-(4-Iodo-phenyl)-3,5-dioxo-pyrazolidin-4-ylidenemethyl]-benzonitrile,
1-(4-Iodo-phenyl)-4-(3-methyl-thiophen-2-ylmethylene)-pyrazolidine-3,5-dione,
4-(4-Bromo-thiophen-2-ylmethylene)-1-(4-iodo-phenyl)-pyrazolidine-3,5-dione,
1-(4-Iodo-phenyl)-4-(5-methyl-thiophen-2-ylmethylene)-pyrazolidine-3,5-dione,
4-Benzo[b]thiophen-2-ylmethylene-1-(4-iodo-phenyl)-pyrazolidine-3,5-dione,
1-(4-Iodo-phenyl)-4-(4-nitro-thiophen-2-ylmethylene)-pyrazolidine-3,5-dione,
5-[1-(4-Iodo-phenyl)-3,5-dioxo-pyrazolidin-4-ylidenemethyl]-thiophene-3-carboxylic acid,
4-[1-(4-Iodo-phenyl)-3,5-dioxo-pyrazolidin-4-ylidenemethyl]-thiophene-3-carboxylic acid,
2-[3,5-Dioxo-1-(3-trifluoromethyl-phenyl)-pyrazolidin-4-ylidenemethyl]-thiophene-3-carboxylic acid,
4-(4-Nitro-thiophen-2-ylmethylene)-1-(3-trifluoromethyl-phenyl)-pyrazolidine-3,5-dione,
4-[3,5-Dioxo-1-(3-trifluoromethyl-phenyl)-pyrazolidin-4-ylidenemethyl]-thiophene-3-carboxylic acid,
{3-[3,5-Dioxo-1-(3-trifluoromethyl-phenyl)-pyrazolidin-4-ylidenemethyl]-thiophen-2-ylsulfanyl-acetic acid,
2-[1-(4-Iodo-phenyl)-3,5-dioxo-pyrazolidin-4-ylidenemethyl]-thiophene-3-carboxylic acid,
4-(4-Hydroxymethyl-furan-3-ylmethylene)-1-(3-trifluoromethyl-phenyl)-pyrazolidine-3,5-dione,
4-benzo[b]thiophen-2-ylmethylene-1-(3-trifluoromethyl-phenyl)-pyrazolidine-3,5-dione,
5-[3,5-Dioxo-1-(3-trifluoromethyl-phenyl)-pyrazolidin-4-ylidenemethyl]-thiophene-3-carboxylic acid,
5-[1-(4-Iodo-phenyl)-3,5-dioxo-pyrazolidin-4-ylidenemethyl]-furan-2-carboxylic acid,
5-(1-Biphenyl-4-yl-3,5-dioxo-pyrazolidin-4-ylidenemethyl]-furan-2-carboxylic acid,
4-(4-Hydroxy-naphthalen-1-ylmethylene)-1-(4-iodo-phenyl)-pyrazolidine-3,5-dione, 1-(4-Iodo-phenyl)-4-(1-oxy-pyridin-4-ylmethylene)-pyrazolidine-3,5-dione, 4-(1H-Indol-5-ylmethylene)-1-(4-iodo-phenyl)-pyrazolidine-3,5-dione, 4-(4-Hydroxymethyl-furan-3-ylmethylene)-1-(4-iodo-phenyl)-pyrazolidine-3, 5-dione, 1-(4-Iodophenyl)-4-(1H-pyrrol-2-ylmethylene)-pyrazolidine-3,5-dione, 1-(4-Iodophenyl)-4-(1-methyl-1H-pyrrol-2-ylmethylene)-pyrazolidine-3,5-dione, 1-(4-Iodo-phenyl)-4-[1-(2-nitro-benzyl)-1H-pyrrol-2-ylmethylene]-pyrazolidine-3,5-dione, 1-(4-Iodo-phenyl-4-(1H-pyrazol-3-ylmethylene)-pyrazolidine-3,5-dione, 1-(4-Iodo-phenyl-4-(1H-pyrazol-3-ylmethylene)-pyrazolidine-3,5-dione, 4-(2,3-Dihydro-benzofuran-5-ylmethylene)-1-(4-iodo-phenyl)-pyrazolidine-3,5-dione, 1-(4-Iodo-phenyl)-4-quinolin-2-ylmethylene-pyrazolidine-3,5-dione, 1-(4-Iodo-phenyl)-4-quinolin-4-ylmethylene-pyrazolidine-3,5-dione, 4-[3-(2-Hydroxy-ethoxy)-benzylidene]-1-(4-iodo-phenyl)-pyrazolidine-3,5-dione, 1-(4-Iodo-phenyl)-4-(5-naphthalen-2-yl-thiophen-2-ylmethylene)-pyrazolidine-3,5-dione, 3-{5-[1-(4-Iodo-phenyl)-3,5-dioxo-pyrazolidin-4-ylidenemethyl]-furan-2-yl}-thiophene-2-carboxylic acid methyl ester, 4-(5-Chloro-thiophen-2-ylmethylene)-1-(4-iodo-phenyl)-pyrazolidine-3,5-dione,

[1-(4-Iodo-phenyl)-4-thiazol-2-ylmethylene-pyrazolidine-3,5-dione, 1-(4-Iodo-phenyl)-4-(1-methyl-1H-imidazol-2-ylmethylene)-pyrazolidine-3,5-dione, 4-(2-Diethylamino-thiazol-5-ylmethylene)-1-(4-iodo-phenyl)-pyrazolidine-3,5-dione, 4-[2-(4-Benzyl-piperazin-1-yl)-thiazol-5-ylmethylene]-1-(4-iodo-phenyl)-pyrazolidine-3,5-dione, 1-(4-Iodo-phenyl)-4-[2-(4-methoxy-phenoxy)-thiazol-5-ylmethylene]-pyrazolidine-3,5-dione, 4-(9-Ethyl-9H-carbazol-3-ylmethylene)-1-(4-iodo-phenyl)-pyrazolidine-3, 5-dione, or 4-Benzo[b]thiophen-3-ylmethylene-1-(4-iodo-phenyl)-pyrazolidine-3,5-dione, or a pharmaceutically acceptable salt thereof or tautomer thereof.

Some embodiments provide a composition comprising a pharmaceutically acceptable excipient, and a compound as disclosed and described herein, or a pharmaceutically acceptable salt thereof or tautomer thereof.

Some embodiments provide a method of evaluating the inhibition of Rho GTPase activation comprising contacting a RhoGEF with a compound as disclosed and described herein, or a pharmaceutically acceptable salt thereof or tautomer thereof. In some embodiments, the RhoGEF is RGS domain-containing RhoGEF.

Some embodiments provide a unit dosage of a pharmaceutical composition for treating breast cancer, leukemia, or lung cancer comprising a pharmaceutically acceptable excipient, and a therapeutically effective amount of a compound having the structure of Formula I:

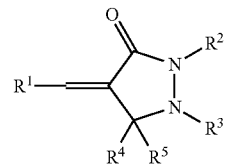

or a pharmaceutically acceptable salt thereof or tautomer thereof, wherein:

$R^1$ is aryl, heteroaryl, or heterocyclyl, each optionally substituted with one or more $R^{1A}$;

each $R^{1A}$ is independently selected from the group consisting of hydroxy, halo, cyano, nitro, —SO$_2$OH, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;

each $R^{1B}$ is independently selected from the group consisting of —$OR^{1C}$, aryl, and heteroaryl, said aryl or heteroaryl each optionally substituted with one or more $R^{1D}$;

each $R^{1C}$ is independently selected from the group consisting of aryl, and heteroaryl, said aryl or heteroaryl each optionally substituted with one or more $R^{1E}$;

each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is H (hydrogen), aryl, or heteroaryl, said aryl or heteroaryl each optionally substituted with one or more $R^{2A}$;

each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);

each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
$R^4$ is H (hydrogen), or $C_{1-6}$ alkyl; and
$R^5$ is H (hydrogen), or $C_{1-6}$ alkyl, or optionally $R^4$ and $R^5$ together are oxo.

Some embodiments provide a method of treating breast cancer, leukemia, or lung cancer comprising administering a therapeutically effective amount of a compounds as disclosed and described herein to a patient in need thereof.

Some embodiments provide a method of treating breast cancer, leukemia, or lung cancer comprising administering a therapeutically effective amount of the unit dosage as disclosed and described herein to a patient in need thereof.

Some embodiments provide a method of evaluating a compound for inhibition of Rho GTPase activation comprising contacting a RGS domain-containing RhoGEF with a compound having the structure of Formula I:

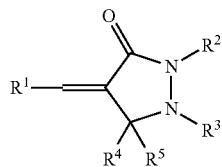

I or a pharmaceutically acceptable salt thereof, or tautomer thereof,
wherein:
$R^1$ is aryl, heteroaryl, or heterocyclyl, each optionally substituted with one or more $R^{1A}$;
each $R^{1A}$ is independently selected from the group consisting of hydroxy, halo, cyano, nitro, —SO$_2$OH, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;
each $R^{1B}$ is independently selected from the group consisting of —OR$^{1C}$, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
$R^2$ is H (hydrogen), aryl, or heteroaryl, said aryl or heteroaryl each optionally substituted with one or more $R^{2A}$;
each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);
each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
$R^4$ is H (hydrogen), or $C_{1-6}$ alkyl; and
$R^5$ is H (hydrogen), or $C_{1-6}$ alkyl, or optionally $R^4$ and $R^5$ together are oxo.

Some embodiments provide a method of inhibiting Rho GTPase activation comprising contacting a RGS domain-containing RhoGEF with a compound having the structure of Formula I:

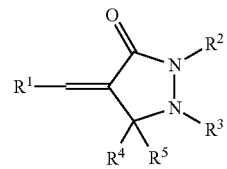

I or a pharmaceutically acceptable salt thereof,
wherein:
$R^1$ is aryl, heteroaryl, or heterocyclyl, each optionally substituted with one or more $R^{1A}$;
each $R^{1A}$ is independently selected from the group consisting of hydroxy, halo, cyano, nitro, —SO$_2$OH, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;
each $R^{1B}$ is independently selected from the group consisting of —OR$^{1C}$, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is H (hydrogen), aryl, or heteroaryl, said aryl or heteroaryl each optionally substituted with one or more $R^{2A}$;

each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);

each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^4$ is H (hydrogen), or $C_{1-6}$ alkyl; and $R^5$ is H (hydrogen), or $C_{1-6}$ alkyl, or optionally $R^4$ and $R^5$ together are oxo.

Some embodiments provide method of inhibiting Rho GTPase activation comprising contacting a RGS domain-containing RhoGEF with:

4-(4-Iodo-benzylidene)-1-(4-iodo-phenyl)-pyrazolidine-3, 5-dione, 4-(Dimethyl-furan-2-ylmethylene)-1-(3-trifluoromethyl-phenyl)-pyrazolidine-3,5-dione, 1-Biphenyl-4-yl-4-furan-2-ylmethylene-pyrazolidine-3,5-dione, Acetic acid 5-[1-(4-iodo-phenyl)-3,5-dioxo-pyrazolidin-4-ylidenemethyl]-furan-2-ylmethyl ester, 4-(4-Bromo-furan-2-ylmethylene)-1-(4-iodo-phenyl)-pyrazolidine-3,5-dione, 1-(4-Iodo-phenyl)-4-(5-methyl-furan-2-ylmethylene)-pyrazolidine-3,5-dione, 4-(5-Bromo-furan-2-ylmethylene)-1-(4-iodo-phenyl)-pyrazolidine-3,5-dione, 1-(4-Iodo-phenyl)-4-[5-(2-methoxy-phenyl)-thiophen-2-ylmethylene]-pyrazolidine-3,5-dione, 1-(4-Iodo-phenyl)-4-thiophen-3-ylmethylene-pyrazolidine-3,5-dione, 1-(4-Iodo-phenyl)-4-(5-phenyl-thiophen-2-ylmethylene)-pyrazolidine-3,5-dione, 4-Furan-2-ylmethylene-1-(3-trifluoromethyl-phenyl)-pyrazolidine-3,5-dione, 4-(5-Methyl-furan-2-ylmethylene)-1-(3-trifluoromethyl-phenyl)-pyrazolidine-3,5-dione, 4-Thiophen-2-ylmethylene-1-(3-trifluoromethyl-phenyl)-pyrazolidine-3,5-dione, 4-(4-Bromo-furan-2-ylmethylene)-1-(3-trifluoromethyl-phenyl)-pyrazolidine-3,5-dione, Acetic acid 5-[3,5-dioxo-1-(3-trifluoromethyl-phenyl)-pyrazolidin-4-ylidenemethyl]-furan-2-ylmethyl ester, 1-(3-Chloro-4-methyl-phenyl)-4-furan-2-ylmethylene-pyrazolidine-3,5-dione, 4-(7-Bromo-8-hydroxy-quinolin-5-ylmethylene)-1-(4-iodo-phenyl)-pyrazolidine-3, 5-dione, 1-(4-Iodo-phenyl)-4-[5-(4-nitro-phenyl)-furan-2-ylmethylene]-pyrazolidine-3,5-dione, 1-(4-Iodo-phenyl)-4-[5-(2-nitro-phenyl)-furan-2-ylmethylene]-pyrazolidine-3,5-dione, 4-(5-Hydroxymethyl-furan-2-ylmethylene)-1-(4-iodo-phenyl)-pyrazolidine-3,5-dione, 4-Furan-3-ylmethylene-1-(4-iodo-phenyl)-pyrazolidine-3, 5-dione, 1-(4-Iodo-phenyl)-4-(5-nitro-thiophen-2-ylmethylene)-pyrazolidine-3,5-dione, 4-(5-Hydroxymethyl-furan-2-ylmethylene)-1-(3-trifluoromethyl-phenyl)-pyrazolidine-3,5-dione, 4-Furan-3-ylmethylene-1-(3-trifluoromethyl-phenyl)-pyrazolidine-3,5-dione, 4-(5-Nitro-thiophen-2-ylmethylene)-1-(3-trifluoromethyl-phenyl)-pyrazolidine-3,5-dione, 1-(4-Iodo-phenyl)-4-(5-nitro-furan-2-ylmethylene)-pyrazolidine-3,5-dione, 1-(4-Iodo-phenyl)-4-[5-(3-nitro-phenyl)-furan-2-ylmethylene]-pyrazolidine-3,5-dione, 4-(4,5-Dimethyl-furan-2-ylmethylene)-1-(4-iodo-phenyl)-pyrazolidine-3,5-dione, 5-[1-(4-Iodo-phenyl)-3,5-dioxo-pyrazolidin-4-ylidenemethyl]-furan-2-sulfonic acid, 4-[1-(4-Iodo-phenyl)-3,5-dioxo-pyrazolidin-4-ylidenemethyl]-benzonitrile, 1-(4-Iodo-phenyl)-4-(3-methyl-thiophen-2-ylmethylene)-pyrazolidine-3,5-dione, 4-(4-Bromo-thiophen-2-ylmethylene)-1-(4-iodo-phenyl)-pyrazolidine-3,5-dione, 1-(4-Iodo-phenyl)-4-(5-methyl-thiophen-2-ylmethylene)-pyrazolidine-3,5-dione, 4-Benzo[b]thiophen-2-ylmethylene-1-(4-iodo-phenyl)-pyrazolidine-3,5-dione, 1-(4-Iodo-phenyl)-4-(4-nitro-thiophen-2-ylmethylene)-pyrazolidine-3,5-dione, 5-[1-(4-Iodo-phenyl)-3,5-dioxo-pyrazolidin-4-ylidenemethyl]-thiophene-3-carboxylic acid, 4-[1-(4-Iodo-phenyl)-3,5-dioxo-pyrazolidin-4-ylidenemethyl]-thiophene-3-carboxylic acid, 2-[3,5-Dioxo-1-(3-trifluoromethyl-phenyl)-pyrazolidin-4-ylidenemethyl]-thiophene-3-carboxylic acid, 4-(4-Nitro-thiophen-2-ylmethylene)-1-(3-trifluoromethyl-phenyl)-pyrazolidine-3,5-dione, 4-[3,5-Dioxo-1-(3-trifluoromethyl-phenyl)-pyrazolidin-4-ylidenemethyl]-thiophene-3-carboxylic acid, 2-[1-(4-Iodo-phenyl)-3,5-dioxo-pyrazolidin-4-ylidenemethyl]-thiophene-3-carboxylic acid, {3-[1-(4-Iodo-phenyl)-3,5-dioxo-pyrazolidin-4-ylidenemethyl]-thiophen-2-ylsulfanyl}-acetic acid, 4-(4-Hydroxymethyl-furan-3-ylmethylene)-1-(3-trifluoromethyl-phenyl)-pyrazolidine-3,5-dione, 4-benzo[b]thiophen-2-ylmethylene-1-(3-trifluoromethyl-phenyl)-pyrazolidine-3,5-dione, 5-[3,5-Dioxo-1-(3-trifluoromethyl-phenyl)-pyrazolidin-4-ylidenemethyl]-thiophene-3-carboxylic acid, 5-[1-(4-Iodo-phenyl)-3,5-dioxo-pyrazolidin-4-ylidenemethyl]-furan-2-carboxylic acid, 5-(1-Biphenyl-4-yl-3,5-dioxo-pyrazolidin-4-ylidenemethyl)-furan-2-carboxylic acid, 4-(4-Hydroxy-naphthalen-1-ylmethylene)-1-(4-iodo-phenyl)-pyrazolidine-3,5-dione,
1-(4-Iodo-phenyl)-4-(1-oxy-pyridin-4-ylmethylene)-pyrazolidine-3,5-dione,
2-(4-Furan-2-ylmethylene-3,5-dioxo-pyrazolidin-1-yl)-5-iodo-benzoic acid methyl ester,
4-(1H-Indol-5-ylmethylene)-1-(4-iodo-phenyl)-pyrazolidine-3,5-dione,
4-(4-Hydroxymethyl-furan-3-ylmethylene)-1-(4-iodo-phenyl)-pyrazolidine-3,5-dione,
1-(4-Iodophenyl)-4-(1H-pyrrol-2-ylmethylene)-pyrazolidine-3,5-dione,
1-(4-Iodophenyl)-4-(1-methyl-1H-pyrrol-2-ylmethylene)-pyrazolidine-3,5-dione,
1-(4-Iodo-phenyl)-4-[1-(2-nitro-benzyl)-1H-pyrrol-2-ylmethylene]-pyrazolidine-3,5-dione,
1-(4-Iodo-phenyl-4-(1H-pyrazol-3-ylmethylene)-pyrazolidine-3,5-dione,
1-(4-Iodo-phenyl-4-(1H-pyrazol-3-ylmethylene)-pyrazolidine-3,5-dione,
4-(2,3-Dihydro-benzofuran-5-ylmethylene)-1-(4-iodo-phenyl)-pyrazolidine-3,5-dione,
1-(4-Iodo-phenyl)-4-quinolin-2-ylmethylene-pyrazolidine-3,5-dione,
1-(4-Iodo-phenyl)-4-quinolin-4-ylmethylene-pyrazolidine-3,5-dione,
4-[3-(2-Hydroxy-ethoxy)-benzylidene]-1-(4-iodo-phenyl)-pyrazolidine-3,5-dione,
1-(4-Iodo-phenyl)-4-(5-naphthalen-2-yl-thiophen-2-ylmethylene)-pyrazolidine-3,5-dione,
3-{5-[1-(4-Iodo-phenyl)-3,5-dioxo-pyrazolidin-4-ylidenemethyl]-furan-2-yl}-thiophene-2-carboxylic acid methyl ester,
1-(4-Iodo-phenyl)-4-[5-(2-nitro-4-trifluoromethyl-phenyl)-furan-2-ylmethylene]-pyrazolidine-3,5-dione,
4-(5-Chloro-thiophen-2-ylmethylene)-1-(4-iodo-phenyl)-pyrazolidine-3,5-dione,
1-(4-Iodo-phenyl)-4-thiazol-2-ylmethylene-pyrazolidine-3,5-dione,
1-(4-Iodo-phenyl)-4-(1-methyl-1H-imidazol-2-ylmethylene)-pyrazolidine-3,5-dione,
4-(2-Diethylamino-thiazol-5-ylmethylene)-1-(4-iodo-phenyl)-pyrazolidine-3,5-dione,
4-[2-(4-Benzyl-piperazin-1-yl)-thiazol-5-ylmethylene]-1-(4-iodo-phenyl)-pyrazolidine-3,5-dione,
1-(4-Iodo-phenyl)-4-[2-(4-methoxy-phenoxy)-thiazol-5-ylmethylene]-pyrazolidine-3,5-dione,
4-(9-Ethyl-9H-carbazol-3-ylmethylene)-1-(4-iodo-phenyl)-pyrazolidine-3,5-dione, or 4-Benzo[b]thiophen-3-ylmethylene-1-(4-iodo-phenyl)-pyrazolidine-3,5-dione, or a pharmaceutically acceptable salt thereof or tautomer thereof.

Some embodiments provide a method of evaluating inhibition of Rho GTPase activation property of a compound comprising:
(a) contacting a solution comprising RhoGEF and fluorescent GDP-containing reagent-bound Rho GTPase with the compound and measuring decrease in fluorescence over time; and
(b) contacting a solution containing RGS domain-containing RhoGEF, GDP-bound Rho GTPase and fluorescent GTP containing reagent contacting with the compound and measuring increase in fluorescence over time,
wherein the Rho GTPase inhibitory activity of the compound is indicated by a combination of: a reduction in the rate of decrease of fluorescence in step (a) relative to step (a) performed in the absence of the compound; and a reduction in the rate of increase of fluorescence in step (b) relative to step (b) performed in the absence of the compound.

BRIEF DESCRIPTION OF THE DRAWINGS

FIG. 1A Shows data correlating to the inhibitory effects of Y16 on the interaction between RhoA and multiple RhoGEFs.
FIG. 1B Shows data indicating Y16 has no effect on Cdc42 or Rac1 binding to their respective GEFs. (Top) Myc-tagged Tiam1 expressed in HEK293T cell lysates were incubated with GST alone or GST-Rac1 conjugated with glutathione agarose beads in the presence of increasing concentrations of Y16. (Middle) $(His)_6$-tagged TrioN (1 µg) was incubated with GST alone or GST-Rac1 conjugated with glutathione agarose beads in the presence of increasing concentrations of Y16. (Bottom) $(His)_6$-tagged Cdc42 (1 µg) was incubated with GST alone or GST-Intersectin conjugated with glutathione agarose beads in the presence of increasing concentrations of Y16.
FIG. 2A Shows data indicating Y16 was effective in inhibiting RhoA GDP/GTP exchange reaction stimulated by LARG in a dose-dependent manner.
FIG. 2B Shows microscale thermophoresis analysis of Y16 binding to LARG.
FIG. 2C Shows microscale thermophoresis analysis of Y16 binding to LARG mutants. Purified LARG mutants were first labeled with Alexa 647 fluorescence dye. Y16 was titrated at increasing concentrations. Data are representative of three independent experiments.
FIG. 3A Shows data from the results of NIH 3T3 cells being treated with Y16 at the indicated concentrations for 24 h in serum-free media and then further processed.
FIG. 3B Shows data from the results of NIH 3T3 cells being treated with Y16 at the indicated concentrations for 24 h in serum-free media and then further processed. The relative amounts of GTP-bound form of the GTPases were quantified by densitometry measurements and normalized to those of the unstimulated cells.
FIG. 3C Shows data indicating Y16 inhibited the serum or/and SDF-1α-induced phospho-MLC and phospho-FAK activities.
FIG. 3D Shows the effect of Y16 on cell stress fiber and focal complex was assessed in Swiss 3T3 cells.
FIG. 3E Shows data indicating Y16 does not affect the constitutively active RhoA Q63L mutant-induced actin stress fiber or focal adhesion formation.
FIGS. 4A-D: Synergistic effects of Y16 with Rhosin on GEF-RhoA interaction and RhoA activity.
FIG. 4A Shows data at different concentrations indicating dose-dependent specific inhibition of LARG binding to RhoA by Y16, G04, or G04+Y16 combination.
FIG. 4B Shows data indicating the effects of Y16, G04, or G04+Y16 combination in suppressing RhoA activity in NIH 3T3 cells.
FIG. 4C Shows data indicating the effect of Y16, G04, or G04+Y16 combination on Cdc42 and Rac1 activities.
FIG. 4D Shows data indicating Y16, G04, or G04+Y16 combination selectively blocks cellular response to LPA-stimulated actin stress fiber formation.

FIG. 5A Shows data indicating Y16, G04, or G04+Y16 combination inhibits MCF7 breast cell growth.

FIG. 5B Shows data indicating Y16, G04, or G04+Y16 combination inhibits MCF7 cell migration.

FIG. 5C Shows data indicating Y16, G04, or G04+Y16 combination inhibits MCF7 cells invasion.

FIG. 5D Shows data indicating Y16, G04, or G04+Y16 combination inhibits RhoA and its downstream signaling activities in MCF7-derived mammospheres. (Upper) MCF7-derived mammospheres were treated with Y16, G04, or G04+Y16 combination at the indicated concentrations. (Lower) Western blots are of p-MLC of MCF7-derived mammospheres. Y16, G04, or G04+Y16 combination inhibits MCF-7 cell-derived mammosphere formation.

FIG. 5E Shows data indicating Y16, G04, or G04+Y16 combination inhibits MCF-7 cell-derived mammosphere formation.

FIGS. 6A-B: Provides schemes for complementary HTS assays measuring GDP-dissociation and GTP-association of RhoA catalyzed by LARG.

FIG. 6A Green fluorescence channel tracks FL-GDP dissociation.

FIG. 6B Red fluorescence channel tracks TR-GTP binding to RhoA under LARG catalysis.

FIG. 9A-B: Shows microscale thermophoresis analysis of Y16 binding to TrioN or Intersectin and GEF reaction of Cdc42 or Rac1 catalyzed by Intersectin or TrioN.

FIG. 9A Shows data indicating no binding of Y16 to either Intersectin or TrioN was detected under the assay conditions.

FIG. 9B Shows data from a FL-GDP dissociation assay.

DETAILED DESCRIPTION

Figure 1A:
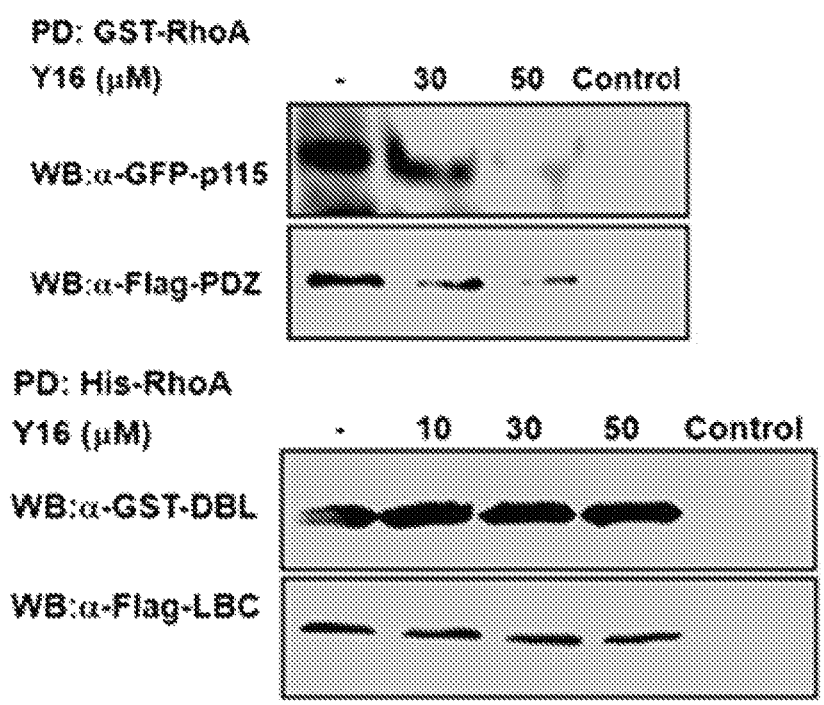
FIGS. 1A-B: Identification of Y16 as an inhibitor of G-protein-coupled Rho GEFs.

It is to be understood that both the foregoing general description and the following detailed description are exemplary and explanatory only and are not restrictive of the embodiments claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The G-protein-mediated Rho guanine nucleotide exchange factor (GEF)-Rho GTPase signaling axis has been implicated in human pathophysiology and is a potential therapeutic target. As provided herein, by screening chemicals that might fit into a surface groove of the DH-PH domain of LARG, a G-protein-regulated Rho GEF involved in RhoA activation, and subsequent validations in biochemical assays, a class of chemical inhibitors was identified, represented by Y16, that are active in specifically inhibiting LARG binding to RhoA. Y16 binds to the junction site of the DH-PH domains of LARG with a ~80 nM $K_d$ and suppresses LARG catalyzed RhoA activation dose dependently. It is active in blocking the interaction of LARG and related G-protein-coupled Rho GEFs with RhoA without a detectable effect on other DBL family Rho GEFs, Rho effectors, or a RhoGAP. In cells, Y16 selectively inhibits serum-induced RhoA activity and RhoA-mediated signaling, effects that can be rescued by a constitutively active RhoA or ROCK mutant. By suppressing RhoA activity, Y16 inhibits mammary sphere formation of MCF7 breast cancer cells but does not affect the nontransforming MCF10A cells. Y16 also works synergistically with Rhosin/G04, a Rho GTPase activation site inhibitor, in inhibiting LARG-RhoA interaction, RhoA activation, and RhoA-mediated signaling functions. Thus, as provided herein, RGS domain-containing Rho GEFs can serve as selective targets for inhibitors and for dual inhibition of the enzyme-substrate pair of GEF-RhoA at their binding interface that leads to enhanced efficacy and specificity.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients.

As used herein, the following terms are defined with the following meanings, unless expressly stated otherwise.

The term "alkyl" refers to a branched or unbranched fully saturated acyclic aliphatic hydrocarbon group. An alkyl may be branched or straight chain. Alkyls may be substituted or unsubstituted. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "alkenyl" used herein refers to a straight or branched chain aliphatic hydrocarbon of from two to twenty carbon atoms containing at least one carbon-carbon double bond including, but not limited to, 1-propenyl, 2-propenyl, 2-methyl-1-propenyl, 1-butenyl, 2-butenyl, and the like. In certain embodiments, an alkenyl comprises 2 to 20 carbon atoms (whenever it appears herein, a numerical range such as "2 to 20" refers to each integer in the given range; e.g., "2 to 20 carbon atoms" means that an alkenyl group may comprise only 2 carbon atoms, 3 carbon atoms, etc., up to and including 20 carbon atoms, although the term "alkenyl" also includes instances where no numerical range of carbon atoms is designated). An alkenyl may be designated as "$C_2$-$C_6$ alkenyl" or similar designations. By way of example only, "$C_2$-$C_4$ alkenyl" indicates an alkenyl having two, three, or four carbon atoms, e.g., the alkenyl is selected from ethenyl, propenyl, and butenyl.

The term "cycloalkyl" used herein refers to saturated aliphatic ring system having three to twenty carbon atoms. A cycloalkyl refers to monocyclic and polycyclic saturated aliphatic ring system including, but not limited to, cyclopropyl, cyclopentyl, cyclohexyl, cycloheptyl, bicyclo[4.4.0]decanyl, bicyclo[2.2.1]heptanyl, adamantyl, norbornyl, and the like. In certain embodiments, a cycloalkyl comprises 3 to 20 carbon atoms (whenever it appears herein, a numerical range such as "3 to 20" refers to each integer in the given range; e.g., "3 to 20 carbon atoms" means that a cycloalkyl group may comprise only 3 carbon atoms, etc., up to and including 20 carbon atoms, although the term "cycloalkyl" also includes instances where no numerical range of carbon atoms is designated). A cycloalkyl may be designated as "$C_3$-$C_7$ cycloalkyl" or similar designations. By way of example only, "$C_3$-$C_6$ cycloalkyl" indicates a cycloalkyl having two, three, four, five or six carbon atoms, e.g., the cycloalkyl is selected from cyclopropyl, cyclobutyl, cyclopentyl, and cyclohexyl.

The term "cycloalkenyl" used herein refers to aliphatic ring system having three to twenty carbon atoms having at least one carbon-carbon double bond in the ring. A cycloalkenyl refers to monocyclic and polycyclic unsaturated aliphatic ring system including, but are not limited to, cyclopropenyl, cyclopentenyl, cyclohexenyl, cycloheptenyl, bicyclo[3.1.0]hexyl, norbornylenyl, 1,1'-bicyclopentenyl, and the like. In certain embodiments, a cycloalkenyl comprises 3 to 20 carbon atoms (whenever it appears herein, a numerical range such as "3 to 20" refers to each integer in the given range; e.g., "3 to 20 carbon atoms" means that a cycloalkenyl group may comprise only 3 carbon atoms, etc., up to and including 20 carbon atoms, although the term "cycloalkenyl" also includes instances where no numerical range of carbon atoms is designated). A cycloalkenyl may be designated as "$C_3$-$C_7$ cycloalkenyl" or similar designations. By way of example only, "$C_3$-$C_6$ cycloalkenyl" indicates an alkenyl having two, three, four, five or six carbon atoms, e.g., the cycloalkyl is selected from cyclopropenyl, cyclobutenyl, cyclopentenyl, and cyclohexenyl.

The term "alkoxy" used herein refers to straight or branched chain alkyl covalently bonded to oxygen where the "alkoxy" is attached to the parent molecule through at least an oxygen linkage. Where an "alkoxy" substituent requires two points of attachment to the rest of the molecule the "alkoxy" is attached to the parent molecule through an oxygen linkage and a carbon linkage. Examples of alkoxy groups include, but are not limited to, methoxy, ethoxy, propoxy, isopropoxy, butoxy, n-butoxy, sec-butoxy, t-butoxy and the like. An alkoxy may be designated as "$C_1$-$C_6$ alkoxy" or similar designations. By way of example only, "$C_1$-$C_4$ alkoxy" indicates an alkyl having one, two, three, or four carbon atoms, e.g., the alkoxy is selected from methoxy, ethoxy, propoxy, iso-propoxy, butoxy, iso-butoxy, sec-butoxy, and tert-butoxy.

The term "heteroalkyl" refers to a group comprising at least one alkyl or alkenyl, and one or two heteroatoms. Where a "heteroalkyl" substituent requires two points of attachment to the rest of the molecule the "heteroalkyl" is attached to the parent molecule through a heteroatom linkage and a carbon linkage, a first carbon linkage and a second carbon linkage, or a first heteroatom linkage and a second heteroatom linkage. Examples of heteroalkyls include, but are not limited to, —CH$_2$OCH$_2$CH$_2$—, —CH$_2$OCH$_2$—, —CH$_2$CH$_2$OCH$_2$CH$_2$—, —CH$_2$OCH═CH—, —CH═CHOCH═CH—, —OCH$_2$O—, —CH$_2$NHCH$_2$CH$_2$—, —CH$_2$NHCH$_2$—, —CH$_2$CH$_2$NHCH$_2$CH$_2$—, —NHCH═CH—, —NHCH$_2$CH$_2$—, —N═CHCH$_2$—, —CH$_2$NHCH═CH—, —CH═CHNHCH═CH—, —NHCH$_2$NH—, and the like.

The term "heterocyclic" or "heterocyclyl" used herein refers to a cyclic ring system radical having at least one non-aromatic ring in which one or more ring atoms are not carbon, namely heteroatom. Monocyclic "heterocyclic" or "heterocyclyl" moieties are non-aromatic. Bicyclic "heterocyclic" or "heterocyclyl" moieties include one non-aromatic ring wherein at least one heteroatom is present in a ring. Tricyclic "heterocyclic" or "heterocyclyl" moieties include at least one non-aromatic ring wherein at least one heteroatom is present in a ring. Examples of heterocyclic groups include, but are not limited to, 1H-isoindolyl, piperidinyl, piperazinyl, morpholinyl, tetrahydrofuranyl, dioxolanyl, tetrahydropyranyl, pyrrolidinyl, and the like.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aryl" refers to an aromatic group wherein each of the atoms forming the ring is a carbon atom. Examples of aryl groups include, but are not limited to phenyl, and naphthalenyl. In certain embodiments, a phenyl group is substituted at one or more positions. Examples of aryl groups comprising substitutions include, but are not limited to, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, hydroxynaphthyl, hydroxymethylphenyl, (trifluoromethyl)phenyl, and 4-morpholin-4-ylphenyl.

The term "heteroaryl" refers to an aromatic mono-, bi- or tricyclic ring system wherein at least one atom forming the aromatic ring system is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl. Examples of heteroaryl groups include, but are not limited to, unsubstituted and mono- or di-substituted derivatives of furan, benzofuran, thiophene, benzothiophene, pyrrole, pyridine, indole, isoindole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline.

The term "arylalkyl" refers to a group comprising an aryl group bound to an alkyl group. Examples of arylalkyl groups include, but are not limited to, benzyl, phenethyl, phenpropyl, phenbutyl, and the like. In some embodiments, arylalkyls may be substituted or unsubstituted, and can be substituted on either the aryl or alkyl portion or on both. Where an "arylalkyl" substituent requires two points of attachment to the rest of the molecule the "arylalkyl" can be attached to the parent molecule through a carbon linkage in the aryl group and a carbon linkage in the alkyl group.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like. In some embodiments, heteroarylalkyls may be substituted or unsubstituted, and can be substituted on either the heteroaryl or alkyl portion or on both. Where an "heteroarylalkyl" substituent requires two points of attachment to the rest of the molecule the "heteroarylalkyl" can be attached to the parent molecule through a carbon linkage in the heteroaryl group and a carbon linkage in the alkyl group.

The term "heterocyclylalkyl" used herein refers to one or more heterocyclyl groups appended to an alkyl radical. Examples of heterocyclylalkyl include, but are not limited to, piperidinylmethyl, piperidinylethyl, morpholinylmethyl, morpholinylethyl, and the like.

The term "(cycloalkyl)alkyl" used herein refers to one or more cycloalkyl groups appended to an alkyl radical. Examples of (cycloalkyl)alkyl include, but are not limited to, cyclohexylmethyl, cyclohexylethyl, cyclopentylmethyl, cyclopentylethyl, and the like. In some embodiments, (cycloalkyl)alkyl may be substituted or unsubstituted.

Unless otherwise indicated, the term "optionally substituted," refers to a group in which none, one, or more than one of the hydrogen atoms has been replaced with one or more group(s) individually and independently selected from: alkyl, alkenyl, cycloalkenyl, cycloalkyl, aryl, arylalkyl, heteroaryl, heterocyclyl, hydroxy, alkoxy, cyano, halo, oxo, thiocarbonyl, ester, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, including mono- and di-substituted amino groups, and the protected derivatives of amino groups. Such protective derivatives (and protecting groups that may form such protective derivatives) are known to those of skill in the art and may be found in references such as Greene and Wuts, above. When the group contains a nitrogen, or a sulfur, an oxo as a substituent also includes oxides, for example pyridine-N-oxide, thiopyran sulfoxide and thiopyran-S,S-dioxide. In embodiments in which two or more hydrogen atoms have been substituted, the substituent groups may together form a ring.

The substituent "R" appearing by itself and without a number designation refers to a substituent selected from H (hydrogen), alkyl, cycloalkyl, aryl, heteroaryl (bonded through a ring carbon) and heterocyclyl (bonded through a ring carbon).

The term "O-carboxy" refers to the group consisting of formula RC(=O)O—.

The term "C-carboxy" refers to the group consisting of formula —C(=O)OR.

The term "cyano" refers to the group consisting of formula —CN.

The term "isocyanato" refers to the group consisting of formula —N=C=O.

The term "thiocyanato" refers to the group consisting of formula —CNS.

The term "isothiocyanato" refers to the group consisting of formula —N=C=S.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "ester" refers to a chemical moiety with formula —(R)$_n$—C(=O)OR', where R and R' are independently selected from alkyl, cycloalkyl, aryl, heteroaryl (bonded through a ring carbon) and non-aromatic heterocycle (bonded through a ring carbon), where n is 0 or 1.

The term "amino" refers to a chemical moiety with formula —NHR'R", where R' and R" are each independently selected from hydrogen, alkyl, cycloalkyl, aryl, heteroaryl (bonded through a ring carbon) and heteroalicyclic (bonded through a ring carbon).

The term "stereoisomers" as used herein means isomers that possess identical constitution, but which differ in the arrangement of their atoms in space. Including, for example, all enantiomers, diastereomers, geometric isomers, and atropisomers.

Wherever a substituent as depicted as a di-radical (i.e., has two points of attachment to the rest of the molecule), it is to be understood that the substituent can be attached in any directional configuration unless otherwise indicated. Thus, for example, a substituent depicted as -AE- or

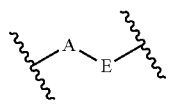

includes the substituent being oriented such that the A is attached at the leftmost attachment point of the depicted structure as well as attached at the rightmost attachment point of the depicted structure.

It is to be understood that certain radical naming conventions can include either a mono-radical or a di-radical, depending on the context. For example, where a substituent requires two points of attachment to the rest of the molecule, it is understood that the substituent is a di-radical. A substituent identified as alkyl, that requires two points of attachment, includes di-radicals such as —CH$_2$—, —CH$_2$CH$_2$—, —CH$_2$CH(CH$_3$)CH$_2$—, and the like; a substituent depicted as alkoxy that requires two points of attachment, includes di-radicals such as —OCH$_2$—, —OCH$_2$CH$_2$—, —OCH$_2$CH(CH$_3$)CH$_2$—, and the like: and a substituent identified as arylalkyl that requires two points of attachment, includes di-radicals such as

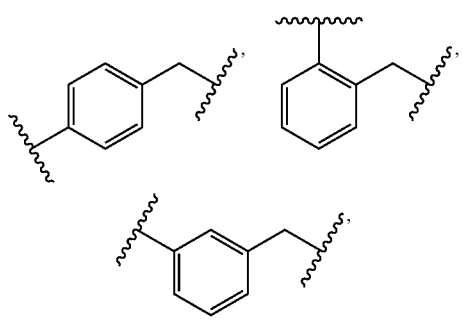

and the like.

Throughout the specification, groups and substituents thereof can be chosen by one skilled in the field to provide stable moieties and compounds.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect. The therapeutically effective amount of compound of Formula I may be the amount of compound of Formula I to reduce the size and/or number of tumors and/or metastatic cancer cells. In some embodiments, the amount of compound of Formula I or pharmaceutically acceptable salt thereof may be from about 1 mg to about 2 grams per unit dosage. In some embodiments, the amount of compound of Formula I or pharmaceutically acceptable salt thereof may be from about 1, 2, 5, 10, 15, 20, 25, 30, 40, 50, or 60 mg to about 75 mg per unit dosage. In some embodiments, the amount of compound of Formula I or pharmaceutically acceptable salt thereof may be from about 1.3 grams to about 2 grams per unit dosage.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

Certain Compounds

Certain compounds that modulate Rho GTPase activation, for example compounds that modulate RhoA activation, RhoA/RGS domain-containing RhoGEF interaction, and/or bind to RGS domain-containing RhoGEF play a role in health. In some embodiments, the Rho GTPase activation is RhoA activation. In some embodiments, compounds are useful for treating diseases or conditions as provided elsewhere herein.

Rho family GTPases are intracellular signal transducers involved in diverse cell signal transduction processes from cell adhesion molecules, growth factor receptors, and G-protein-coupled receptors. The DBL family GEFs are the major class of activators for Rho GTPases including RhoA, Cdc42, and Rac1, and are known to possess transforming activity (6-10). The three DBL family members, LARG, PDZRhoGEF, and p115 RhoGEF, represent a distinct RhoGEF subfamily characterized by the presence of a RGS domain at their N termini that binds to the heterotrimeric G$\alpha_{12/13}$-proteins, and also the RhoGEF module, DH-PH domains, that directly signals to RhoA (11-15). The G$\alpha_{12/13}$-RhoGEF-RhoA pathway has been implicated in cancer cell migration, invasion, and proliferation.

As provided herein DH-PH module of RGS domain-containing RhoGEFs (LARG, PDZRhoGEF, and p115 RhoGEF) appear suitable for targeting by small-molecule inhibitors, where the inhibitors bind near LARG residues N975 and R986, which are required for Rho GTPase substrate recognition and catalysis (5). Furthermore, as enzymes, RhoGEFs serve as effective targets because a partial blockade of the GEF activity result in an amplified suppression of downstream Rho GTPase signal flows. Thus, provided herein are compounds targeting the site of a G-protein-coupled RhoGEF enzyme essential for Rho activation, i.e., the DH-PH junction of LARG.

One compound provided herein, Y16, docks with a favorable energy into the C terminus of LARG DH domain junction site with PH domain, a region critical for RhoA recognition and catalysis. Y16 and its analogs show a specific inhibitory activity of LARG. Y16 displayed a specificity against the heterotrimeric G-protein-regulated RGS domain-containing RhoGEFs, i.e., LARG, p115RhoGEF, and PDZRho-GEF, with a measured binding constant of ~76 nM $K_d$, and did not interfere with the action of other RhoA-activating DBL family RhoGEFs such as DBL and LBC. Mutagenesis studies of LARG indicate that the Y16 binding site is located in the C terminus of the DH domain, a region essential for RhoA interaction. In cells, Y16 displays a selective inhibition of RhoA-GTP formation and RhoA-mediated F-actin stress fiber and focal adhesion formation. The cellular inhibitory effects of Y16 can be rescued by the expression of a constitutively active RhoA or ROK mutant that is capable of bypassing endogenous RhoA-GTP to elicit downstream signaling. These biochemical and cell-biological properties indicate that Y16 is a G-protein-coupled RhoGEF selective inhibitor. While not intending to be limited to the following, it appears that the highly conserved structures of the LARG subfamily G-protein-coupled RhoGEFs contain unique residues corresponding to K979 and N983 of LARG to allow a distinction of Y16 and analogs from other DBL family DH-PH containing GEFs.

Rhosin/G04, which contains two aromatic chemical fragments tethered by a flexible linker and may dock into two separate shallow grooves sandwiching the GEF recognition site of RhoA between the switch I and switch II regions (26) displays a micromolar binding affinity to RhoA and can inhibit GEF binding to RhoA (26). As provided herein, the compounds of Formula I and Rhosin work synergistically to inhibit LARG-RhoA signaling. When being applied together, the compounds of Formula I and Rhosin yield a synergistic potency in suppressing LARG-RhoA interaction in vitro and RhoA activation in cells. This synergy is also enhances specificity, in addition to potency, for inhibiting the GEF-RhoA signaling pathway and shows an advantage in an approach of "one interactive site, two drugs" in rationally devising inhibitors interfering with an enzyme-substrate interface. Also provided herein is a cancer cell model demonstrating that a combined application of the compounds of Formula I and Rhosin is advantageous at more effectively inhibiting RhoA activity and tumor sphere growth.

One of skill in the art will recognize that analogous synthesis schemes may be used to synthesize similar compounds. One of skill in the art will recognize that compounds of the present embodiments may be synthesized using other synthesis schemes.

In certain embodiments, a salt corresponding to a compound as disclosed and described herein is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a compound as disclosed and described herein with multiple molar equivalents of a base, such as bis-sodium, bis-ethanolamine, and the like.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

As provided herein, G-protein-coupled RGS domain-containing RhoGEFs constitute valid targets and can be specifically targeted at the catalytic site of DH-PH domains by inhibitors. Furthermore, provided herein is a strategy to target RhoA signaling by dual inhibitors of the GEF-RhoA pair of enzyme-substrate interface, to achieve improved efficacy and specificity, expanding the traditional "one target, one drug" approach in rational drug design.

Compositions

The present embodiments further provide compositions, including pharmaceutical compositions, comprising compounds of the general Formula I, or pharmaceutically acceptable salt thereof, or tautomer thereof.

A subject pharmaceutical composition comprises a subject compound; and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The methods and compositions described herein are generally useful in treatment of breast cancer, leukemia, or lung cancer. In some embodiments, the breast cancer is metastatic breast cancer. In some embodiments, the lung cancer is metastatic lung cancer. In some embodiments, the leukemia is acute myeloid leukemia. The examples provided herein demonstrate the effectiveness of these compounds in a breast cancer model. Those skilled in the art will recognize that the underlying mechanism of inhibition of RGS domain-containing GEF mediated Rho GTPase activation, such as RhoA activation, in breast cancer, leukemia and lung cancer provide support for the results provided herein to be readily applicable to leukemia and lung cancer.

In the subject methods, the active agent(s) (e.g., compound of Formula I) may be administered to the host using any convenient means capable of resulting in the desired therapeutic effect. Thus, the agent can be incorporated into a variety of formulations for therapeutic administration. More particularly, the agents of the embodiments can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations

The above-discussed compounds can be formulated using well-known reagents and methods. Compositions are provided in formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20$^{th}$ edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a compound is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

As such, administration of the compounds can be achieved in various ways, including oral, buccal, rectal, parenteral, intraperitoneal, intradermal, subcutaneous, intramuscular, transdermal, intratracheal, etc., administration.

In some embodiments, the pharmaceutical compositions can be administered orally, rectally, or parenterally. Oral administration or administration by injection is preferred.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the embodiments depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the method of treating breast cancer, leukemia, or lung cancer includes administering a compound of Formula I to a subject in need thereof. In some embodiments, the method further includes administration of one or more additional anti-cancer agents. In some embodiments, the method further includes administration of (2R)-2-amino-3-(1Hindol-3-yl)-N'-[(1E)-quinoxalin-6-ylmethylidene]propanehydrazide having the structure:

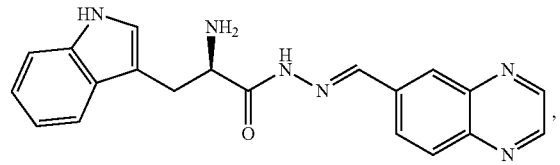

(compound G04)

(compound G04), or a pharmaceutically acceptable salt thereof.

Routes of Administration

In some embodiments, the one or more additional anti-cancer agents may be administered orally in capsule or tablet form, or in the same or different administration form and in the same or different route as the compound of Formula I. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient. In some embodiments, a compounds as described herein can be administered orally.

In connection with the above-described methods for the treatment of breast cancer, leukemia, or lung cancer in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

In some embodiments, based on the teachings provided herein, the compounds provided herein can be used in methods of treating or relieving the symptoms of breast cancer, leukemia, or lung cancer. In some embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. In some embodiments, the compounds as described herein can be administered 5 times per day, 4 times per day, 3 times per day or 2 times per day. In some embodiments, the compound may be administered as a continuous infusion.

In connection with the above-described methods for the treatment of breast cancer, leukemia, or lung cancer in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

In some embodiments, based on the teachings provided herein, the compounds provided herein can be used in methods of treating or relieving the symptoms of diseases such as breast cancer (including ductal carcinoma lobule carcinoma and breast epithelial cancer), ovarian cancer (including epithelial ovarian cancer), desmoid tumor, malignant peripheral nerve sheath cancer, acute leukemia, rhabdomyosarcoma, Ewing's sarcoma, extra-skeletal myxoid chondrosarcoma, or endometrial cancer. In many embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. In some embodiments, the Rho GTPase inhibitor compounds, such as RhoA inhibitor compounds, as described herein can be administered 5 times per day, 4 times per day, 3 times per day or 2 times per day. In other embodiments, the Rho GTPase inhibitor compound, such as RhoA inhibitor compound, may be administered as a continuous infusion.

In some embodiments, the amount of active ingredient that may be combined with carrier materials to produce a dosage form can vary depending on the host to be treated and the particular mode of administration. A typical pharmaceutical preparation can contain from about 5% to about 95% active ingredient (w/w). In some embodiments, the pharmaceutical preparation can contain from about 20% to about 80% active ingredient.

Those of skill will readily appreciate that dose levels can vary as a function of the specific compound, the severity of the symptoms and the susceptibility of the subject to side effects.

Methods of Screening for Rho GTPase Inhibition

Also provided herein are methods of screening compounds for Rho GTPase inhibition, such as RhoA, Rac, and Cdc42 Inhibition. These methods can include methods of evaluating inhibitory properties of a compound, such as, but not limited to, a member of the set of compounds provided herein. In some embodiments, the methods can comprise contacting a Rho GTPase, such as RhoA, with a compound, and evaluating the level of Rho GTPase inhibition, such as RhoA inhibition. In some embodiments, the methods can comprise contacting Rho GTPase, such as RhoA, with a compound, and evaluating the level of inhibition of GDP dissociation from a Rho GTPase, such as RhoA. In some embodiments, the methods can comprise contacting a Rho GTPase, such as RhoA, with a compound, and evaluating the level of inhibition of GTP association with Rho GTPase, such as RhoA, in accordance with the methods disclosed herein or otherwise known in the art. In some embodiments, the methods comprise evaluating both dissociation and association, in accordance with the methods disclosed herein or otherwise known in the art. In certain embodiments, the compound is a compound as disclosed and described herein, such as a compound of Formula I.

The Rho GTPase, such as RhoA, can be from any organism that expresses Rho GTPase, such as RhoA, such as those that are known in the art. In some embodiments, the Rho GTPase, such as RhoA, may be from a mammalian organism, such as human, primate, bovine, equine, porcine, ovine, murine, canine or feline Rho GTPase, such as RhoA. In typical embodiments, the Rho GTPase, such as RhoA, may be from human or primate. In some embodiments, the Rho GTPase, such as RhoA, is a recombinant and/or truncated form of Rho GTPase, such as RhoA, such as a form disclosed herein or otherwise known in the art as being suitable for assessing Rho GTPase activation, such as RhoA activation.

In some embodiments, the methods can comprise evaluating the level of Rho GTPase inhibition, such as RhoA inhibition, using a cell-free assay as described herein or otherwise known in the art. For example, in some embodiments, the method comprises measuring inhibition of Rho GTPase, such as RhoA, using a dissociation assay and an association assay as described herein where inhibitory activity is shown in both assays. In some embodiments, the dissociation assay may be a dissociation fluorescence assay as described herein or otherwise known in the art. In some embodiments, the association assay may be an association fluorescence assay as described herein or otherwise known in the art.

In some embodiments, the inhibition can be determined by comparing the decrease in decrease of fluorescence in a sample with a compound of Formula I and the decrease in decrease of fluorescence in a sample without a compound of Formula I over a set time period. In some embodiments, the inhibition can be determined by comparing the decrease in increase of fluorescence in a sample with a compound of Formula I and the decrease in increase of fluorescence in a sample without a compound of Formula I over a set time period.

In some embodiments, a user-selected level of inhibition of a compound can be, for example, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease in the rate of GDP dissociation from Rho GTPase, such as RhoA, relative to the amount of dissociation when the compound is absent or relative to the amount of dissociation inhibited by a reference compound. In some embodiments, a user-selected level of inhibition of a compound can be, for example, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease in the rate of GTP association with Rho GTPase, such as RhoA, relative to the amount of association when the compound is absent or relative to the amount of association inhibited by a reference compound. In some embodiments, a user-selected level of inhibition can be an $IC_{50}$ value that is, for example, less than 10 mM, 1 mM, 100 µM, 90 µM, 80 µM, 70 µM, 60 µM, 50 µM, 40 µM, 30 µM, 20 µM, 10 µM, 1 µM, 0.1 µM, 0.01 µM, or less than 0.001 µM, as described herein or otherwise known in the art. In some embodiments, the amount of compound used in the assay may be 10 µM and the level of inhibition can be, for example, at least 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease in the rate of GDP dissociation from Rho GTPase, such as RhoA, relative to the amount of dissociation when the compound is absent or relative to the amount of dissociation inhibited by a reference compound. In some embodiments, the amount of compound used in the assay may be 10 µM and the level of inhibition can be, for example, at least 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease in the rate of GTP association from Rho GTPase, such as RhoA, relative to the amount of association when the compound is absent or relative to the amount of association inhibited by a reference compound. In some embodiments, the compound is determined to be an inhibitor of Rho GTPase activation, such as RhoA activation, when the compound demonstrates both the ability to reduce GDP dissociation and the ability to reduce GTP association with Rho GTPase, such as RhoA, relative to the amount of dissociation and association, respectively, when the compound is absent or relative to the amount of dissociation and association that occurs when a reference compound is present.

The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds.

In some embodiments, the methods can comprise an in vitro assay on whole cells as described herein or otherwise known in the art. In some embodiments, the methods can comprise an in vivo assay as described herein or otherwise known in the art.

EXAMPLES

The following examples are set forth merely to assist in understanding the embodiments and should not be construed as limiting the embodiments described and claimed herein in any way. Variations of the invention, including the substitution of all equivalents now known or later developed, which would be within the purview of those skilled in the art, and changes in formulation or minor changes in experimental design, are to be considered to fall within the scope of the embodiments incorporated herein.

The compounds of Formula I can be prepared according to methods known in the art. For example, the compounds of Formula I can be prepared according to the methods shown in U.S. Publication No. 2004/0220188 using the appropriate chemical reagents to obtain the desired compounds. A general discussion of tautomeric forms relevant to compounds of Formula I can be found in U.S. Publication No. 2004/0220188.

Some embodiments provide a compound having the structure of Formula I:

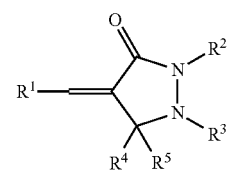

or a pharmaceutically acceptable salt thereof or tautomer thereof,
wherein:
$R^1$ is aryl, heteroaryl, or heterocyclyl, each optionally substituted with one or more $R^{1A}$ with the proviso that $R^1$ is not furanyl or furanyl substituted with optionally substituted aryl;
each $R^{1A}$ is independently selected from the group consisting of hydroxy, halo, cyano, nitro, —$SO_2OH$, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;
each $R^{1B}$ is independently selected from the group consisting of —$OR^{1C}$, C-carboxy, O-carboxy, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is H (hydrogen), aryl, or heteroaryl, said aryl or heteroaryl each optionally substituted with one or more $R^{2A}$;

each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);

each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^4$ is H (hydrogen), or $C_{1-6}$ alkyl; and $R^5$ is H (hydrogen), or $C_{1-6}$ alkyl, or optionally $R^4$ and $R^5$ together are oxo, with the proviso that the compound is not:

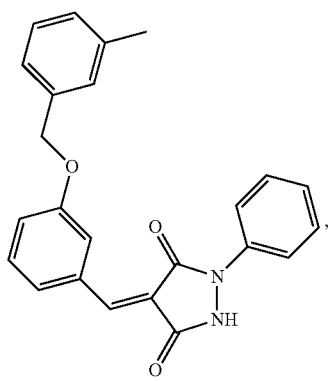 [SMILES: Cc1cccc(COc2cccc(/C=C3/C(=O)NN(c4ccccc4)C3=O)c2)c1]

4-(4-Iodo-benzylidene)-1-(4-iodo-phenyl)-pyrazolidine-3,5-dione,
4-(Dimethyl-furan-2-ylmethylene)-1-(3-trifluoromethyl-phenyl)-pyrazolidine-3,5-dione,
Acetic acid 5-[1-(4-iodo-phenyl)-3,5-dioxo-pyrazolidin-4-ylidenemethyl]-furan-2-ylmethyl ester,
4-(4-Bromo-furan-2-ylmethylene)-1-(4-iodo-phenyl)-pyrazolidine-3,5-dione,
1-(4-Iodo-phenyl)-4-(5-methyl-furan-2-ylmethylene)-pyrazolidine-3,5-dione,
4-(5-Bromo-furan-2-ylmethylene)-1-(4-iodo-phenyl)-pyrazolidine-3,5-dione,
1-(4-Iodo-phenyl)-4-[5-(2-methoxy-phenyl)-thiophen-2-ylmethylene]-pyrazolidine-3,5-dione,
1-(4-Iodo-phenyl)-4-thiophen-3-ylmethylene-pyrazolidine-3, 5-dione,
1-(4-Iodo-phenyl)-4-(5-phenyl-thiophen-2-ylmethylene)-pyrazolidine-3,5-dione,
4-(5-Methyl-furan-2-ylmethylene)-1-(3-trifluoromethyl-phenyl)-pyrazolidine-3,5-dione,
4-Thiophen-2-ylmethylene-1-(3-trifluoromethyl-phenyl)-pyrazolidine-3,5-dione,
4-(4-Bromo-furan-2-ylmethylene)-1-(3-trifluoromethyl-phenyl)-pyrazolidine-3, 5-dione,
Acetic acid 5-[3,5-dioxo-1-(3-trifluoromethyl-phenyl)-pyrazolidin-4-ylidenemethyl]-furan-2-ylmethyl ester,
4-(7-Bromo-8-hydroxy-quinolin-5-ylmethylene)-1-(4-iodo-phenyl)-pyrazolidine-3,5-dione,
1-(4-Iodo-phenyl)-4-[5-(4-nitro-phenyl)-furan-2-ylmethylene]-pyrazolidine-3,5-dione,
1-(4-Iodo-phenyl)-4-[5-(2-nitro-phenyl)-furan-2-ylmethylene]-pyrazolidine-3,5-dione,
4-(5-Hydroxymethyl-furan-2-ylmethylene)-1-(4-iodo-phenyl)-pyrazolidine-3,5-dione,
1-(4-Iodo-phenyl)-4-(5-nitro-thiophen-2-ylmethylene)-pyrazolidine-3,5-dione,
4-(5-Hydroxymethyl-furan-2-ylmethylene)-1-(3-trifluoromethyl-phenyl)-pyrazolidine-3,5-dione,
4-(5-Nitro-thiophen-2-ylmethylene)-1-(3-trifluoromethyl-phenyl)-pyrazolidine-3,5-dione,
1-(4-Iodo-phenyl)-4-(5-nitro-furan-2-ylmethylene)-pyrazolidine-3,5-dione,
4-(4,5-Dimethyl-furan-2-ylmethylene)-1-(4-iodo-phenyl)-pyrazolidine-3,5-dione,
5-[1-(4-Iodo-phenyl)-3,5-dioxo-pyrazolidin-4-ylidenemethyl]-furan-2-sulfonic acid,
4-[1-(4-Iodo-phenyl)-3,5-dioxo-pyrazolidin-4-ylidenemethyl]-benzonitrile,
1-(4-Iodo-phenyl)-4-(3-methyl-thiophen-2-ylmethylene)-pyrazolidine-3,5-dione,
4-(4-Bromo-thiophen-2-ylmethylene)-1-(4-iodo-phenyl)-pyrazolidine-3,5-dione,
1-(4-Iodo-phenyl)-4-(5-methyl-thiophen-2-ylmethylene)-pyrazolidine-3,5-dione,
4-Benzo[b]thiophen-2-ylmethylene-1-(4-iodo-phenyl)-pyrazolidine-3,5-dione,
1-(4-Iodo-phenyl)-4-(4-nitro-thiophen-2-ylmethylene)-pyrazolidine-3,5-dione,
5-[1-(4-Iodo-phenyl)-3,5-dioxo-pyrazolidin-4-ylidenemethyl]-thiophene-3-carboxylic acid,
4-[1-(4-Iodo-phenyl)-3,5-dioxo-pyrazolidin-4-ylidenemethyl]-thiophene-3-carboxylic acid,
2-[3,5-Dioxo-1-(3-trifluoromethyl-phenyl)-pyrazolidin-4-ylidenemethyl]-thiophene-3-carboxylic acid,
4-(4-Nitro-thiophen-2-ylmethylene)-1-(3-trifluoromethyl-phenyl)-pyrazolidine-3,5-dione,
4-[3,5-Dioxo-1-(3-trifluoromethyl-phenyl)-pyrazolidin-4-ylidenemethyl]-thiophene-3-carboxylic acid,
{3-[3,5-Dioxo-1-(3-trifluoromethyl-phenyl)-pyrazolidin-4-ylidenemethyl]-thiophen-2-ylsulfanyl-acetic acid,
2-[1-(4-Iodo-phenyl)-3,5-dioxo-pyrazolidin-4-ylidenemethyl]-thiophene-3-carboxylic acid,
4-(4-Hydroxymethyl-furan-3-ylmethylene)-1-(3-trifluoromethyl-phenyl)-pyrazolidine-3,5-dione,
4-benzo[b]thiophen-2-ylmethylene-1-(3-trifluoromethyl-phenyl)-pyrazolidine-3,5-dione,
5-[3,5-Dioxo-1-(3-trifluoromethyl-phenyl)-pyrazolidin-4-ylidenemethyl]-thiophene-3-carboxylic acid,
5-[1-(4-Iodo-phenyl)-3,5-dioxo-pyrazolidin-4-ylidenemethyl]-furan-2-carboxylic acid,
5-(1-Biphenyl-4-yl-3,5-dioxo-pyrazolidin-4-ylidenemethyl)-furan-2-carboxylic acid,
4-(4-Hydroxy-naphthalen-1-ylmethylene)-1-(4-iodo-phenyl)-pyrazolidine-3,5-dione, 1-(4-Iodo-phenyl)-4-(1-oxy-pyridin-4-ylmethylene)-pyrazolidine-3,5-dione,
4-(1H-Indol-5-ylmethylene)-1-(4-iodo-phenyl)-pyrazolidine-3,5-dione,
4-(4-Hydroxymethyl-furan-3-ylmethylene)-1-(4-iodo-phenyl)-pyrazolidine-3, 5-dione,
1-(4-Iodophenyl)-4-(1H-pyrrol-2-ylmethylene)-pyrazolidine-3,5-dione,
1-(4-Iodophenyl)-4-(1-methyl-1H-pyrrol-2-ylmethylene)-pyrazolidine-3,5-dione,
1-(4-Iodo-phenyl)-4-[1-(2-nitro-benzyl)-1H-pyrrol-2-ylmethylene]-pyrazolidine-3,5-dione,
1-(4-Iodo-phenyl-4-(1H-pyrazol-3-ylmethylene)-pyrazolidine-3,5-dione,
1-(4-Iodo-phenyl)-4-(1H-pyrazol-3-ylmethylene)-pyrazolidine-3,5-dione,
4-(2,3-Dihydro-benzofuran-5-ylmethylene)-1-(4-iodo-phenyl)-pyrazolidine-3,5-dione,
1-(4-Iodo-phenyl)-4-quinolin-2-ylmethylene-pyrazolidine-3,5-dione,
1-(4-Iodo-phenyl)-4-quinolin-4-ylmethylene-pyrazolidine-3,5-dione,
4-[3-(2-Hydroxy-ethoxy)-benzylidene]-1-(4-iodo-phenyl)-pyrazolidine-3,5-dione,
1-(4-Iodo-phenyl)-4-(5-naphthalen-2-yl-thiophen-2-ylmethylene)-pyrazolidine-3,5-dione,
3-{5-[1-(4-Iodo-phenyl)-3,5-dioxo-pyrazolidin-4-ylidenemethyl]-furan-2-yl}-thiophene-2-carboxylic acid methyl ester,
4-(5-Chloro-thiophen-2-ylmethylene)-1-(4-iodo-phenyl)-pyrazolidine-3,5-dione,
[1-(4-Iodo-phenyl)-4-thiazol-2-ylmethylene-pyrazolidine-3,5-dione,
1-(4-Iodo-phenyl)-4-(1-methyl-1H-imidazol-2-ylmethylene)-pyrazolidine-3,5-dione,
4-(2-Diethylamino-thiazol-5-ylmethylene)-1-(4-iodo-phenyl)-pyrazolidine-3,5-dione,
4-[2-(4-Benzyl-piperazin-1-yl)-thiazol-5-ylmethylene]-1-(4-iodo-phenyl)-pyrazolidine-3,5-dione,
1-(4-Iodo-phenyl)-4-[2-(4-methoxy-phenoxy)-thiazol-5-ylmethylene]-pyrazolidine-3,5-dione,
4-(9-Ethyl-9H-carbazol-3-ylmethylene)-1-(4-iodo-phenyl)-pyrazolidine-3, 5-dione, or 4-Benzo[b]thiophen-3-ylmethylene-1-(4-iodo-phenyl)-pyrazolidine-3,5-dione,
or a pharmaceutically acceptable salt thereof or tautomer thereof.

Some embodiments provide a composition comprising a pharmaceutically acceptable excipient, and a compound as disclosed and described herein, or a pharmaceutically acceptable salt thereof or tautomer thereof. In some embodiments, the composition further comprising a compound having the structure:

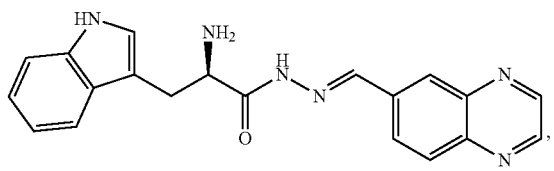 [SMILES: N[C@H](Cc1c[nH]c2ccccc12)C(=O)N/N=C/c1ccc2nccnc2c1]

or a pharmaceutically acceptable salt thereof.

Some embodiments provide a method of evaluating the inhibition of Rho GTPase activation comprising contacting a RGS domain-containing RhoGEF with a compound as disclosed and described herein, or a pharmaceutically acceptable salt thereof or tautomer thereof.

Some embodiments provide a unit dosage of a pharmaceutical composition for treating breast cancer, leukemia, or lung cancer comprising a pharmaceutically acceptable excipient, and a therapeutically effective amount of a compound having the structure of Formula I:

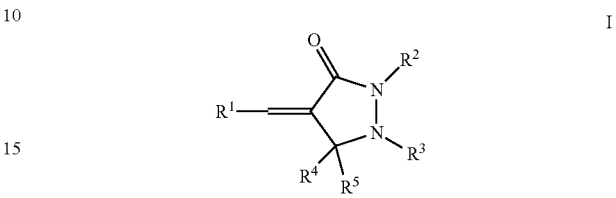

or a pharmaceutically acceptable salt thereof or tautomer thereof,
wherein:
$R^1$ is aryl, heteroaryl, or heterocyclyl, each optionally substituted with one or more $R^{1A}$;
each $R^{1A}$ is independently selected from the group consisting of hydroxy, halo, cyano, nitro, —SO$_2$OH, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted C$_{3-7}$ cycloalkyl, optionally substituted aryl, optionally substituted heteroaryl, optionally substituted heterocyclyl, C$_{1-6}$ alkyl optionally substituted with up to 5 $R^{1B}$, and C$_{1-6}$ alkoxy optionally substituted with up to 5 $R^{1B}$;
each $R^{1B}$ is independently selected from the group consisting of —OR$^{1C}$, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted C$_{3-7}$ cycloalkyl, optionally substituted aryl, optionally substituted heteroaryl, optionally substituted heterocyclyl, C$_{1-6}$ alkyl optionally substituted with up to 5 fluoro, and C$_{1-6}$ alkoxy optionally substituted with up to 5 fluoro;
each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted C$_{3-7}$ cycloalkyl, optionally substituted aryl, optionally substituted heteroaryl, optionally substituted heterocyclyl, C$_{1-6}$ alkyl optionally substituted with up to 5 fluoro, and C$_{1-6}$ alkoxy optionally substituted with up to 5 fluoro;
$R^2$ is H (hydrogen), aryl, or heteroaryl, said aryl or heteroaryl each optionally substituted with one or more $R^{2A}$;
each $R^{2A}$ is independently selected from the group consisting of hydroxy, halo, cyano, nitro, O-carbamyl, N-carbamyl, C-amido, N-amido, C-carboxy, O-carboxy, amino, optionally substituted C$_{3-7}$ cycloalkyl, optionally substituted aryl, optionally substituted heteroaryl, optionally substituted heterocyclyl, C$_{1-6}$ alkyl optionally substituted with up to 5 fluoro, and C$_{1-6}$ alkoxy optionally substituted with up to 5 fluoro;

R³ is H (hydrogen), aryl, or heteroaryl, said aryl or heteroaryl each optionally substituted with one or more R³⁴, provided that one of R² and R³ is H (hydrogen) and one of R² and R³ is not H (hydrogen);

each R³⁴ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

R⁴ is H (hydrogen), or $C_{1-6}$ alkyl; and R⁵ is H (hydrogen), or $C_{1-6}$ alkyl, or optionally R⁴ and R⁵ together are oxo. In some embodiments, the unit dosage form further comprises a compound having the structure:

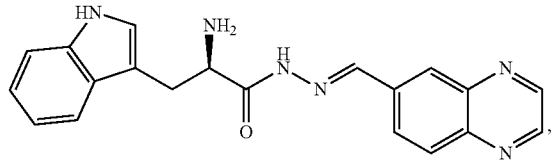 [SMILES: N[C@H](Cc1c[nH]c2ccccc12)C(=O)N/N=C/c1ccc2nccnc2c1]

or a pharmaceutically acceptable salt thereof. In some embodiments, the compound of Formula I in the unit dosage is not:

4-(4-Iodo-benzylidene)-1-(4-iodo-phenyl)-pyrazolidine-3,5-dione,
4-(Dimethyl-furan-2-ylmethylene)-1-(3-trifluoromethyl-phenyl)-pyrazolidine-3,5-dione,
1-Biphenyl-4-yl-4-furan-2-ylmethylene-pyrazolidine-3,5-dione,
Acetic acid 5-[1-(4-iodo-phenyl)-3,5-dioxo-pyrazolidin-4-ylidenemethyl]-furan-2-ylmethyl ester,
4-(4-Bromo-furan-2-ylmethylene)-1-(4-iodo-phenyl)-pyrazolidine-3,5-dione,
1-(4-Iodo-phenyl)-4-(5-methyl-furan-2-ylmethylene)-pyrazolidine-3,5-dione,
4-(5-Bromo-furan-2-ylmethylene)-1-(4-iodo-phenyl)-pyrazolidine-3,5-dione,
1-(4-Iodo-phenyl)-4-[5-(2-methoxy-phenyl)-thiophen-2-ylmethylene]-pyrazolidine-3,5-dione,
1-(4-Iodo-phenyl)-4-thiophen-3-ylmethylene-pyrazolidine-3, 5-dione,
1-(4-Iodo-phenyl)-4-(5-phenyl-thiophen-2-ylmethylene)-pyrazolidine-3,5-dione,
4-Furan-2-ylmethylene-1-(3-trifluoromethyl-phenyl)-pyrazolidine-3,5-dione,
4-(5-Methyl-furan-2-ylmethylene)-1-(3-trifluoromethyl-phenyl)-pyrazolidine-3,5-dione,
4-Thiophen-2-ylmethylene-1-(3-trifluoromethyl-phenyl)-pyrazolidine-3,5-dione,
4-(4-Bromo-furan-2-ylmethylene)-1-(3-trifluoromethyl-phenyl)-pyrazolidine-3,5-dione,
Acetic acid 5-[3,5-dioxo-1-(3-trifluoromethyl-phenyl)-pyrazolidin-4-ylidenemethyl]-furan-2-ylmethyl ester,
1-(3-Chloro-4-methyl-phenyl)-4-furan-2-ylmethylene-pyrazolidine-3,5-dione,
4-(7-Bromo-8-hydroxy-quinolin-5-ylmethylene)-1-(4-iodo-phenyl)-pyrazolidine-3, 5-dione,
1-(4-Iodo-phenyl)-4-[5-(4-nitro-phenyl)-furan-2-ylmethylene]-pyrazolidine-3,5-dione,
1-(4-Iodo-phenyl)-4-[5-(2-nitro-phenyl)-furan-2-ylmethylene]-pyrazolidine-3,5-dione,
4-(5-Hydroxymethyl-furan-2-ylmethylene)-1-(4-iodo-phenyl)-pyrazolidine-3,5-dione,
4-Furan-3-ylmethylene-1-(4-iodo-phenyl)-pyrazolidine-3,5-dione,
1-(4-Iodo-phenyl)-4-(5-nitro-thiophen-2-ylmethylene)-pyrazolidine-3,5-dione,
4-(5-Hydroxymethyl-furan-2-ylmethylene)-1-(3-trifluoromethyl-phenyl)-pyrazolidine-3,5-dione,
4-Furan-3-ylmethylene-1-(3-trifluoromethyl-phenyl)-pyrazolidine-3,5-dione,
4-(5-Nitro-thiophen-2-ylmethylene)-1-(3-trifluoromethyl-phenyl)-pyrazolidine-3,5-dione,
1-(4-Iodo-phenyl)-4-(5-nitro-furan-2-ylmethylene)-pyrazolidine-3,5-dione,
1-(4-Iodo-phenyl)-4-[5-(3-nitro-phenyl)-furan-2-ylmethylene]-pyrazolidine-3,5-dione,
4-(4,5-Dimethyl-furan-2-ylmethylene)-1-(4-iodo-phenyl)-pyrazolidine-3,5-dione,
5-[1-(4-Iodo-phenyl)-3,5-dioxo-pyrazolidin-4-ylidenemethyl]-furan-2-sulfonic acid,
4-[1-(4-Iodo-phenyl)-3,5-dioxo-pyrazolidin-4-ylidenemethyl]-benzonitrile,
1-(4-Iodo-phenyl)-4-(3-methyl-thiophen-2-ylmethylene)-pyrazolidine-3,5-dione,
4-(4-Bromo-thiophen-2-ylmethylene)-1-(4-iodo-phenyl)-pyrazolidine-3,5-dione,
1-(4-Iodo-phenyl)-4-(5-methyl-thiophen-2-ylmethylene)-pyrazolidine-3,5-dione,
4-Benzo[b]thiophen-2-ylmethylene-1-(4-iodo-phenyl)-pyrazolidine-3,5-dione,
1-(4-Iodo-phenyl)-4-(4-nitro-thiophen-2-ylmethylene)-pyrazolidine-3,5-dione,
5-[1-(4-Iodo-phenyl)-3,5-dioxo-pyrazolidin-4-ylidenemethyl]-thiophene-3-carboxylic acid,
4-[1-(4-Iodo-phenyl)-3,5-dioxo-pyrazolidin-4-ylidenemethyl]-thiophene-3-carboxylic acid,
2-[3,5-Dioxo-1-(3-trifluoromethyl-phenyl)-pyrazolidin-4-ylidenemethyl]-thiophene-3-carboxylic acid,
4-(4-Nitro-thiophen-2-ylmethylene)-1-(3-trifluoromethyl-phenyl)-pyrazolidine-3,5-dione,
4-[3,5-Dioxo-1-(3-trifluoromethyl-phenyl)-pyrazolidin-4-ylidenemethyl]-thiophene-3-carboxylic acid,
2-[1-(4-Iodo-phenyl)-3,5-dioxo-pyrazolidin-4-ylidenemethyl]-thiophene-3-carboxylic acid,
{3-[1-(4-Iodo-phenyl)-3,5-dioxo-pyrazolidin-4-ylidenemethyl]-thiophen-2-ylsulfanyl}-acetic acid,
4-(4-Hydroxymethyl-furan-3-ylmethylene)-1-(3-trifluoromethyl-phenyl)-pyrazolidine-3,5-dione,
4-benzo[b]thiophen-2-ylmethylene-1-(3-trifluoromethyl-phenyl)-pyrazolidine-3,5-dione,
5-[3,5-Dioxo-1-(3-trifluoromethyl-phenyl)-pyrazolidin-4-ylidenemethyl]-thiophene-3-carboxylic acid,
5-[1-(4-Iodo-phenyl)-3,5-dioxo-pyrazolidin-4-ylidenemethyl]-furan-2-carboxylic acid,
5-(1-Biphenyl-4-yl-3,5-dioxo-pyrazolidin-4-ylidenemethyl]-furan-2-carboxylic acid,
4-(4-Hydroxy-naphthalen-1-ylmethylene)-1-(4-iodo-phenyl)-pyrazolidine-3,5-dione,
1-(4-Iodo-phenyl)-4-(1-oxy-pyridin-4-ylmethylene)-pyrazolidine-3,5-dione,
2-(4-Furan-2-ylmethylene-3,5-dioxo-pyrazolidin-1-yl)-5-iodo-benzoic acid methyl ester,
4-(1H-Indol-5-ylmethylene)-1-(4-iodo-phenyl)-pyrazolidine-3,5-dione,
4-(4-Hydroxymethyl-furan-3-ylmethylene)-1-(4-iodo-phenyl)-pyrazolidine-3,5-dione, 1-(4-Iodophenyl)-4-(1H-pyrrol-2-ylmethylene)-pyrazolidine-3,5-dione,
1-(4-Iodophenyl)-4-(1-methyl-1H-pyrrol-2-ylmethylene)-pyrazolidine-3,5-dione,
1-(4-Iodo-phenyl)-4-[1-(2-nitro-benzyl)-1H-pyrrol-2-ylmethylene]-pyrazolidine-3,5-dione,
1-(4-Iodo-phenyl-4-(1H-pyrazol-3-ylmethylene)-pyrazolidine-3,5-dione,
1-(4-Iodo-phenyl-4-(1H-pyrazol-3-ylmethylene)-pyrazolidine-3,5-dione,
4-(2,3-Dihydro-benzofuran-5-ylmethylene)-1-(4-iodo-phenyl)-pyrazolidine-3,5-dione,
1-(4-Iodo-phenyl)-4-quinolin-2-ylmethylene-pyrazolidine-3,5-dione,
1-(4-Iodo-phenyl)-4-quinolin-4-ylmethylene-pyrazolidine-3,5-dione,
4-[3-(2-Hydroxy-ethoxy)-benzylidene]-1-(4-iodo-phenyl)-pyrazolidine-3,5-dione,
1-(4-Iodo-phenyl)-4-(5-naphthalen-2-yl-thiophen-2-ylmethylene)-pyrazolidine-3,5-dione,
3-{5-[1-(4-Iodo-phenyl)-3, 5-dioxo-pyrazolidin-4-ylidenemethyl]-furan-2-yl}-thiophene-2-carboxylic acid methyl ester,
1-(4-Iodo-phenyl)-4-[5-(2-nitro-4-trifluoromethyl-phenyl)-furan-2-ylmethylene]-pyrazolidine-3,5-dione,
4-(5-Chloro-thiophen-2-ylmethylene)-1-(4-iodo-phenyl)-pyrazolidine-3,5-dione,
1-(4-Iodo-phenyl)-4-thiazol-2-ylmethylene-pyrazolidine-3, 5-dione,
1-(4-Iodo-phenyl)-4-(1-methyl-1H-imidazol-2-ylmethylene)-pyrazolidine-3,5-dione,
4-(2-Diethylamino-thiazol-5-ylmethylene)-1-(4-iodo-phenyl)-pyrazolidine-3,5-dione,
4-[2-(4-Benzyl-piperazin-1-yl)-thiazol-5-ylmethylene]-1-(4-iodo-phenyl)-pyrazolidine-3,5-dione,
1-(4-Iodo-phenyl)-4-[2-(4-methoxy-phenoxy)-thiazol-5-ylmethylene]-pyrazolidine-3,5-dione,
4-(9-Ethyl-9H-carbazol-3-ylmethylene)-1-(4-iodo-phenyl)-pyrazolidine-3,5-dione, or 4-Benzo[b]thiophen-3-ylmethylene-1-(4-iodo-phenyl)-pyrazolidine-3,5-dione, or a pharmaceutically acceptable salt thereof, or tautomer thereof.

In some embodiments, the compound in the unit dosage is not:

4-(4-Iodo-benzylidene)-1-(4-iodo-phenyl)-pyrazolidine-3, 5-dione,
4-(Dimethyl-furan-2-ylmethylene)-1-(3-trifluoromethyl-phenyl)-pyrazolidine-3,5-dione,
Acetic acid 5-[1-(4-iodo-phenyl)-3,5-dioxo-pyrazolidin-4-ylidenemethyl]-furan-2-ylmethyl ester,
4-(4-Bromo-furan-2-ylmethylene)-1-(4-iodo-phenyl)-pyrazolidine-3,5-dione,
1-(4-Iodo-phenyl)-4-(5-methyl-furan-2-ylmethylene)-pyrazolidine-3,5-dione,
4-(5-Bromo-furan-2-ylmethylene)-1-(4-iodo-phenyl)-pyrazolidine-3,5-dione,
1-(4-Iodo-phenyl)-4-[5-(2-methoxy-phenyl)-thiophen-2-ylmethylene]-pyrazolidine-3,5-dione,
1-(4-Iodo-phenyl)-4-thiophen-3-ylmethylene-pyrazolidine-3,5-dione,
1-(4-Iodo-phenyl)-4-(5-phenyl-thiophen-2-ylmethylene)-pyrazolidine-3,5-dione,
4-(5-Methyl-furan-2-ylmethylene)-1-(3-trifluoromethyl-phenyl)-pyrazolidine-3,5-dione,
4-Thiophen-2-ylmethylene-1-(3-trifluoromethyl-phenyl)-pyrazolidine-3,5-dione,
4-(4-Bromo-furan-2-ylmethylene)-1-(3-trifluoromethyl-phenyl)-pyrazolidine-3, 5-dione,
Acetic acid 5-[3,5-dioxo-1-(3-trifluoromethyl-phenyl)-pyrazolidin-4-ylidenemethyl]-furan-2-ylmethyl ester,
4-(7-Bromo-8-hydroxy-quinolin-5-ylmethylene)-1-(4-iodo-phenyl)-pyrazolidine-3,5-dione,
1-(4-Iodo-phenyl)-4-[5-(4-nitro-phenyl)-furan-2-ylmethylene]-pyrazolidine-3,5-dione,
1-(4-Iodo-phenyl)-4-[5-(2-nitro-phenyl)-furan-2-ylmethylene]-pyrazolidine-3,5-dione,
4-(5-Hydroxymethyl-furan-2-ylmethylene)-1-(4-iodo-phenyl)-pyrazolidine-3,5-dione,
1-(4-Iodo-phenyl)-4-(5-nitro-thiophen-2-ylmethylene)-pyrazolidine-3,5-dione,
4-(5-Hydroxymethyl-furan-2-ylmethylene)-1-(3-trifluoromethyl-phenyl)-pyrazolidine-3,5-dione,
4-(5-Nitro-thiophen-2-ylmethylene)-1-(3-trifluoromethyl-phenyl)-pyrazolidine-3,5-dione,
1-(4-Iodo-phenyl)-4-(5-nitro-furan-2-ylmethylene)-pyrazolidine-3,5-dione,
4-(4,5-Dimethyl-furan-2-ylmethylene)-1-(4-iodo-phenyl)-pyrazolidine-3,5-dione,
5-[1-(4-Iodo-phenyl)-3,5-dioxo-pyrazolidin-4-ylidenemethyl]-furan-2-sulfonic acid,
4-[1-(4-Iodo-phenyl)-3,5-dioxo-pyrazolidin-4-ylidenemethyl]-benzonitrile,
1-(4-Iodo-phenyl)-4-(3-methyl-thiophen-2-ylmethylene)-pyrazolidine-3,5-dione,
4-(4-Bromo-thiophen-2-ylmethylene)-1-(4-iodo-phenyl)-pyrazolidine-3,5-dione,
1-(4-Iodo-phenyl)-4-(5-methyl-thiophen-2-ylmethylene)-pyrazolidine-3,5-dione,
4-Benzo[b]thiophen-2-ylmethylene-1-(4-iodo-phenyl)-pyrazolidine-3,5-dione,
1-(4-Iodo-phenyl)-4-(4-nitro-thiophen-2-ylmethylene)-pyrazolidine-3,5-dione,
5-[1-(4-Iodo-phenyl)-3,5-dioxo-pyrazolidin-4-ylidenemethyl]-thiophene-3-carboxylic acid,
4-[1-(4-Iodo-phenyl)-3,5-dioxo-pyrazolidin-4-ylidenemethyl]-thiophene-3-carboxylic acid,
2-[3,5-Dioxo-1-(3-trifluoromethyl-phenyl)-pyrazolidin-4-ylidenemethyl]-thiophene-3-carboxylic acid,
4-(4-Nitro-thiophen-2-ylmethylene)-1-(3-trifluoromethyl-phenyl)-pyrazolidine-3,5-dione,
4-[3,5-Dioxo-1-(3-trifluoromethyl-phenyl)-pyrazolidin-4-ylidenemethyl]-thiophene-3-carboxylic acid,
{3-[3,5-Dioxo-1-(3-trifluoromethyl-phenyl)-pyrazolidin-4-ylidenemethyl]-thiophen-2-ylsulfanyl-acetic acid,
2-[1-(4-Iodo-phenyl)-3,5-dioxo-pyrazolidin-4-ylidenemethyl]-thiophene-3-carboxylic acid,
4-(4-Hydroxymethyl-furan-3-ylmethylene)-1-(3-trifluoromethyl-phenyl)-pyrazolidine-3,5-dione,
4-benzo[b]thiophen-2-ylmethylene-1-(3-trifluoromethyl-phenyl)-pyrazolidine-3,5-dione,
5-[3,5-Dioxo-1-(3-trifluoromethyl-phenyl)-pyrazolidin-4-ylidenemethyl]-thiophene-3-carboxylic acid,
5-[1-(4-Iodo-phenyl)-3,5-dioxo-pyrazolidin-4-ylidenemethyl]-furan-2-carboxylic acid,
5-(1-Biphenyl-4-yl-3,5-dioxo-pyrazolidin-4-ylidenemethyl]-furan-2-carboxylic acid,
4-(4-Hydroxy-naphthalen-1-ylmethylene)-1-(4-iodo-phenyl)-pyrazolidine-3,5-dione,
1-(4-Iodo-phenyl)-4-(1-oxy-pyridin-4-ylmethylene)-pyrazolidine-3,5-dione,
4-(1H-Indol-5-ylmethylene)-1-(4-iodo-phenyl)-pyrazolidine-3,5-dione, 4-(4-Hydroxymethyl-furan-3-ylmethylene)-1-(4-iodo-phenyl)-pyrazolidine-3, 5-dione,
1-(4-Iodophenyl)-4-(1H-pyrrol-2-ylmethylene)-pyrazolidine-3,5-dione,
1-(4-Iodophenyl)-4-(1-methyl-1H-pyrrol-2-ylmethylene)-pyrazolidine-3,5-dione,
1-(4-Iodo-phenyl)-4-[1-(2-nitro-benzyl)-1H-pyrrol-2-ylmethylene]-pyrazolidine-3,5-dione,
1-(4-Iodo-phenyl-4-(1H-pyrazol-3-ylmethylene)-pyrazolidine-3,5-dione,
1-(4-Iodo-phenyl-4-(1H-pyrazol-3-ylmethylene)-pyrazolidine-3,5-dione,
4-(2,3-Dihydro-benzofuran-5-ylmethylene)-1-(4-iodo-phenyl)-pyrazolidine-3,5-dione,
1-(4-Iodo-phenyl)-4-quinolin-2-ylmethylene-pyrazolidine-3,5-dione,
1-(4-Iodo-phenyl)-4-quinolin-4-ylmethylene-pyrazolidine-3,5-dione,
4-[3-(2-Hydroxy-ethoxy)-benzylidene]-1-(4-iodo-phenyl)-pyrazolidine-3,5-dione,
1-(4-Iodo-phenyl)-4-(5-naphthalen-2-yl-thiophen-2-ylmethylene)-pyrazolidine-3,5-dione,
3-{5-[1-(4-Iodo-phenyl)-3,5-dioxo-pyrazolidin-4-ylidenemethyl]-furan-2-yl}-thiophene-2-carboxylic acid methyl ester,
4-(5-Chloro-thiophen-2-ylmethylene)-1-(4-iodo-phenyl)-pyrazolidine-3,5-dione,
[1-(4-Iodo-phenyl)-4-thiazol-2-ylmethylene-pyrazolidine-3,5-dione,
1-(4-Iodo-phenyl)-4-(1-methyl-1H-imidazol-2-ylmethylene)-pyrazolidine-3,5-dione,
4-(2-Diethylamino-thiazol-5-ylmethylene)-1-(4-iodo-phenyl)-pyrazolidine-3,5-dione,
4-[2-(4-Benzyl-piperazin-1-yl)-thiazol-5-ylmethylene]-1-(4-iodo-phenyl)-pyrazolidine-3,5-dione,
1-(4-Iodo-phenyl)-4-[2-(4-methoxy-phenoxy)-thiazol-5-ylmethylene]-pyrazolidine-3,5-dione,
4-(9-Ethyl-9H-carbazol-3-ylmethylene)-1-(4-iodo-phenyl)-pyrazolidine-3, 5-dione, or 4-Benzo[b]thiophen-3-ylmethylene-1-(4-iodo-phenyl)-pyrazolidine-3,5-dione:

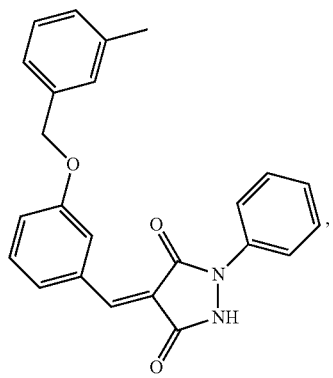 [SMILES: Cc1cccc(COc2cccc(/C=C3/C(=O)NN(c4ccccc4)C3=O)c2)c1]

or a pharmaceutically acceptable salt thereof or tautomer thereof; and $R^1$ is not furanyl or furanyl substituted with optionally substituted aryl.

Some embodiments provide a method of treating breast cancer, leukemia, or lung cancer comprising administering a therapeutically effective amount of a compound as disclosed and described herein to a patient in need thereof. Some embodiments provide a method of treating breast cancer, leukemia, or lung cancer comprising administering a therapeutically effective amount of a unit dosage as disclosed and described herein to a patient in need thereof. In some embodiments, the method further comprises co-administering therapeutically effective amount of a compound having the structure:

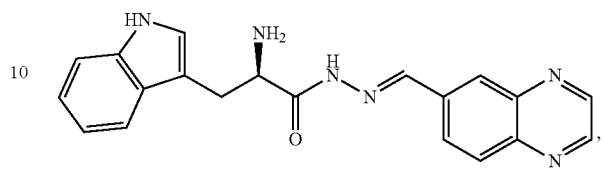

or a pharmaceutically acceptable salt thereof. In some embodiments of the methods, the co-administration is sequential or concurrent. In some embodiments of the methods, the compound of Formula I is:

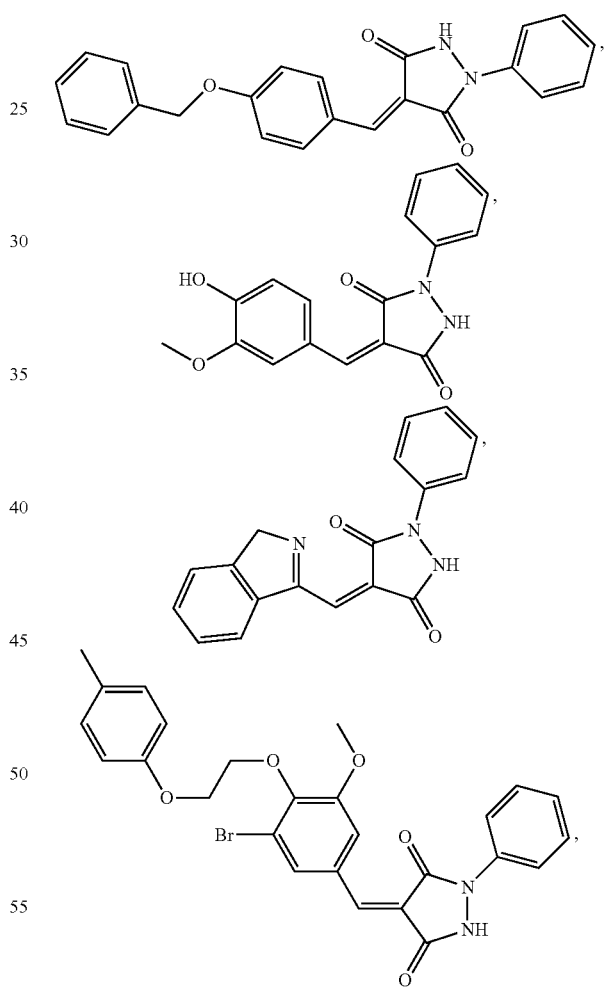

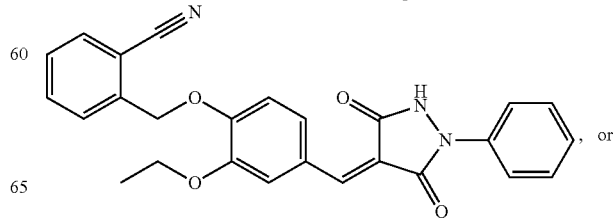

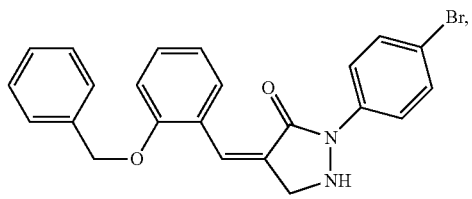

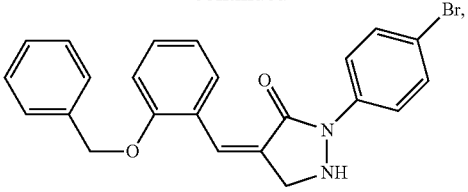

or a pharmaceutically acceptable salt thereof, or tautomer thereof. In some embodiments of the methods, the compound of Formula I is not:

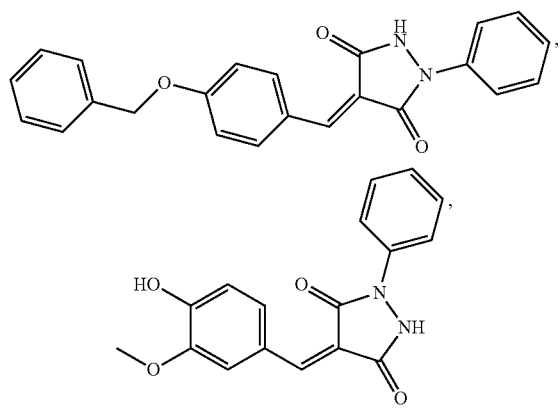

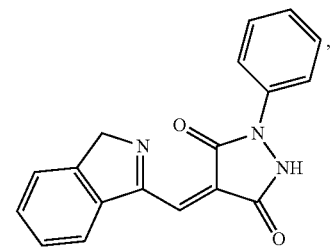

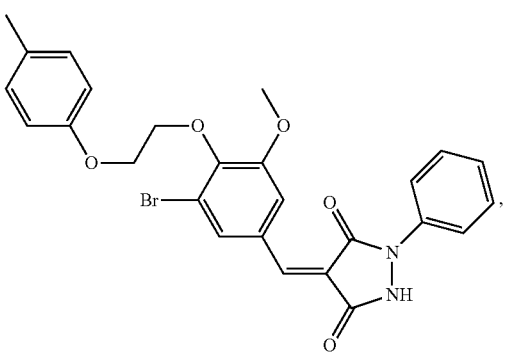

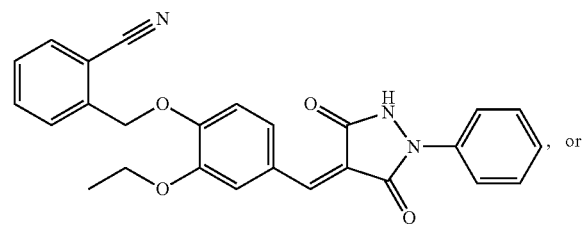

or a pharmaceutically acceptable salt thereof, or tautomer thereof. In some embodiments of the methods, the compound is:
4-(4-Iodo-benzylidene)-1-(4-iodo-phenyl)-pyrazolidine-3,5-dione,
4-(Dimethyl-furan-2-ylmethylene)-1-(3-trifluoromethyl-phenyl)-pyrazolidine-3,5-dione,
1-Biphenyl-4-yl-4-furan-2-ylmethylene-pyrazolidine-3,5-dione,
Acetic acid 5-[1-(4-iodo-phenyl)-3,5-dioxo-pyrazolidin-4-ylidenemethyl]-furan-2-ylmethyl ester,
4-(4-Bromo-furan-2-ylmethylene)-1-(4-iodo-phenyl)-pyrazolidine-3,5-dione,
1-(4-Iodo-phenyl)-4-(5-methyl-furan-2-ylmethylene)-pyrazolidine-3,5-dione,
4-(5-Bromo-furan-2-ylmethylene)-1-(4-iodo-phenyl)-pyrazolidine-3,5-dione,
1-(4-Iodo-phenyl)-4-[5-(2-methoxy-phenyl)-thiophen-2-ylmethylene]-pyrazolidine-3,5-dione,
1-(4-Iodo-phenyl)-4-thiophen-3-ylmethylene-pyrazolidine-3,5-dione,
1-(4-Iodo-phenyl)-4-(5-phenyl-thiophen-2-ylmethylene)-pyrazolidine-3,5-dione,
4-Furan-2-ylmethylene-1-(3-trifluoromethyl-phenyl)-pyrazolidine-3,5-dione,
4-(5-Methyl-furan-2-ylmethylene)-1-(3-trifluoromethyl-phenyl)-pyrazolidine-3,5-dione,
4-Thiophen-2-ylmethylene-1-(3-trifluoromethyl-phenyl)-pyrazolidine-3,5-dione,
4-(4-Bromo-furan-2-ylmethylene)-1-(3-trifluoromethyl-phenyl)-pyrazolidine-3,5-dione,
Acetic acid 5-[3,5-dioxo-1-(3-trifluoromethyl-phenyl)-pyrazolidin-4-ylidenemethyl]-furan-2-ylmethyl ester,
1-(3-Chloro-4-methyl-phenyl)-4-furan-2-ylmethylene-pyrazolidine-3,5-dione,
4-(7-Bromo-8-hydroxy-quinolin-5-ylmethylene)-1-(4-iodo-phenyl)-pyrazolidine-3, 5-dione,
1-(4-Iodo-phenyl)-4-[5-(4-nitro-phenyl)-furan-2-ylmethylene]-pyrazolidine-3,5-dione,
1-(4-Iodo-phenyl)-4-[5-(2-nitro-phenyl)-furan-2-ylmethylene]-pyrazolidine-3,5-dione,
4-(5-Hydroxymethyl-furan-2-ylmethylene)-1-(4-iodo-phenyl)-pyrazolidine-3,5-dione,
4-Furan-3-ylmethylene-1-(4-iodo-phenyl)-pyrazolidine-3, 5-dione,
1-(4-Iodo-phenyl)-4-(5-nitro-thiophen-2-ylmethylene)-pyrazolidine-3,5-dione,
4-(5-Hydroxymethyl-furan-2-ylmethylene)-1-(3-trifluoromethyl-phenyl)-pyrazolidine-3,5-dione,
4-Furan-3-ylmethylene-1-(3-trifluoromethyl-phenyl)-pyrazolidine-3,5-dione,
4-(5-Nitro-thiophen-2-ylmethylene)-1-(3-trifluoromethyl-phenyl)-pyrazolidine-3,5-dione,
1-(4-Iodo-phenyl)-4-(5-nitro-furan-2-ylmethylene)-pyrazolidine-3,5-dione,
1-(4-Iodo-phenyl)-4-[5-(3-nitro-phenyl)-furan-2-ylmethylene]-pyrazolidine-3,5-dione, 4-(4,5-Dimethyl-furan-2-ylmethylene)-1-(4-iodo-phenyl)-pyrazolidine-3,5-dione,
5-[1-(4-Iodo-phenyl)-3,5-dioxo-pyrazolidin-4-ylidenemethyl]-furan-2-sulfonic acid,
4-[1-(4-Iodo-phenyl)-3,5-dioxo-pyrazolidin-4-ylidenemethyl]-benzonitrile,
1-(4-Iodo-phenyl)-4-(3-methyl-thiophen-2-ylmethylene)-pyrazolidine-3,5-dione,
4-(4-Bromo-thiophen-2-ylmethylene)-1-(4-iodo-phenyl)-pyrazolidine-3,5-dione,
1-(4-Iodo-phenyl)-4-(5-methyl-thiophen-2-ylmethylene)-pyrazolidine-3,5-dione,
4-Benzo[b]thiophen-2-ylmethylene-1-(4-iodo-phenyl)-pyrazolidine-3,5-dione,
1-(4-Iodo-phenyl)-4-(4-nitro-thiophen-2-ylmethylene)-pyrazolidine-3,5-dione,
5-[1-(4-Iodo-phenyl)-3,5-dioxo-pyrazolidin-4-ylidenemethyl]-thiophene-3-carboxylic acid,
4-[1-(4-Iodo-phenyl)-3,5-dioxo-pyrazolidin-4-ylidenemethyl]-thiophene-3-carboxylic acid,
2-[3,5-Dioxo-1-(3-trifluoromethyl-phenyl)-pyrazolidin-4-ylidenemethyl]-thiophene-3-carboxylic acid,
4-(4-Nitro-thiophen-2-ylmethylene)-1-(3-trifluoromethyl-phenyl)-pyrazolidine-3,5-dione,
4-[3,5-Dioxo-1-(3-trifluoromethyl-phenyl)-pyrazolidin-4-ylidenemethyl]-thiophene-3-carboxylic acid,
2-[1-(4-Iodo-phenyl)-3,5-dioxo-pyrazolidin-4-ylidenemethyl]-thiophene-3-carboxylic acid,
{3-[1-(4-Iodo-phenyl)-3,5-dioxo-pyrazolidin-4-ylidenemethyl]-thiophen-2-ylsulfanyl}-acetic acid,
4-(4-Hydroxymethyl-furan-3-ylmethylene)-1-(3-trifluoromethyl-phenyl)-pyrazolidine-3,5-dione,
4-benzo[b]thiophen-2-ylmethylene-1-(3-trifluoromethyl-phenyl)-pyrazolidine-3,5-dione,
5-[3,5-Dioxo-1-(3-trifluoromethyl-phenyl)-pyrazolidin-4-ylidenemethyl]-thiophene-3-carboxylic acid,
5-[1-(4-Iodo-phenyl)-3,5-dioxo-pyrazolidin-4-ylidenemethyl]-furan-2-carboxylic acid,
5-(1-Biphenyl-4-yl-3,5-dioxo-pyrazolidin-4-ylidenemethyl)-furan-2-carboxylic acid,
4-(4-Hydroxy-naphthalen-1-ylmethylene)-1-(4-iodo-phenyl)-pyrazolidine-3,5-dione,
1-(4-Iodo-phenyl)-4-(1-oxy-pyridin-4-ylmethylene)-pyrazolidine-3,5-dione,
2-(4-Furan-2-ylmethylene-3,5-dioxo-pyrazolidin-1-yl)-5-iodo-benzoic acid methyl ester,
4-(1H-Indol-5-ylmethylene)-1-(4-iodo-phenyl)-pyrazolidine-3,5-dione,
4-(4-Hydroxymethyl-furan-3-ylmethylene)-1-(4-iodo-phenyl)-pyrazolidine-3,5-dione,
1-(4-Iodophenyl)-4-(1H-pyrrol-2-ylmethylene)-pyrazolidine-3,5-dione,
1-(4-Iodophenyl)-4-(1-methyl-1H-pyrrol-2-ylmethylene)-pyrazolidine-3,5-dione,
1-(4-Iodo-phenyl)-4-[1-(2-nitro-benzyl)-1H-pyrrol-2-ylmethylene]-pyrazolidine-3,5-dione,
1-(4-Iodo-phenyl-4-(1H-pyrazol-3-ylmethylene)-pyrazolidine-3,5-dione,
1-(4-Iodo-phenyl-4-(1H-pyrazol-3-ylmethylene)-pyrazolidine-3,5-dione,
4-(2,3-Dihydro-benzofuran-5-ylmethylene)-1-(4-iodo-phenyl)-pyrazolidine-3,5-dione,
1-(4-Iodo-phenyl)-4-quinolin-2-ylmethylene-pyrazolidine-3,5-dione,
1-(4-Iodo-phenyl)-4-quinolin-4-ylmethylene-pyrazolidine-3,5-dione,
4-[3-(2-Hydroxy-ethoxy)-benzylidene]-1-(4-iodo-phenyl)-pyrazolidine-3,5-dione,
1-(4-Iodo-phenyl)-4-(5-naphthalen-2-yl-thiophen-2-ylmethylene)-pyrazolidine-3,5-dione,
3-{5-[1-(4-Iodo-phenyl)-3,5-dioxo-pyrazolidin-4-ylidenemethyl]-furan-2-yl}-thiophene-2-carboxylic acid methyl ester,
1-(4-Iodo-phenyl)-4-[5-(2-nitro-4-trifluoromethyl-phenyl)-furan-2-ylmethylene]-pyrazolidine-3,5-dione,
4-(5-Chloro-thiophen-2-ylmethylene)-1-(4-iodo-phenyl)-pyrazolidine-3,5-dione,
1-(4-Iodo-phenyl)-4-thiazol-2-ylmethylene-pyrazolidine-3,5-dione,
1-(4-Iodo-phenyl)-4-(1-methyl-1H-imidazol-2-ylmethylene)-pyrazolidine-3,5-dione,
4-(2-Diethylamino-thiazol-5-ylmethylene)-1-(4-iodo-phenyl)-pyrazolidine-3,5-dione,
4-[2-(4-Benzyl-piperazin-1-yl)-thiazol-5-ylmethylene]-1-(4-iodo-phenyl)-pyrazolidine-3,5-dione,
1-(4-Iodo-phenyl)-4-[2-(4-methoxy-phenoxy)-thiazol-5-ylmethylene]-pyrazolidine-3,5-dione,
4-(9-Ethyl-9H-carbazol-3-ylmethylene)-1-(4-iodo-phenyl)-pyrazolidine-3,5-dione, or 4-Benzo[b]thiophen-3-ylmethylene-1-(4-iodo-phenyl)-pyrazolidine-3,5-dione, or a pharmaceutically acceptable salt thereof, or tautomer thereof.

Some embodiments provide a method of evaluating a compound for inhibition of Rho GTPase activation comprising contacting a RGS domain-containing RhoGEF with a compound having the structure of Formula I:

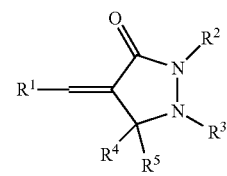

or a pharmaceutically acceptable salt thereof, or tautomer thereof,
wherein:
$R^1$ is aryl, heteroaryl, or heterocyclyl, each optionally substituted with one or more $R^{1A}$;
each $R^{1A}$ is independently selected from the group consisting of hydroxy, halo, cyano, nitro, —SO$_2$OH, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;
each $R^{1B}$ is independently selected from the group consisting of —OR$^{1C}$, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is H (hydrogen), aryl, or heteroaryl, said aryl or heteroaryl each optionally substituted with one or more $R^{2A}$;

each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);

each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^4$ is H (hydrogen), or $C_{1-6}$ alkyl; and $R^5$ is H (hydrogen), or $C_{1-6}$ alkyl, or optionally $R^4$ and $R^5$ together are oxo.

Some embodiments provide a method of inhibiting Rho GTPase activation comprising contacting a RGS domain-containing RhoGEF with a compound having the structure of Formula I:

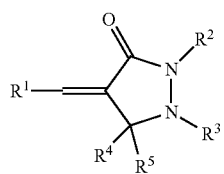

I or a pharmaceutically acceptable salt thereof,
wherein:

$R^1$ is aryl, heteroaryl, or heterocyclyl, each optionally substituted with one or more $R^{1A}$;

each $R^{1A}$ is independently selected from the group consisting of hydroxy, halo, cyano, nitro, —$SO_2OH$, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 $R^{1B}$, and $C_{1-6}$ alkoxy optionally substituted with up to 5 $R^{1B}$;

each $R^{1B}$ is independently selected from the group consisting of —$OR^{1C}$, aryl, and heteroaryl, said aryl or heteroaryl each optionally substituted with one or more $R^{1D}$;

each $R^{1C}$ is independently selected from the group consisting of aryl, and heteroaryl, said aryl or heteroaryl each optionally substituted with one or more $R^{1E}$;

each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is H (hydrogen), aryl, or heteroaryl, said aryl or heteroaryl each optionally substituted with one or more $R^{2A}$;

each $R^{2A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^3$ is H (hydrogen), aryl, or heteroaryl, said aryl or heteroaryl each optionally substituted with one or more $R^{3A}$, provided that one of $R^2$ and $R^3$ is H (hydrogen) and one of $R^2$ and $R^3$ is not H (hydrogen);

each $R^{3A}$ is independently selected from the group consisting of hydroxy, halo, cyano, nitro, O-carbamyl, N-carbamyl, C-amido, N-amido, C-carboxy, O-carboxy, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^4$ is H (hydrogen), or $C_{1-6}$ alkyl; and $R^5$ is H (hydrogen), or $C_{1-6}$ alkyl, or optionally $R^4$ and $R^5$ together are oxo.

Some embodiments provide method of inhibiting Rho GTPase activation comprising contacting a RGS domain-containing RhoGEF with:

4-(4-Iodo-benzylidene)-1-(4-iodo-phenyl)-pyrazolidine-3,5-dione, 4-(Dimethyl-furan-2-ylmethylene)-1-(3-trifluoromethyl-phenyl)-pyrazolidine-3,5-dione, 1-Biphenyl-4-yl-4-furan-2-ylmethylene-pyrazolidine-3,5-dione, Acetic acid 5-[1-(4-iodo-phenyl)-3,5-dioxo-pyrazolidin-4-ylidenemethyl]-furan-2-ylmethyl ester, 4-(4-Bromo-furan-2-ylmethylene)-1-(4-iodo-phenyl)-pyrazolidine-3,5-dione, 1-(4-Iodo-phenyl)-4-(5-methyl-furan-2-ylmethylene)-pyrazolidine-3,5-dione, 4-(5-Bromo-furan-2-ylmethylene)-1-(4-iodo-phenyl)-pyrazolidine-3,5-dione, 1-(4-Iodo-phenyl)-4-[5-(2-methoxy-phenyl)-thiophen-2-yl-methylene]-pyrazolidine-3,5-dione,
1-(4-Iodo-phenyl)-4-thiophen-3-ylmethylene-pyrazolidine-3,5-dione,
1-(4-Iodo-phenyl)-4-(5-phenyl-thiophen-2-ylmethylene)-pyrazolidine-3,5-dione,
4-Furan-2-ylmethylene-1-(3-trifluoromethyl-phenyl)-pyrazolidine-3,5-dione,
4-(5-Methyl-furan-2-ylmethylene)-1-(3-trifluoromethyl-phenyl)-pyrazolidine-3,5-dione,
4-Thiophen-2-ylmethylene-1-(3-trifluoromethyl-phenyl)-pyrazolidine-3,5-dione,
4-(4-Bromo-furan-2-ylmethylene)-1-(3-trifluoromethyl-phenyl)-pyrazolidine-3,5-dione,
Acetic acid 5-[3,5-dioxo-1-(3-trifluoromethyl-phenyl)-pyrazolidin-4-ylidenemethyl]-furan-2-ylmethyl ester,
1-(3-Chloro-4-methyl-phenyl)-4-furan-2-ylmethylene-pyrazolidine-3,5-dione,
4-(7-Bromo-8-hydroxy-quinolin-5-ylmethylene)-1-(4-iodo-phenyl)-pyrazolidine-3, 5-dione,
1-(4-Iodo-phenyl)-4-[5-(4-nitro-phenyl)-furan-2-ylmethylene]-pyrazolidine-3,5-dione,
1-(4-Iodo-phenyl)-4-[5-(2-nitro-phenyl)-furan-2-ylmethylene]-pyrazolidine-3,5-dione,
4-(5-Hydroxymethyl-furan-2-ylmethylene)-1-(4-iodo-phenyl)-pyrazolidine-3,5-dione,
4-Furan-3-ylmethylene-1-(4-iodo-phenyl)-pyrazolidine-3, 5-dione,
1-(4-Iodo-phenyl)-4-(5-nitro-thiophen-2-ylmethylene)-pyrazolidine-3,5-dione,
4-(5-Hydroxymethyl-furan-2-ylmethylene)-1-(3-trifluoromethyl-phenyl)-pyrazolidine-3,5-dione,
4-Furan-3-ylmethylene-1-(3-trifluoromethyl-phenyl)-pyrazolidine-3,5-dione,
4-(5-Nitro-thiophen-2-ylmethylene)-1-(3-trifluoromethyl-phenyl)-pyrazolidine-3,5-dione,
1-(4-Iodo-phenyl)-4-(5-nitro-furan-2-ylmethylene)-pyrazolidine-3,5-dione,
1-(4-Iodo-phenyl)-4-[5-(3-nitro-phenyl)-furan-2-ylmethylene]-pyrazolidine-3,5-dione,
4-(4,5-Dimethyl-furan-2-ylmethylene)-1-(4-iodo-phenyl)-pyrazolidine-3,5-dione,
5-[1-(4-Iodo-phenyl)-3,5-dioxo-pyrazolidin-4-ylidenemethyl]-furan-2-sulfonic acid,
4-[1-(4-Iodo-phenyl)-3,5-dioxo-pyrazolidin-4-ylidenemethyl]-benzonitrile,
1-(4-Iodo-phenyl)-4-(3-methyl-thiophen-2-ylmethylene)-pyrazolidine-3,5-dione,
4-(4-Bromo-thiophen-2-ylmethylene)-1-(4-iodo-phenyl)-pyrazolidine-3,5-dione,
1-(4-Iodo-phenyl)-4-(5-methyl-thiophen-2-ylmethylene)-pyrazolidine-3,5-dione,
4-Benzo[b]thiophen-2-ylmethylene-1-(4-iodo-phenyl)-pyrazolidine-3,5-dione,
1-(4-Iodo-phenyl)-4-(4-nitro-thiophen-2-ylmethylene)-pyrazolidine-3,5-dione,
5-[1-(4-Iodo-phenyl)-3,5-dioxo-pyrazolidin-4-ylidenemethyl]-thiophene-3-carboxylic acid,
4-[1-(4-Iodo-phenyl)-3,5-dioxo-pyrazolidin-4-ylidenemethyl]-thiophene-3-carboxylic acid,
2-[3,5-Dioxo-1-(3-trifluoromethyl-phenyl)-pyrazolidin-4-ylidenemethyl]-thiophene-3-carboxylic acid,
4-(4-Nitro-thiophen-2-ylmethylene)-1-(3-trifluoromethyl-phenyl)-pyrazolidine-3,5-dione,
4-[3,5-Dioxo-1-(3-trifluoromethyl-phenyl)-pyrazolidin-4-ylidenemethyl]-thiophene-3-carboxylic acid,
2-[1-(4-Iodo-phenyl)-3,5-dioxo-pyrazolidin-4-ylidenemethyl]-thiophene-3-carboxylic acid,
{3-[1-(4-Iodo-phenyl)-3,5-dioxo-pyrazolidin-4-ylidenemethyl]-thiophen-2-ylsulfanyl}-acetic acid,
4-(4-Hydroxymethyl-furan-3-ylmethylene)-1-(3-trifluoromethyl-phenyl)-pyrazolidine-3,5-dione,
4-benzo[b]thiophen-2-ylmethylene-1-(3-trifluoromethyl-phenyl)-pyrazolidine-3,5-dione,
5-[3,5-Dioxo-1-(3-trifluoromethyl-phenyl)-pyrazolidin-4-ylidenemethyl]-thiophene-3-carboxylic acid,
5-[1-(4-Iodo-phenyl)-3,5-dioxo-pyrazolidin-4-ylidenemethyl]-furan-2-carboxylic acid,
5-(1-Biphenyl-4-yl-3,5-dioxo-pyrazolidin-4-ylidenemethyl]-furan-2-carboxylic acid,
4-(4-Hydroxy-naphthalen-1-ylmethylene)-1-(4-iodo-phenyl)-pyrazolidine-3,5-dione,
1-(4-Iodo-phenyl)-4-(1-oxy-pyridin-4-ylmethylene)-pyrazolidine-3,5-dione,
2-(4-Furan-2-ylmethylene-3,5-dioxo-pyrazolidin-1-yl)-5-iodo-benzoic acid methyl ester,
4-(1H-Indol-5-ylmethylene)-1-(4-iodo-phenyl)-pyrazolidine-3,5-dione,
4-(4-Hydroxymethyl-furan-3-ylmethylene)-1-(4-iodo-phenyl)-pyrazolidine-3,5-dione,
1-(4-Iodophenyl)-4-(1H-pyrrol-2-ylmethylene)-pyrazolidine-3,5-dione,
1-(4-Iodophenyl)-4-(1-methyl-1H-pyrrol-2-ylmethylene)-pyrazolidine-3,5-dione,
1-(4-Iodo-phenyl)-4-[1-(2-nitro-benzyl)-1H-pyrrol-2-ylmethylene]-pyrazolidine-3,5-dione,
1-(4-Iodo-phenyl-4-(1H-pyrazol-3-ylmethylene)-pyrazolidine-3,5-dione,
1-(4-Iodo-phenyl)-4-(1H-pyrazol-3-ylmethylene)-pyrazolidine-3,5-dione,
4-(2,3-Dihydro-benzofuran-5-ylmethylene)-1-(4-iodo-phenyl)-pyrazolidine-3,5-dione,
1-(4-Iodo-phenyl)-4-quinolin-2-ylmethylene-pyrazolidine-3,5-dione,
1-(4-Iodo-phenyl)-4-quinolin-4-ylmethylene-pyrazolidine-3,5-dione,
4-[3-(2-Hydroxy-ethoxy)-benzylidene]-1-(4-iodo-phenyl)-pyrazolidine-3,5-dione,
1-(4-Iodo-phenyl)-4-(5-naphthalen-2-yl-thiophen-2-ylmethylene)-pyrazolidine-3,5-dione,
3-{5-[1-(4-Iodo-phenyl)-3,5-dioxo-pyrazolidin-4-ylidenemethyl]-furan-2-yl}-thiophene-2-carboxylic acid methyl ester,
1-(4-Iodo-phenyl)-4-[5-(2-nitro-4-trifluoromethyl-phenyl)-furan-2-ylmethylene]-pyrazolidine-3,5-dione,
4-(5-Chloro-thiophen-2-ylmethylene)-1-(4-iodo-phenyl)-pyrazolidine-3,5-dione,
1-(4-Iodo-phenyl)-4-thiazol-2-ylmethylene-pyrazolidine-3, 5-dione,
1-(4-Iodo-phenyl)-4-(1-methyl-1H-imidazol-2-ylmethylene)-pyrazolidine-3,5-dione,
4-(2-Diethylamino-thiazol-5-ylmethylene)-1-(4-iodo-phenyl)-pyrazolidine-3,5-dione,
4-[2-(4-Benzyl-piperazin-1-yl)-thiazol-5-ylmethylene]-1-(4-iodo-phenyl)-pyrazolidine-3,5-dione,
1-(4-Iodo-phenyl)-4-[2-(4-methoxy-phenoxy)-thiazol-5-ylmethylene]-pyrazolidine-3,5-dione,
4-(9-Ethyl-9H-carbazol-3-ylmethylene)-1-(4-iodo-phenyl)-pyrazolidine-3,5-dione, or 4-Benzo[b]thiophen-3-ylmethylene-1-(4-iodo-phenyl)-pyrazolidine-3,5-dione, or a pharmaceutically acceptable salt thereof or tautomer thereof.

Some embodiments provide a method of evaluating inhibition of Rho GTPase activation property of a compound comprising:
(a) contacting a solution comprising RhoGEF and fluorescent GDP-containing reagent-bound Rho GTPase with the compound and measuring decrease in fluorescence over time; and
(b) contacting a solution containing RGS domain-containing RhoGEF, GDP-bound Rho GTPase and fluorescent GTP containing reagent contacting with the compound and measuring increase in fluorescence over time,
wherein the Rho GTPase inhibitory activity of the compound is indicated by a combination of: a reduction in the rate of decrease of fluorescence in step (a) relative to step (a) performed in the absence of the compound; and a reduction in the rate of increase of fluorescence in step (b) relative to step (b) performed in the absence of the compound.

In some embodiments, $R^2$ is H (hydrogen). In some embodiments, $R^3$ is H (hydrogen). In some embodiments, $R^2$ is phenyl optionally substituted with one or more $R^{2A}$; and each $R^{2A}$ is independently selected from the group consisting of halo, $C_{1-6}$ alkyl optionally substituted with up to 5 fluoro, and $C_{1-6}$ alkoxy optionally substituted with up to 5 fluoro. In some embodiments, $R^2$ is

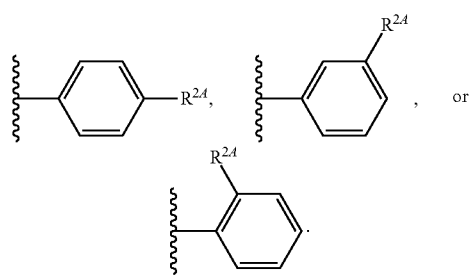

In some embodiments, $R^{2A}$ is fluoro, chloro, bromo, iodo, methyl, ethyl, methoxy, ethoxy, trifluoromethyl, or trifluoromethoxy. In some embodiments, $R^3$ is phenyl optionally substituted with one or more $R^{3A}$; and each $R^{3A}$ is independently selected from the group consisting of halo, $C_{1-6}$ alkyl optionally substituted with up to 5 fluoro, and $C_{1-6}$ alkoxy optionally substituted with up to 5 fluoro. In some embodiments, $R^3$ is

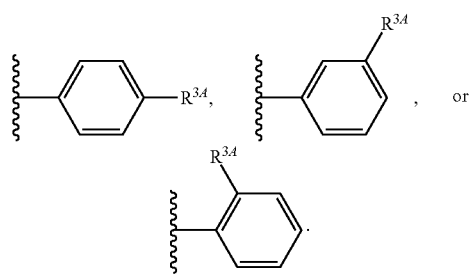

In some embodiments, $R^{3A}$ is fluoro, chloro, bromo, iodo, methyl, ethyl, methoxy, ethoxy, trifluoromethyl, or trifluoromethoxy. In some embodiments, $R^1$ is phenyl or heterocyclyl, each optionally substituted with one or more $R^{1A}$; each $R^{1A}$ is independently selected from the group consisting of hydroxy, halo, cyano, amino, $C_{1-6}$ alkyl, $C_{1-6}$ alkyl substituted with $R^{1B}$, $C_{1-4}$ alkoxy, and $C_{1-4}$ alkoxy substituted with $R^{1B}$; each $R^{1B}$ is independently selected from the group consisting of —$OR^{1C}$, phenyl, and heteroaryl, said phenyl optionally substituted with one or more $R^{1D}$; each $R^{1C}$ is independently selected from the group consisting of phenyl, and heteroaryl, said phenyl or heteroaryl each optionally substituted with one or more $R^{1E}$; each $R^{1D}$ is independently selected from the group consisting of hydroxy, halo, cyano, amino, $C_{1-3}$ alkyl optionally substituted with up to 5 fluoro, and $C_{1-3}$ alkoxy optionally substituted with up to 5 fluoro; and each $R^{1E}$ is independently selected from the group consisting of hydroxy, halo, cyano, amino, $C_{1-3}$ alkyl optionally substituted with up to 5 fluoro, and $C_{1-3}$ alkoxy optionally substituted with up to 5 fluoro. In some embodiments, $R^1$ is phenyl optionally substituted with one or more $R^{1A}$; each $R^{1A}$ is independently selected from the group consisting of hydroxy, fluoro, chloro, bromo, $C_{1-3}$ alkyl, Ca-3 alkoxy, and $C_{1-4}$ alkoxy substituted with $R^{1B}$; each $R^{1B}$ is independently selected from the group consisting of —$OR^{1C}$, and phenyl, said phenyl optionally substituted with one or more $R^{1D}$; each $R^{1C}$ is phenyl optionally substituted with one or more $R^{1E}$; each $R^{1D}$ is independently selected from the group consisting of fluoro, chloro, bromo, cyano, $C_{1-3}$ alkyl optionally substituted with up to 5 fluoro, and $C_{1-3}$ alkoxy optionally substituted with up to 5 fluoro; and each $R^{1E}$ is independently selected from the group consisting of fluoro, chloro, bromo, cyano, $C_{1-3}$ alkyl optionally substituted with up to 5 fluoro, and $C_{1-3}$ alkoxy optionally substituted with up to 5 fluoro. In some embodiments, $R^1$ is heteroaryl, or heterocyclyl, each optionally substituted with one or more $R^{1A}$; each $R^{1A}$ is independently selected from the group consisting of hydroxy, halo, cyano, amino, $C_{1-6}$ alkyl, $C_{1-6}$ alkyl substituted with $R^{1B}$, $C_{1-4}$ alkoxy, and $C_{1-4}$ alkoxy substituted with $R^{1B}$; each $R^{1B}$ is independently selected from the group consisting of —$OR^{1C}$, and phenyl, said phenyl optionally substituted with one or more $R^{1D}$; each $R^{1C}$ is independently selected from the group consisting of phenyl, and heteroaryl, said phenyl or heteroaryl each optionally substituted with one or more $R^{1E}$; each $R^{1D}$ is independently selected from the group consisting of hydroxy, halo, cyano, amino, $C_{1-3}$ alkyl optionally substituted with up to 5 fluoro, and $C_{1-3}$ alkoxy optionally substituted with up to 5 fluoro; and each $R^{1E}$ is independently selected from the group consisting of hydroxy, halo, cyano, amino, $C_{1-3}$ alkyl optionally substituted with up to 5 fluoro, and $C_{1-3}$ alkoxy optionally substituted with up to 5 fluoro. In some embodiments, $R^1$ is heterocyclyl optionally substituted with one or more $R^{1A}$; each $R^{1A}$ is independently selected from the group consisting of hydroxy, fluoro, chloro, bromo, $C_{1-3}$ alkyl, Ca-3 alkoxy, and $C_{1-4}$ alkoxy substituted with $R^{1B}$; each $R^{1B}$ is independently selected from the group consisting of —$OR^{1C}$, and phenyl, said phenyl optionally substituted with one or more $R^{1D}$; each $R^{1C}$ is phenyl optionally substituted with one or more $R^{1E}$; each $R^{1D}$ is independently selected from the group consisting of fluoro, chloro, bromo, cyano, $C_{1-3}$ alkyl optionally substituted with up to 5 fluoro, and $C_{1-3}$ alkoxy optionally substituted with up to 5 fluoro; and each $R^{1E}$ is independently selected from the group consisting of fluoro, chloro, bromo, cyano, $C_{1-3}$ alkyl optionally substituted with up to 5 fluoro, and $C_{1-3}$ alkoxy optionally substituted with up to 5 fluoro. In some embodiments, $R^{1A}$ is $C_{1-4}$ alkoxy substituted with $R^{1B}$; and $R^{1B}$ is phenyl optionally substituted with one or more $R^{1D}$In some embodiments, $R^1$ is 1H-isoindolyl. In some embodiments, $R^4$ is H (hydrogen); and $R^5$ is H (hydrogen). In some embodiments, $R^4$ and $R^5$ together are oxo.

In some embodiments, the compound having the structure of Formula I has the structure of Formula Ia, Ib, or Ib:

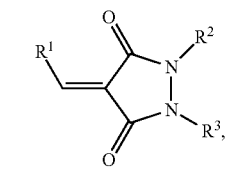

(Ia)

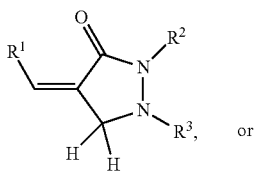

(Ib)

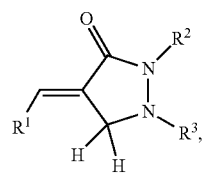

(Ic)

or a pharmaceutically acceptable salt thereof. In some embodiments, $R^1$ is

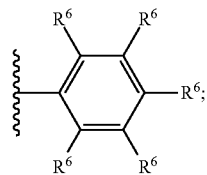

each $R^6$ is independently selected from the group consisting of H (hydrogen), hydroxy, halo, $C_{1-3}$ alkyl, $C_{1-3}$ alkoxy, and $C_{1-4}$ alkoxy substituted with $R^{1B}$; each $R^{1B}$ is independently selected from the group consisting of —$OR^{1C}$, and phenyl, said phenyl optionally substituted with one or more $R^{1D}$; each $R^{1C}$ is phenyl optionally substituted with one or more $R^{1E}$; each $R^{1D}$ is independently selected from the group consisting of fluoro, chloro, bromo, cyano, $C_{1-3}$ alkyl optionally substituted with up to 5 fluoro, and $C_{1-3}$ alkoxy optionally substituted with up to 5 fluoro; and each $R^{1E}$ is independently selected from the group consisting of fluoro, chloro, bromo, cyano, $C_{1-3}$ alkyl optionally substituted with up to 5 fluoro, and $C_{1-3}$ alkoxy optionally substituted with up to 5 fluoro. In some embodiments, $R^1$ is

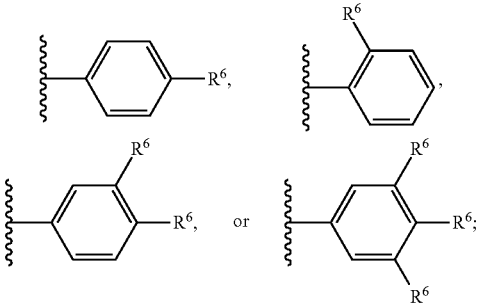

each $R^6$ is independently selected from the group consisting of hydroxy, fluoro, chloro, bromo, methyl, methoxy, ethoxy, and $C_{1-3}$ alkoxy substituted with $R^{1B}$; each $R^{1B}$ is independently selected from the group consisting of —$OR^{1C}$, and phenyl, said phenyl optionally substituted with one or more $R^{1D}$; each $R^{1C}$ is phenyl optionally substituted with one or more $R^{1E}$; each $R^{1D}$ is independently selected from the group consisting of fluoro, chloro, bromo, cyano, methyl, ethyl, methoxy, and ethoxy; and each $R^{1E}$ is independently selected from the group consisting of fluoro, chloro, bromo, cyano, methyl, ethyl, methoxy, and ethoxy. In some embodiments, the compound of Formula I is:

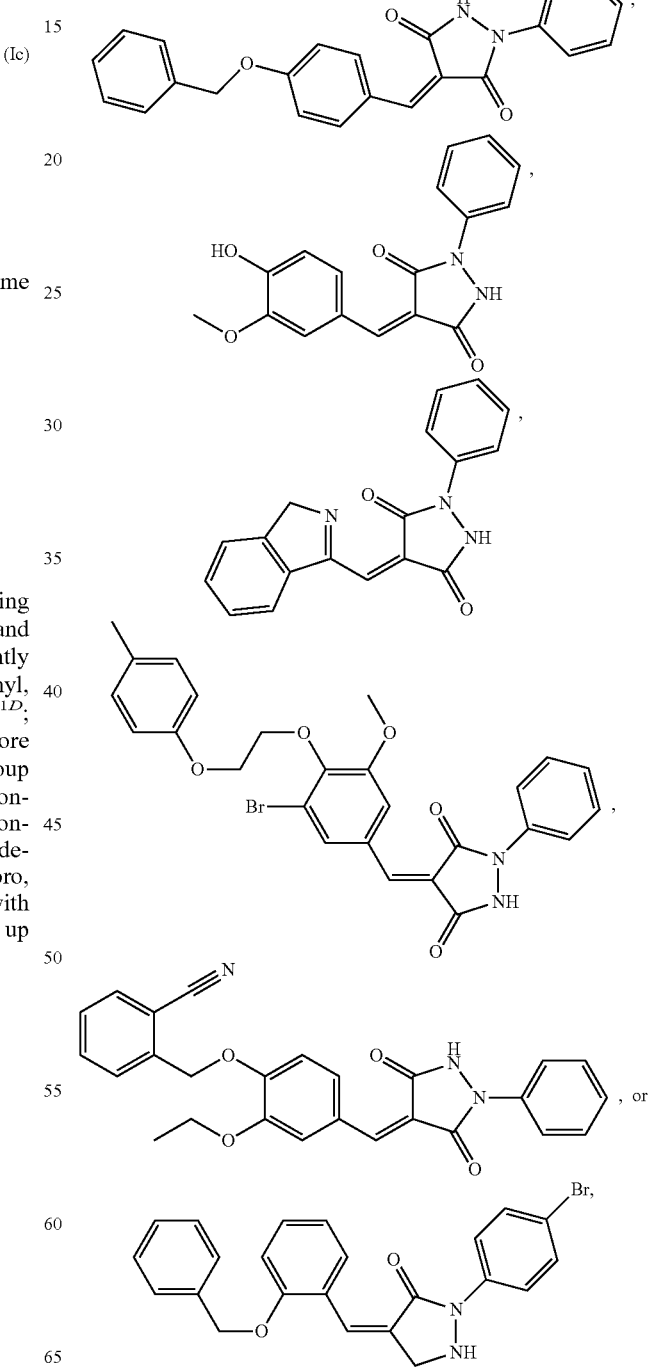

or a pharmaceutically acceptable salt thereof. In some embodiments, the compound of Formula I is not:

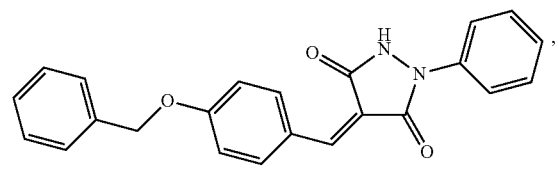,

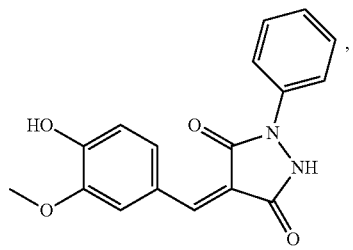,

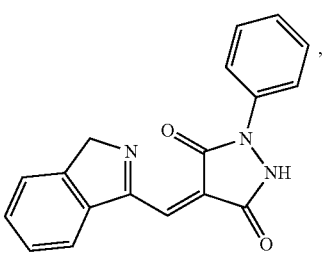,

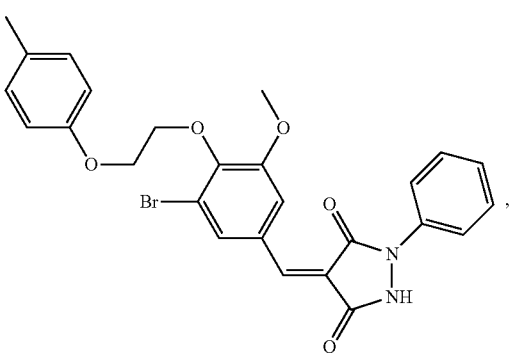,

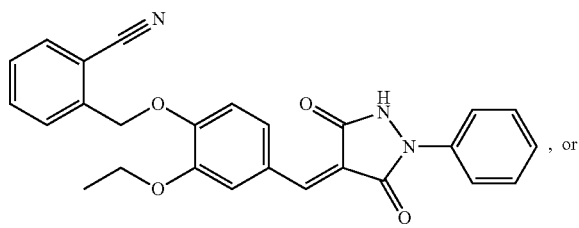, or

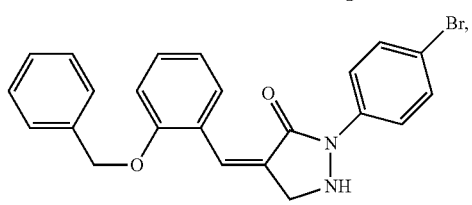

or a pharmaceutically acceptable salt thereof, or tautomer thereof.

Example 1

Figure 8:
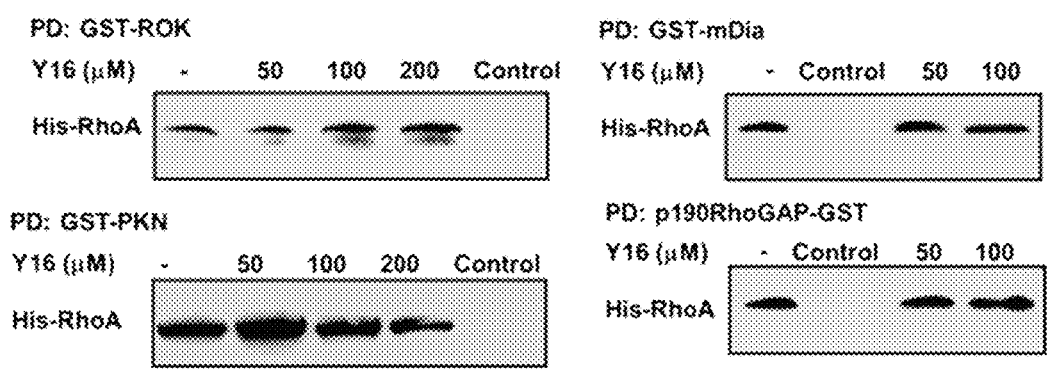
FIG. 8: Shows data indicating Y16 does not effect on RhoA binding to its effectors and RhoGAP.

Compound Y16 and its Analogs are a Class of Inhibitors of G-Protein-Coupled RhoGEFs To examine the specificity of Y16 among RhoA interactive molecules, binding interaction of RhoA with its GEFs, effectors, and RhoGAP was tested in the presence of Y16. These complex formation assays revealed that, Y16 is active in inhibiting RhoA interaction with RhoGEFs p115 RhoGEF and PDZ RhoGEF, the other two RGS domain-containing RhoGEFs in addition to LARG, and it does not affect RhoA interaction with DBL or LBC (FIG. 1A), both of which can readily activate RhoA. Furthermore, Y16 did not interfere with the binding of Cdc42 and Rac1 to their respective GEFs, intersectin and TrioN, respectively, nor RhoA binding with its effector/GAP molecules ROCKII, mDia, PKN, and p190RhoGAP (FIG. 1B and FIG. 8). These results provide biochemical evidence that Y16 is a selective inhibitor of the LARG-related-protein-coupled RhoGEFs, capable of inhibiting the RhoGEF-RhoA interaction. A structure-activity relationship study of structural analogs of Y16, all bearing a phenylpyrazolidine scaffold, by testing their respective activity in inhibiting LARG binding to RhoA in vitro, showed an SAR with Y16 as the most potent analog (Table S2). YA01, which differs in a methyl group from Y16 showed a lower potency (27.1%) relative to Y16.

Figure 1B:
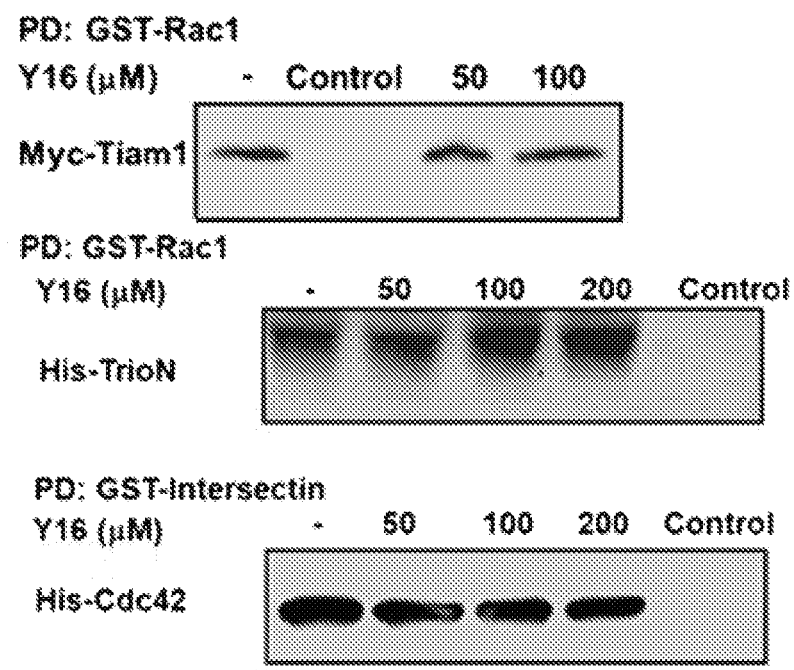

The data in FIG. 1A was obtained by the following procedures. NIH 3T3 cells transiently overexpressing GFP-p115 RhoGEF or Flag-PDZRhoGEF or stably overexpressing GST-DBL or Flag-LBC, were harvested and the cell lysates were subjected to the His-RhoA or GST-RhoA pull-down assay in the absence or presence of Y16 at the indicated concentrations. The data in FIG. 1B was obtained by the following procedures. (Top) Myc-tagged Tiam1 expressed in HEK293T cell lysates were incubated with GST alone or GST-Rac1 conjugated with glutathione agarose beads in the presence of increasing concentrations of Y16. The beads-associated myc-Tiam1 was probed by anti-myc Western blotting. (Middle) $(His)_6$-tagged TrioN (1 μg) was incubated with GST alone or GST-Rac1 conjugated with glutathione agarose beads in the presence of increasing concentrations of Y16. The beads-associated $(His)_6$-TrioN was detected by anti-His Western blotting. (Bottom) $(His)_6$-tagged Cdc42 (1 μg) was incubated with GST alone or GST-Intersectin conjugated with glutathione agarose beads in the presence of increasing concentrations of Y16. The beads-associated $(His)_6$-Cdc42 was detected by anti-His Western blotting. The data in FIG. 8 was obtained by the following procedures. (His)6-tagged RhoA (1 μg) was incubated with GST alone or GST-mDia, GST-PKN, GST-ROK, and GST-p190GAP conjugated with glutathione agarose beads, respectively, in the presence of increasing concentrations of Y16. The beads-associated (His)6-RhoA was detected by anti-His Western blotting. Results shown are representative of three independent experiments.

Recombinant Protein Production.

Recombinant human LARG (residues 765-1,138) containing the DH-PH catalytic module, recombinant human intersectin ITSN (residues 1,227-1,571) containing the DH-PH catalytic module, and the recombinant human TrioN (residues 1,284-1,711) containing the N-terminal DH-PH catalytic module were expressed in *Escherichia coli* BL21 (DE3) strain as N-terminal $(His)_6$-tagged fusion proteins by using the pET expression system (Novagen). Human full-length RhoA (residues 1-193), human full-length Rac1 (residues 1-192), human full-length Cdc42 (1-191), human Intersectin1 (residues 1,227-1,571) containing the DH-PH catalytic module, human PAK1(PBD), human mDia1, human PKN1, human ROCK, and human p190GAP were expressed in *E. coli* DH5α strain as GST fusions by using the pGEXKG vector. The N-terminal tagged GST or (His)$_6$ fusion proteins were purified by glutathione- or Ni$^{2+}$-agarose affinity chromatography. Myc-tagged human Tiam1 DH-PH module was expressed in NIH 3T3 cells by transient transfection and purified by anti-myc immunoprecipitation. GST-fused human DH-PH module of DBL and Flag-tagged human LBCDH-PH module were stably expressed in NIH 3T3 cells. GFP-fused human p115 RhoGEF DH-PH module and Flag-tagged human PDZRhoGEF DH-PH module were expressed in NIH 3T3 cells by transient transfection.

In Vitro Complex Formation Assay.

About 1 μg of (His)$_6$-tagged LARG DH-PH was incubated with 1 μg of EDTA-treated GSTRhoA or Cdc42 or GST alone in a binding buffer [20 mM Tris.HCl (pH 7.6), 100 mM NaCl, 1% BSA, 1% Triton X-100, 1 mM MgCl2] containing 15 μL of suspended glutathione-agarose beads. Y16 or other chemicals were added in the incubation buffer at the indicated concentrations. After an incubation at 4° C. for 1 h under constant agitation, the glutathione beads were washed twice with the binding buffer. The amount of (His)$_6$-tagged protein coprecipitated with GST-fusion bound beads was detected by anti-His Western blotting. Similarly, cell lysates containing myc-Tiam1, (His)$_6$-Cdc42, (His)$_6$-TrioN, or (His)$_6$-RhoA were mixed with purified GST-Rac1, GST-Cdc42, GST-mDia, GST-PKN, GSTROCKII, GST-p190GAP, or GST alone, and pairwise association was assessed in the presence or absence of indicated amount of Y16 and/or Rhosin.

Guanine Nucleotide Exchange Assay.

A 200-μL solution of Tris.HCl (20 mM) (pH 7.6), NaCl (100 mM), and MgCl$_2$ (1 mM) containing purified RhoA, Rac1, or Cdc42 protein (50 or 100 nM) was incubated with 25 nM BODIPY FL-GDP (Invitrogen) at 25° C. until the monitored fluorescence signal was constant, and then 10 μM GDP was added. Self-exchange was monitored by reading the change in fluorescence intensity. The GEF-catalyzed exchange was performed by adding purified LARG, TrioN, or intersectin to the BODIPY-FL-GDP-loaded RhoA or Cdc42 in the presence or absence of Y16 (0-20 μM). Fluorescence intensity was measured using a Cary Eclipse fluorescence spectrophotometer.

Western Blot Analysis.

For Western blot analysis, cell lysates or coprecipitates were separated in 4-15% gradient SDS/PAGE and transferred onto PVDF membrane (Bio-Rad). The membranes were blocked with 1% BSA in TBS-T (20 mM Tris.HCl, pH 7.6, 150 mM NaCl, and 0.1% Tween 20) for 1 h at room temperature, and probed with primary antibodies followed by horseradish peroxidase (HRP)-coupled secondary antibody for enhanced chemiluminescence analysis (Thermo Scientific-Pierce). The anti-GST and anti-myc antibody were purchased from Sigma. The anti-His antibody was from Qiagen. The anti-RhoA, anti-MLC, anti-phospho-MLC, anti-PAK1,2, and anti-phospho-PAK1 antibodies were purchased from Cell Signaling. The anti-Cdc42, anti-Rac1, anti-phospho-FAK (Y397), and anti-FAK antibodies were purchased from BD Biosciences. The anti-RhoB and anti-RhoC antibodies were purchased from Santa Cruz Biotechnology. All of the primary antibodies were diluted (1:1,000) in TBS-T buffer containing 1% BSA. HRP-conjugated goat anti-mouse IgG (Thermo Scientific-Pierce) and HRP-conjugated goat anti-rabbit IgG (Thermo Scientific-Pierce) were used as secondary antibodies.

Statistical Analysis.

All experimental data were analyzed and compared for statistically significant differences by two-tailed Student t test. Data are presented as the averaged values±SDs, where applicable. For Microscale Thermophoresis assay, nonlinear regression was used to fit curves to the mean and SDs (n=3) calculated with GraphPad Prism software. For Western blot quantification, one representative sample of three or more experiments is shown.

Example 2

Biochemical Characterization of Y16 Interaction with LARG

Figure 2A:
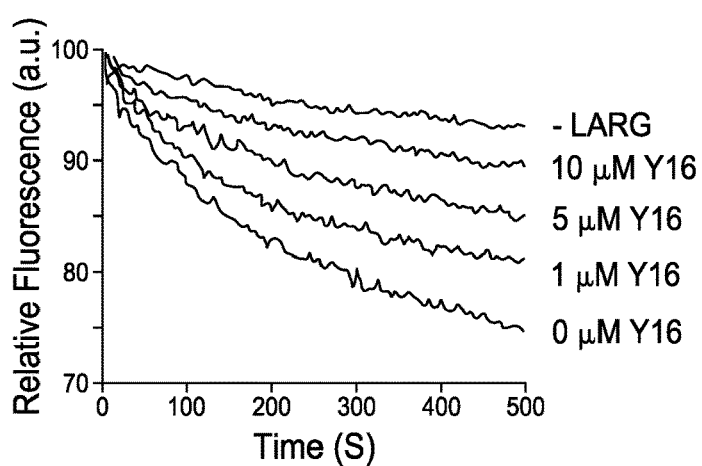
FIGS. 2A-C: Biochemical characterization of Y16 interaction with Rho GEF.
Figure 2B:
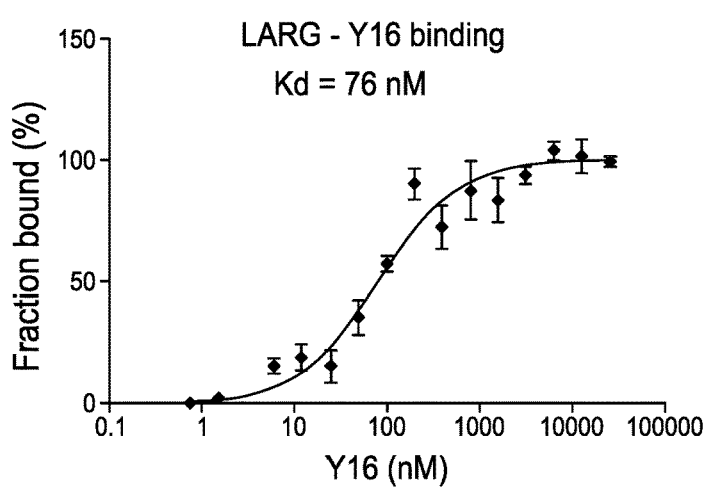
Figure 2C:
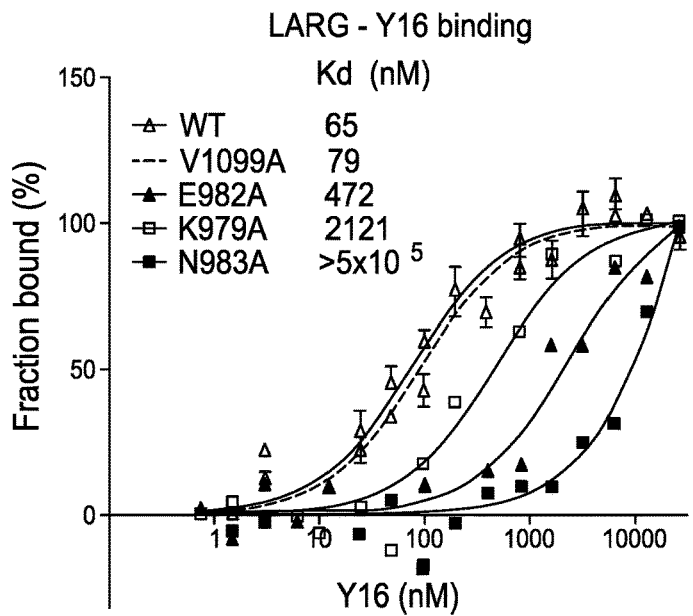

To define the mechanism of Y16 action, the binding constant of Y16 to LARG, effect on LARG-mediated GEF reaction, and possible site of Y16 interaction with LARG were studied. First, a microscale thermophoresis analysis, which allows a sensitive detection of small-molecule binding to a protein target (24), was carried out by titrating the chemical to purified LARG DH-PH protein. This assay shows that Y16 binds to this catalytic fragment of LARG with a $K_d$ of ~76±8 nM (FIG. 2A). As controls, Y16 does not bind to TrioN (a GEF for Rac1/RhoG) or Intersectin (a GEF for Cdc42) (FIG. 9). Second, to examine whether Y16 could inhibit RhoGEF-catalyzed guanine nucleotide-exchange reaction of RhoA, a GDP/GTP exchange assay was performed in the presence or absence of Y16. Y16 was able to inhibit the GDP dissociation from RhoA catalyzed by LARG dose dependently without affecting the GEF reactions of Rac1 and Cdc42 catalyzed by TrioN and Intersectin, respectively (FIG. 2B and FIG. 9). Third, to examine the structural residues of LARG involved in Y16 binding, LARG point mutants bearing Ala mutation around the predicted docking sites, i.e., E982, K979, and N983, of LARG, were tested for their binding affinities to Y16. Two of these residues are conserved among three G-protein-coupled RhoGEFs (PDZ-RhoGEF and p115RhoGEF), but are mostly divergent from other DBL family RhoGEFs. The N983A mutant lost the binding ability to Y16 with a $K_d$>500 μM, whereas the K979A and E982A mutants showed a reduced affinity with $K_d$ values of 0.47 and 2.1 μM, respectively (FIG. 2C). As a control, the V1099A mutant of LARG, a mutant bearing a mutation outside the predicted docking pocket, was not affected in Y16 binding ($K_d$=79±49 nM). Overall, these results suggest binding of Y16 to the unique site in the DH-PH domains of LARG to impinge on the GEF activation reaction of the RhoA substrate.

The information in FIG. 2 was obtained by the following procedures (A) Increasing concentrations of G04 or Y16 were included in the exchange buffer as indicated. (B) Purified proteins including RhoA and LARG were first labeled with Alexa 647 fluorescence dye. G04 or Y16 was titrated between 0.76 and 25,000 nM to the constant amount of labeled proteins (100 nM). Data are representative of three independent experiments. (C) Purified LARG mutants were first labeled with Alexa 647 fluorescence dye. Y16 was titrated at increasing concentrations. Data are representative of three independent experiments.

The information in FIG. 9A was obtained by the following procedures. (A) Purified proteins TrioN and Intersectin were first labeled with Alexa 647 fluorescence dye. Y16 was titrated between 0.76 and 250,000 nM to the constant amount of labeled proteins (100 nM). The reaction was performed in 50 mM Hepes, 50 mM NaCl, 0.01% Tween 20, and 2 mM MgCl$_2$. Data were normalized to ΔFnorm [‰]

(10*(Fnorm(bound)−Fnorm (unbound))). No binding of Y16 to either Intersectin or TrioN was detected. All of the data are representative of three independent experiments. (B) Purified (His)$_6$-tagged Cdc42 or Rac1 protein (100 nM) was subjected to the FL-GDP dissociation assay without the presence of a GEF (top curves) or in the presence of Intersection (50 nM) or TrioN (100 nM) DH-PH module. Y16 at the indicated concentration was included in each assay and fluorescence intensity change was monitored with time. The upper curve in each figure represents Cdc42 or Rac1 intrinsic nucleotide exchange, whereas the lower curves represent ITSN or TrioN-catalyzed nucleotide exchange in the absence or presence of Y16.

Microscale Thermophoretic Analysis.

A NanoTemper Monolith Instrument (NT.015) was used for measuring thermophoresis (SI Materials and Methods). In this instrument, an infrared laser (IR laser) beam couples into the path of light (i.e., fluorescence excitation and emission) with a dichroic mirror and is focused into the sample fluid through the same optical element used for fluorescence imaging. The IR laser is absorbed by the aqueous solution in the capillary and locally heats the sample with a 1/e2 diameter of 25 μm. Up to 24 mW of laser power were used to heat the sample, without damaging the biomolecules (29). Thermophoresis of the protein in the presence of varying concentrations of compound was analyzed for 30 s. Measurements were performed at room temperature and SD was calculated from three independent experiments. Data were normalized to either ΔFnorm [‰] (10*(Fnorm(bound)−Fnorm (unbound))) or Fraction bound (ΔFnorm [‰]/amplitude).

Example 3

Y16 Specifically Inhibits RhoA Activity in Cells

Figures 3A, 3B:
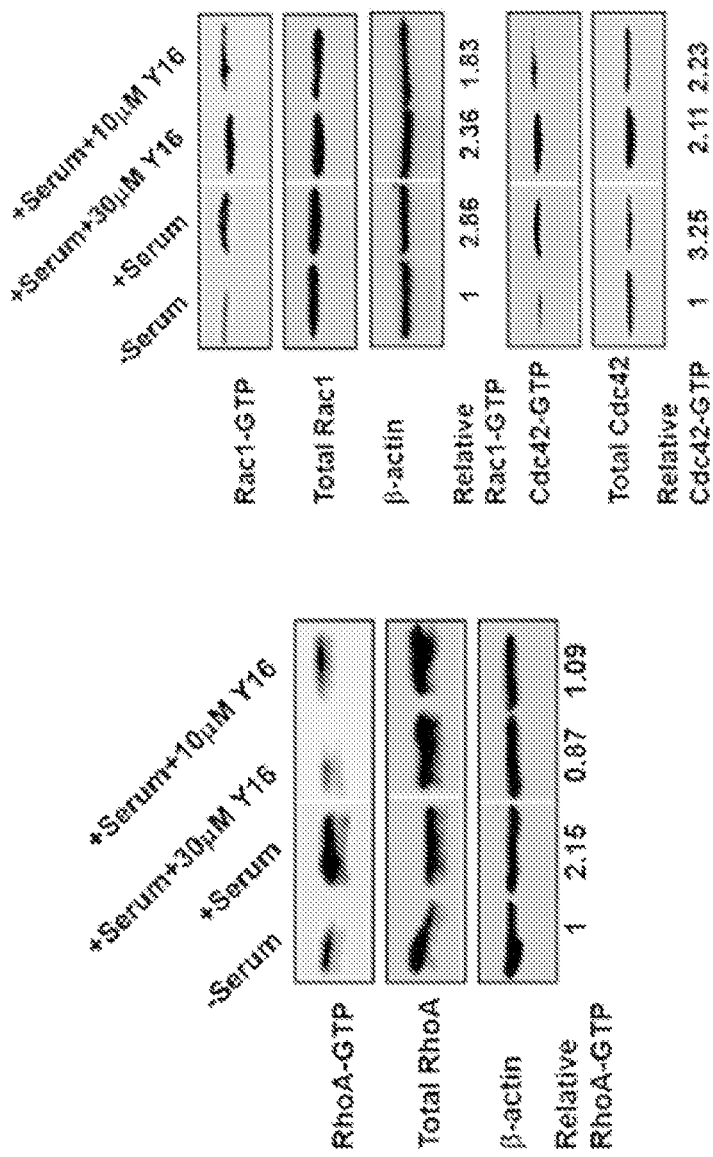
FIGS. 3A-E: Cellular efficacy and specificity of Y16 in suppressing RhoA activity.
Figure 3C:
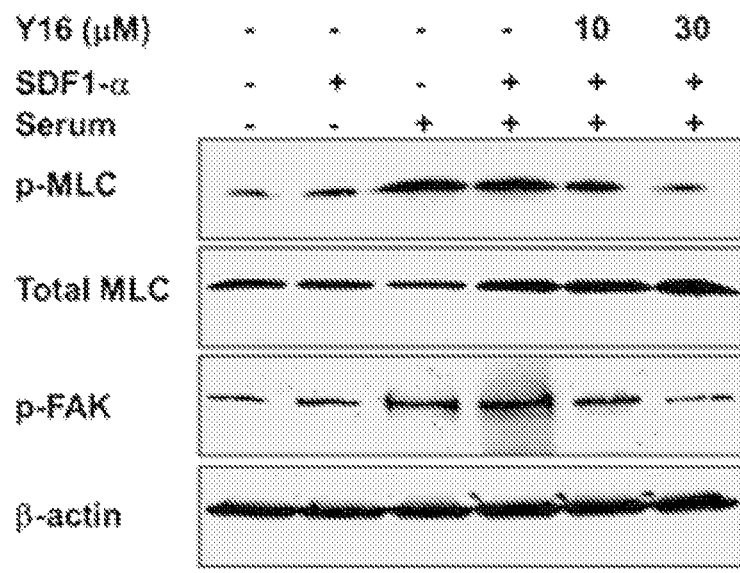
Figure 3D:
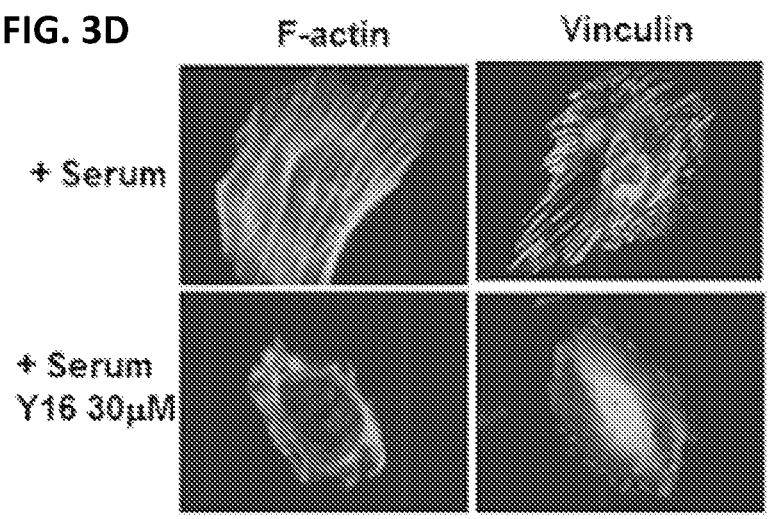
Figure 11:
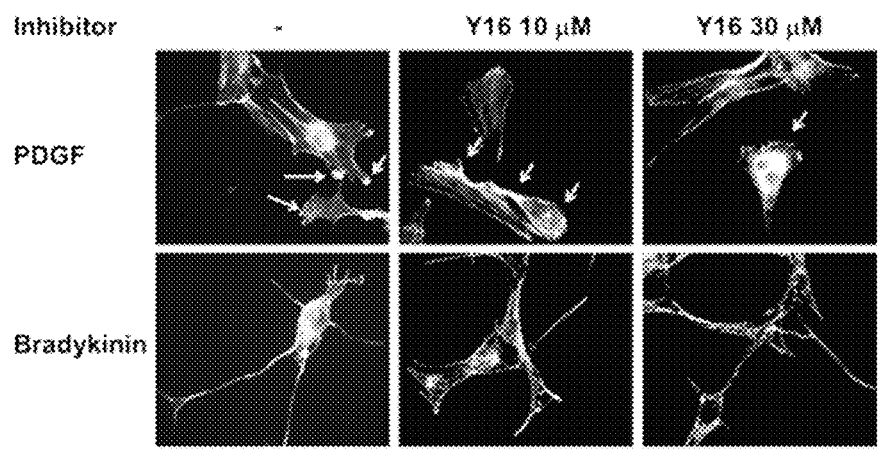
FIG. 11: Shows data indicating Y16 has no effects on the Bradykinin-induced filopodia or PDGF-induced lamellipodia formation.

To examine whether RhoGEF inhibitor Y16 is effective in specifically suppressing RhoA activity in cells, fibroblast cells grown in serum-free media were treated with Y16 in different concentrations, followed by stimulation with 10% calf serum. As shown in FIG. 3A, Y16 could inhibit RhoA-GTP formation induced by serum dose dependently and was specific for RhoA because it did not affect the activities of Cdc42 and Rac1 in the same cells (FIG. 3B). In addition, Y16 efficiently inhibited serum or SDF-1α-induced phospho-MLC and phospho-FAK formation (FIG. 3C), which are downstream of RhoA. Previously, it has been established that the serum component lysophosphatidic acid (LPA) elicits a signaling cascade through G-protein-coupled Rho-GEFs and RhoA to regulated cell cytoskeleton organizations (1-3). To further evaluate the ability of Y16 to inhibit RhoA-mediated cell functions, we next examined actin cytoskeleton structures of cells stimulated by serum or LPA in the absence or presence of Y16. FIG. 3D shows that, in the presence of Y16, both stress fiber and focal complex of the cells were significantly reduced, whereas FIG. 11 shows that the Rac1-mediated lamellipodia and Cdc42-mediated filapodia under the stimulation by PDGF and Bradykinin, respectively, were not affected. Given the implicated role of RhoA in actin cytoskeleton organization and adhesion (1-3), these results demonstrate that Y16 is active in specifically inhibiting cellular RhoA-GTP and RhoA-mediated signaling function.

Figure 3E:
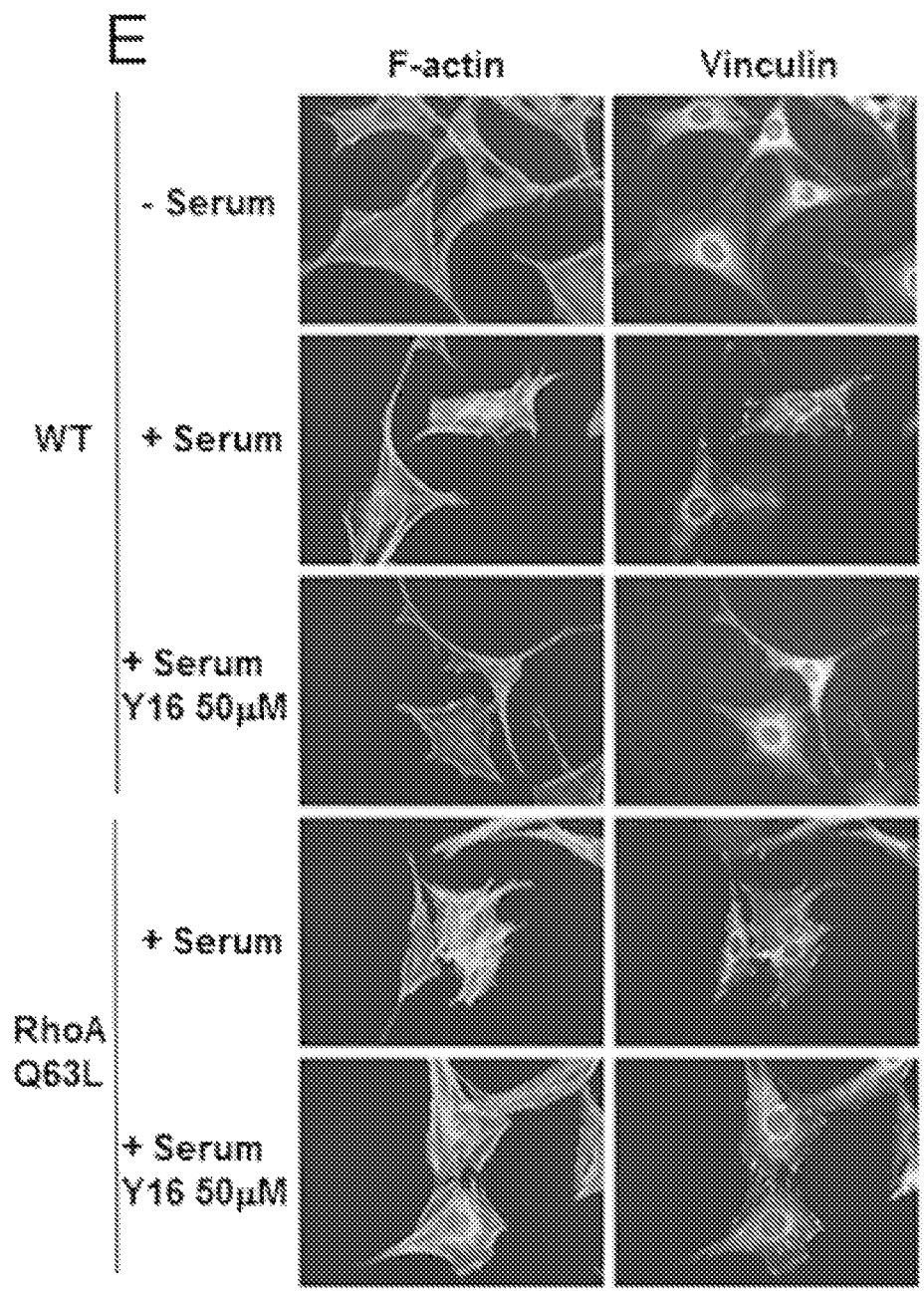
Figure 10:
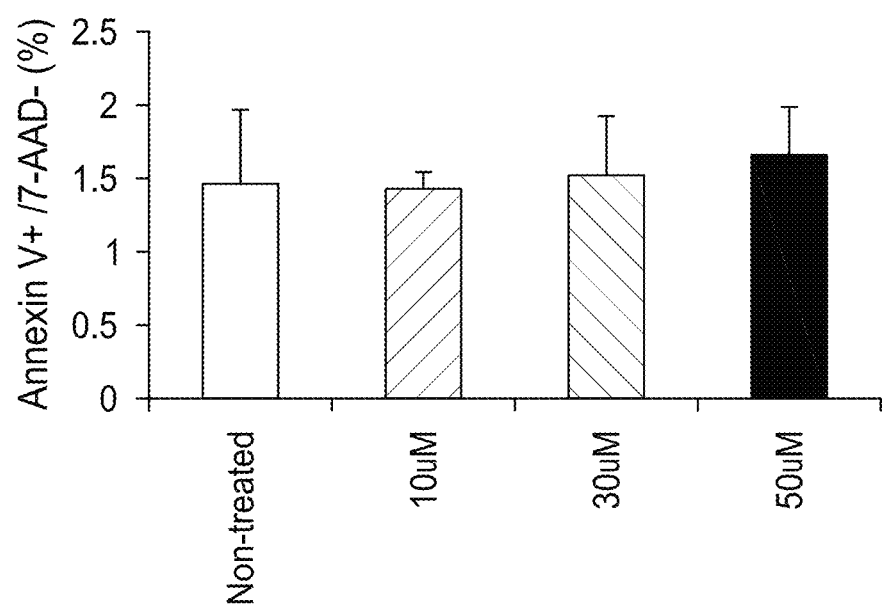
FIG. 10: Shows data indicating the effect of Y16 on cell survival.
Figure 12:
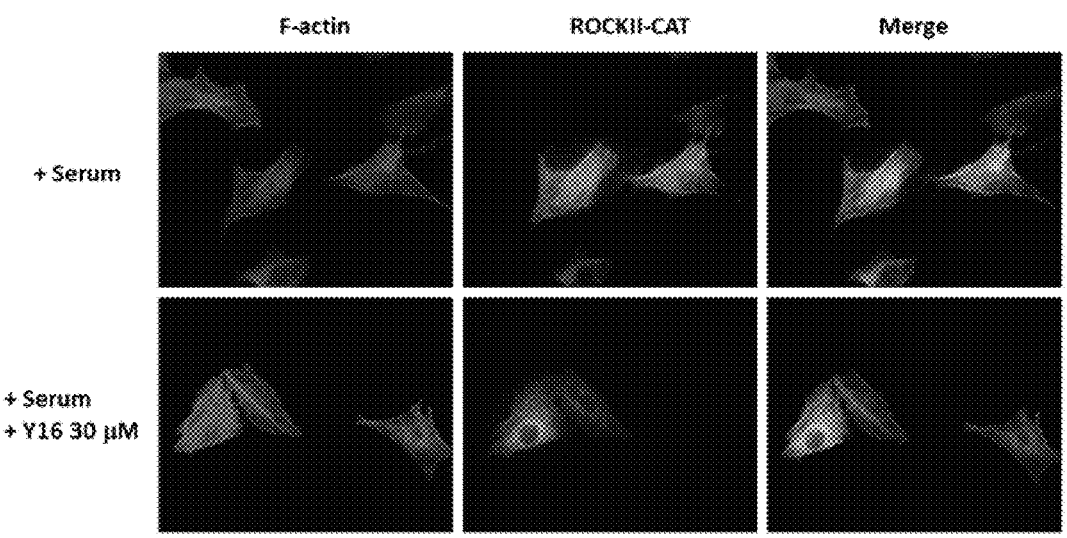
FIG. 12: Shows data indicating Y16 treatment does not affect constitutively active ROCK II mutant (ROCKII-CAT) induced actin stress fiber formation.
Figure 13:
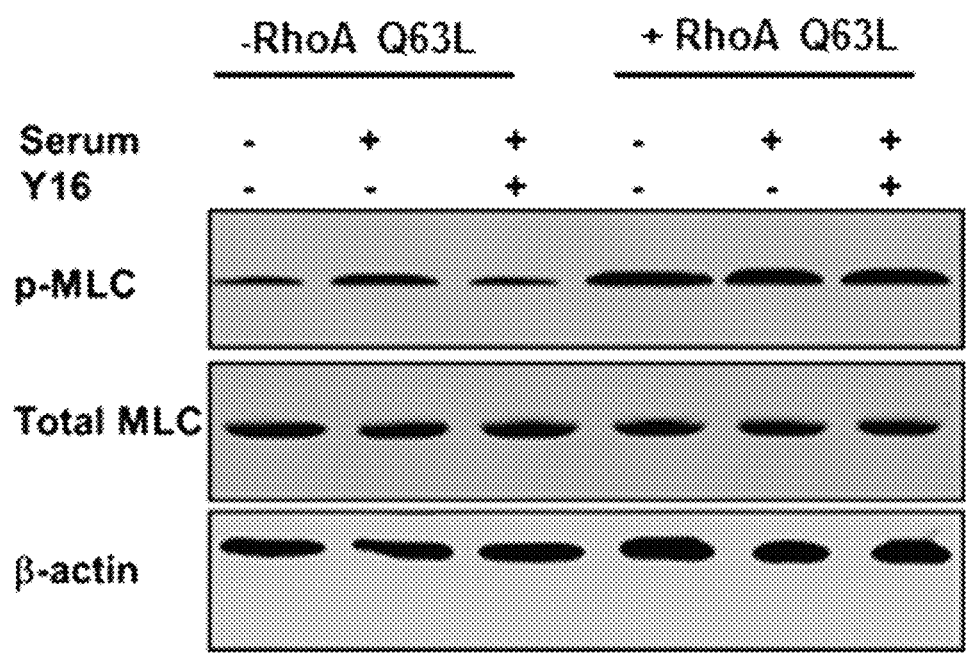
FIG. 13: Shows data indicating Y16 treatment does not affect the downstream signaling of the RhoA constitutive active mutant (Q63L).

To further examine the specificity of Y16 in cells, Y16 was tested in cells expressing constitutively active RhoA or ROCKII mutant that produces F-actin-based responses independent of endogenous RhoGEF activity. As shown in FIG. 3E and FIG. 12, Y16 did not alter actin stress fiber or focal adhesion complex formation induced by a constitutively active RhoA mutant Q63L, or a constitutively active ROCKII. Furthermore, although Y16 was capable of inhibiting serum-induced phospho-MLC formation, an event mediated by RhoA activity in NIH 3T3 cells (FIG. 3C), it did not interfere with phosphor-MLC in cells overexpressing RhoA Q63L mutant (FIG. 13). Under the assay conditions, Y16 appeared to be noncytotoxic as it did not affect the survival status of the cells (FIG. 10). These results provide further evidence that the effect of Y16 toward GEF-RhoA signaling is likely specific in cells.

The information in FIG. 3 was obtained by the following procedures. (A and B) NIH 3T3 cells were treated with Y16 at the indicated concentrations for 24 h in serum-free media. Cells were subsequently stimulated with 10% calf serum for 15 min and were subjected to GST-Rhotekin or GST-PAK1 effector domain pull-down assays, and the activities of RhoA, Cdc42, and Rac1 were examined. Relative amounts of GTP-bound form of the GTPases were quantified by densitometry measurements and normalized to those of the unstimulated cells. (C) Western blots are of p-MLC and p-FAK and relevant controls of NIH 3T3 cells treated with Y16 at indicated concentrations in serum-free media and subsequently stimulated by 10% calf serum or/and 100 ng/mL SDF1-α for 10 min. (D) Cells were treated with 30 μM Y16 in serum-free media, subsequently stimulated with 10% calf serum for 10 min, and stained with rhodamine-phalloidin for F-actin and antivinculin for focal adhesion complexes. Images shown are representative of more than 100 cells examined. (E) NIH 3T3 cells were transfected with constitutively active RhoA Q63L mutant or a control vector and subsequently were grown on tissue culture dish in a serum-free media in the presence of 50 μM Y16. After 24-h starvation, cells were stimulated with 10% calf serum for 30 min and were stained with rhodamine-phalloidin to reveal F-actin structure and anti-vinculin antibody for focal adhesion.

The information in FIG. 10 was obtained by the following procedures. NIH 3T3 cells were labeled with Annexin-V/ 7AAD and subjected to FACS analysis to determine the percent of cell populations undergoing apoptosis after treatment with the Y16 at the indicated concentrations for 24 h. No significant difference was detected between the non-treated and Y16 treated cells (all concentrations shown). Results shown are representative of three independent experiments.

The information in FIG. 11 was obtained by the following procedures. NIH 3T3 cells were treated with Y16 of the indicated concentrations in serum-free DMEM before stimulation with Bradykinin (100 ng/mL) or PDGF (10 ng/mL) for 10 min. The cells were stained with rhodamine-phalloidin to reveal the F-actin structures. The arrows show the lamellipodia.

The information in FIG. 12 was obtained by the following procedures. WT NIH 3T3 cells and ROCKII-CAT/EGFP-expressing cells were grown on tissue culture dish. After 24-h starvation in the presence of 30 μM Y16, cells were stimulated with 10% calf serum for 30 min and were costained with rhodamine-phalloidin for F-actin and imaged for EGFP for ROCKII-CAT expression. The data are representative of three independent experiments.

The information in FIG. 13 was obtained by the following procedures. Western blotting of p-MLC and relevant controls of the NIH 3T3 cells with or without RhoAQ63L expression treated in the absence or presence of Y16 at 50

µM for 24 h in a DMEM containing 10% calf serum. Results shown are representative of three independent experiments.

Immunofluorescence.

After overnight serum starvation in the absence or presence of Y16, G04, or G04+Y16 combination at the indicated concentration, NIH 3T3, Swiss 3T3, or NIH 3T3 cells expressing constitutive active mutant of ROCKII (CAT) or RhoA (Q63L) grown in the tissue culture dish were treated with PDGF (10 ng/mL), LPA (20 ng/mL), Bradykinin (100 ng/mL) for 10 min or 10% calf serum for 15 min. The cells were fixed with 3.7% formaldehyde in PBS for 15 min and permeabilized with 0.1% Triton X-100 for 20 min. The cells were stained with rhodamine-phalloidin (Molecular Probes) for F-actin, anti-vinculin (BD Biosciences) for focal complex. The fluorescent images were obtained by using a Zeiss fluorescence microscope.

Cell Cytotoxicity Assay.

NIH 3T3 cells were treated in the presence or absence Y16 at the indicated concentration and then subjected to propidium iodide/RNase staining (BD Biosciences) followed by FACS analysis. Cell apoptosis was measured by Annexin V-FITC and 7AAD (BD Biosciences) staining followed by FACS.

Endogenous Rho GTPase Activity Assay.

NIH 3T3 cells, MCF7 cells, or HME cells were grown in log phase in a 10-cm dish or a six-well dish, and were starved in serum-free medium in the presence or absence of Y16 at indicated concentrations for 24 h and were subsequently stimulated with 10% calf serum or FBS for 15 min. Cells were lysed in a buffer containing 20 mM Tris.HCl, pH 7.6, 100 mM NaCl, 1% Triton X-100, 10 mM $MgCl_2$, 2 mM NaF, and protease inhibitors (2 mM PMSF, 10 µg/mL leupeptin, 10 µg/mL aprotinin). Lysates were clarified, the protein concentrations were normalized, and the GTP-bound RhoA, Rac1, or Cdc42 in the lysates were measured by respective anti-RhoA, Rac1, and Cdc42 Western blotting of the effector domain pull downs.

Example 4

Figure 4A:
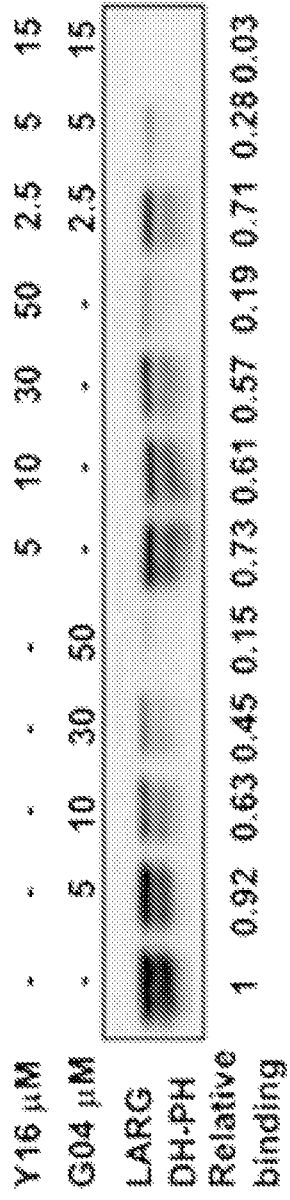
Figure 4B:
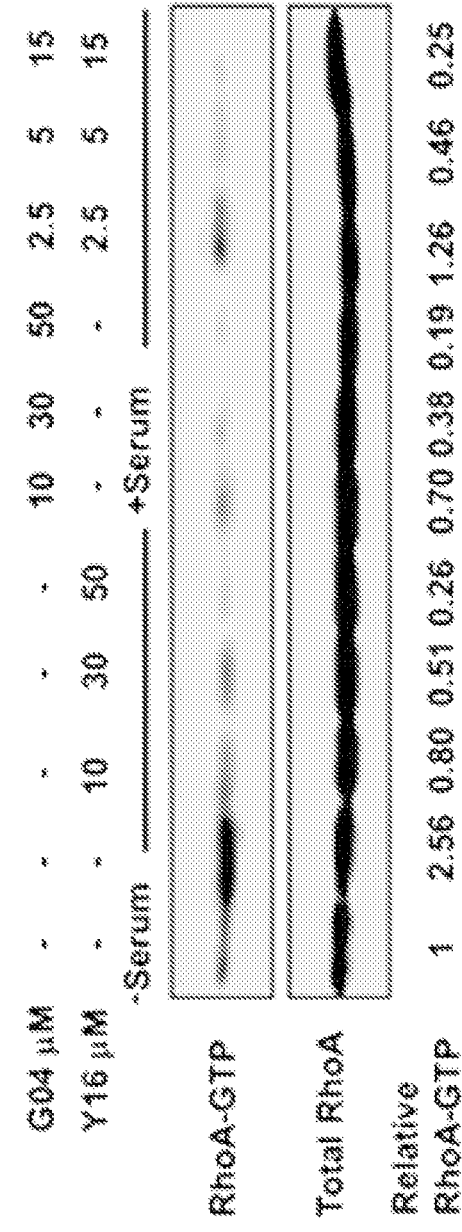

Y16 Acts Synergistically with Rhosin/G04 in Inhibiting LARG-RhoA Interaction and RhoA Activity Rhosin/G04 specifically binds to RhoA protein and inhibits RhoA activity in diverse physiological and pathological systems. Dual targeting by the two inhibitors was tested a synergistic effect on the GEF-RhoA interaction as they act on the same interface of GEF-RhoA binding, and consequently, on RhoA activity and signaling functions. In vitro and cellular test were performed using Rhosin/G04 and Y16 together. First, when Rhosin/G04 and Y16 were combined together, the working concentrations required for effective inhibition of RhoA binding to LARG were significantly decreased ($IC_{50}$ of ~1 µM compared with ~10 and ~5 µM of G04 or Y16 alone, respectively) (FIG. 4A), suggesting that Rhosin/G04 and Y16 can synergistically inhibit RhoA-LARG binding interaction. Second, applying Rhosin/G04 and Y16 together to NIH 3T3 cells potently inhibited RhoA activity (FIG. 4B). At 2.5 µM each, Rhosin and Y16 inhibited ~50% RhoA-GTP content, and at 5 µM each ~80% RhoA-GTP stimulated by serum, which were much more potent than the effect of Rhosin/G04 or Y16 acting alone (~80% inhibition at 30 µM). Even under a higher concentration of Y16 and Rhosin/G04 combination (50 µM each) when endogenous RhoA-GTP content was effectively suppressed, no effect on Rac1-GTP or Cdc42-GTP content in cells was observed (FIG. 4C), suggesting a high degree of specificity of the inhibitors. The Rhosin/G04 and Y16 combination was able to completely abolish the RhoA-mediated cell stress fiber formation at 2.5 µM concentration of each of the inhibitors, whereas it required over 10 µM of Rhosin/G04 or Y16 alone to show such a cellular effect (FIG. 4D). These results suggest that Y16 and Rhosin/G04 can act synergistically to inhibit RhoA activity.

The information in FIG. 4 was obtained by the following procedures. (A) Dose-dependent specific inhibition of LARG binding to RhoA by Y16, G04, or G04+Y16 combination at varying concentrations. (B) NIH 3T3 cells were treated with Y16, G04, or G04+Y16 combination at the indicated concentrations for 24 h in serum-free media. Cells were subsequently stimulated with 10% calf serum for 15 min and were subjected to GST-Rhotekin effector domain pull-down assays, and the activities of RhoA were examined. Relative amounts of GTP-bound form of the GTPases were quantified by densitometry measurements and normalized to those of the unstimulated cells. (C) NIH 3T3 cells were treated with Y16, G04, or G04+Y16 combination at the indicated concentrations for 24 h in serum-free media. Cells were subsequently stimulated with 10% calf serum for 15 min and were subjected to GST-Rhotekin and GST-PAK1 effector domain pull-down assays, and the activities of RhoA, Cdc42, and Rac1 were examined. Relative amounts of GTP-bound form of the GTPases were quantified by densitometry measurements and normalized to those of the nontreated cells. (D) NIH 3T3 cells were treated with Y16, G04, or G04+Y16 combination of the indicated concentrations in serum-free DMEM medium prior to stimulation with LPA (20 ng/mL) for 10 min. The cells were stained with rhodamine-phalloidin to reveal F-actin structures.

Cell Proliferation Assay.

The growth rates of the MCF cells in the presence of Y16, G04, or G04+Y16 combination were determined by counting the number of cells in triplicate daily during the cell growth period. Briefly, $1.5 \times 10^4$ cells were plated in 24-well plates in the presence of 10% FBS. Cell numbers at different time points were determined using a hemocytometer.

Cell Migration Assay.

Cell migration assays were performed using modified Boyden chambers (8.0-µm pore size; Becton Dickinson). The lower chamber was filled with 600 L of DMEM containing 10% FBS in the presence of Y16, G04, or G04+Y16 combination. Cells were harvested with trypsin/EDTA, resuspended to $2.5 \times 10^5$ cells/mL using serum-free DMEM containing Y16, G04, or G04+Y16 combination and added to the upper chamber. The cells were allowed to migrate in 37° C. at 5% $CO_2$ for 16 h. Nonmigratory cells at the upper surface of the membrane were removed and the migrant cells attached to the lower surface were stained with 5% Giemsa solution and quantified. Each assay was performed three times in triplicates.

Cell Invasion Assay.

Cell invasion assays were performed using the 6.4-mm Biocoat Matrigel invasion chambers equipped with the 8.0-µm pore-sized PET membrane filters (BD Biosciences) according to the manufacturer's instructions. Briefly, $2.5 \times 10^4$ cells were suspended in 0.5 mL of culture medium in the presence of Y16, G04, or G04+Y16 combination and were plated in the upper chamber. FBS (10%) in the culture medium was added to the lower chamber (also containing of the inhibitors) as a chemoattractant. Cells in the invasion chambers were incubated in a humidified incubator (37° C. and 5% $CO_2$) for 16 h. The cells that traversed the Matrigel matrix and the 8.0-µm membrane pores and spread to the lower surface of the filters were stained with 5% Giemsa solution for visualization and cell number quantification. The relative invasion index was normalized by dividing the invaded cell number of each sample by that of the control. Each data point of the invasion test was derived from triplicate chambers, and error bars represent the mean SE.

Example 5

Figure 5A:
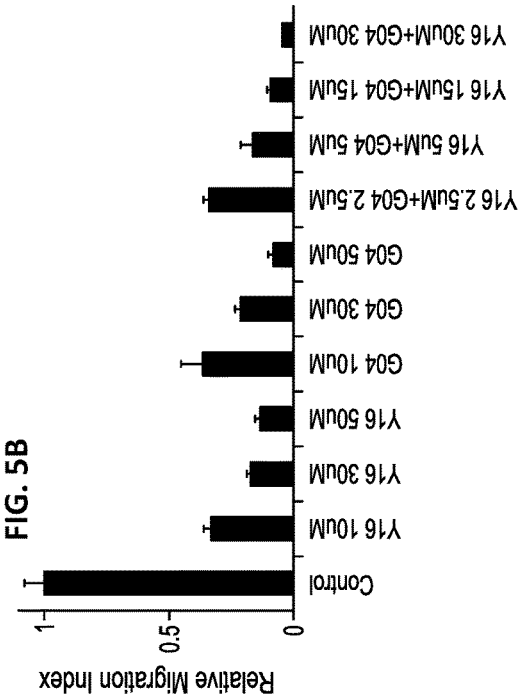
FIGS. 5A-E: Targeting RhoA activity by Y16 and Rhosin in breast cancer cells.
Figure 5B:
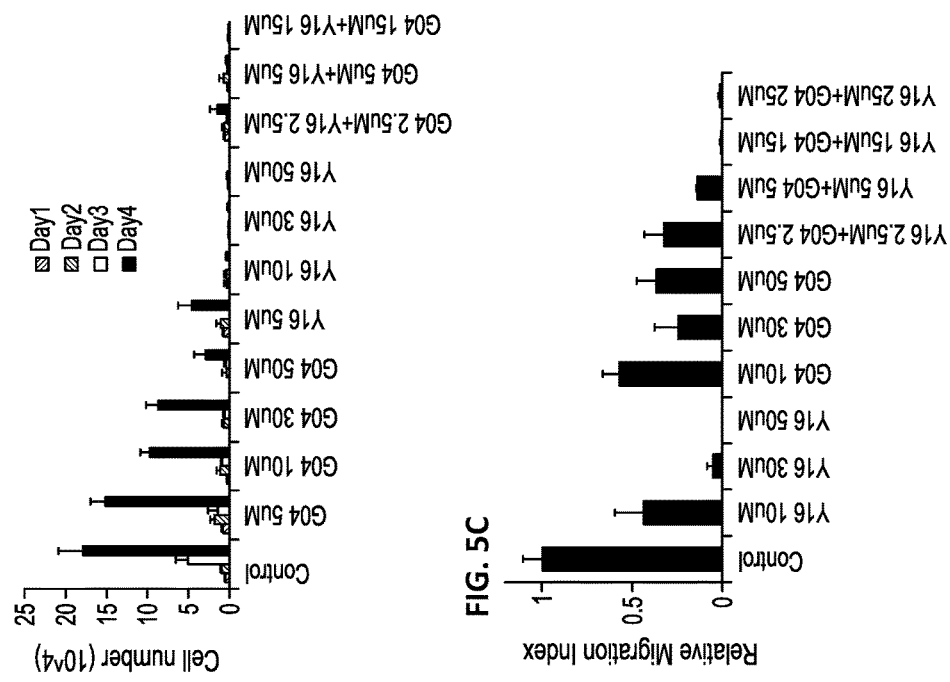
Figure 5C:
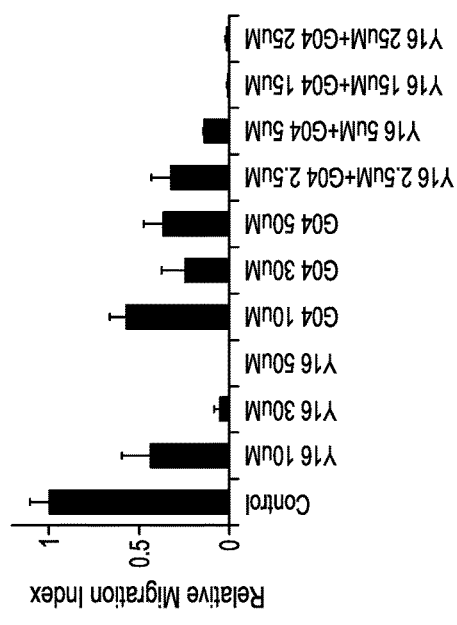
Figure 5D:
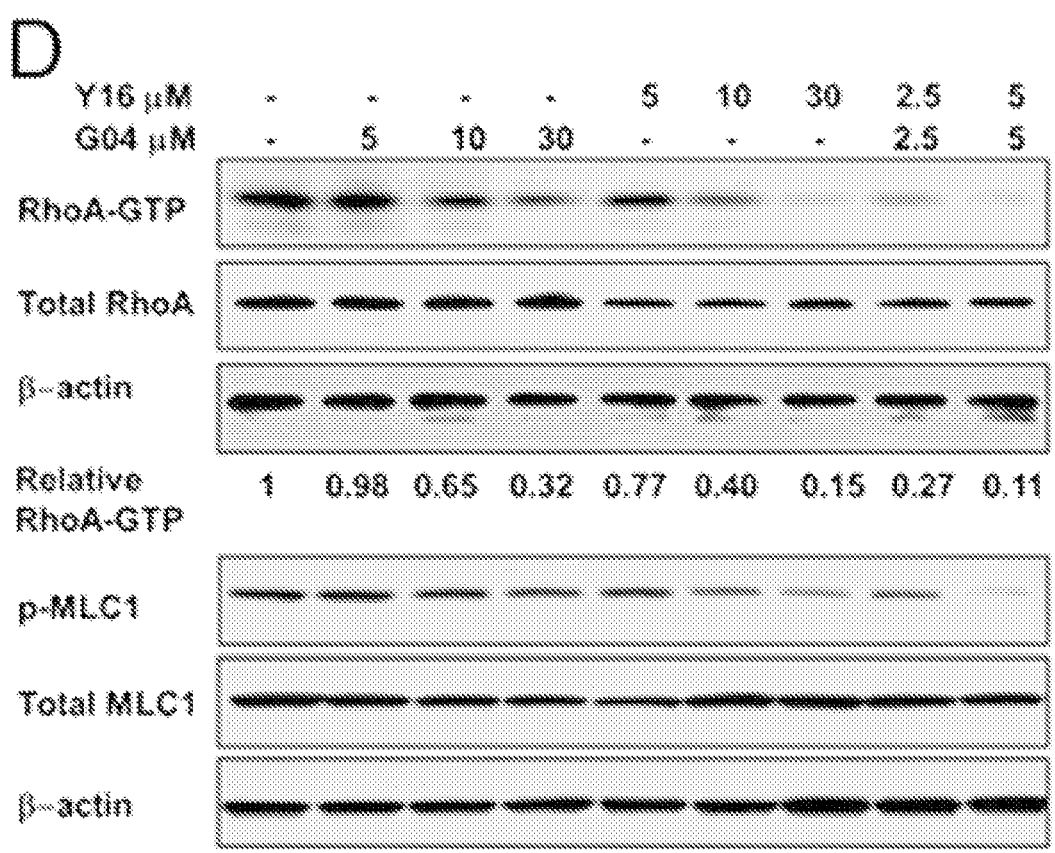
Figure 5E:
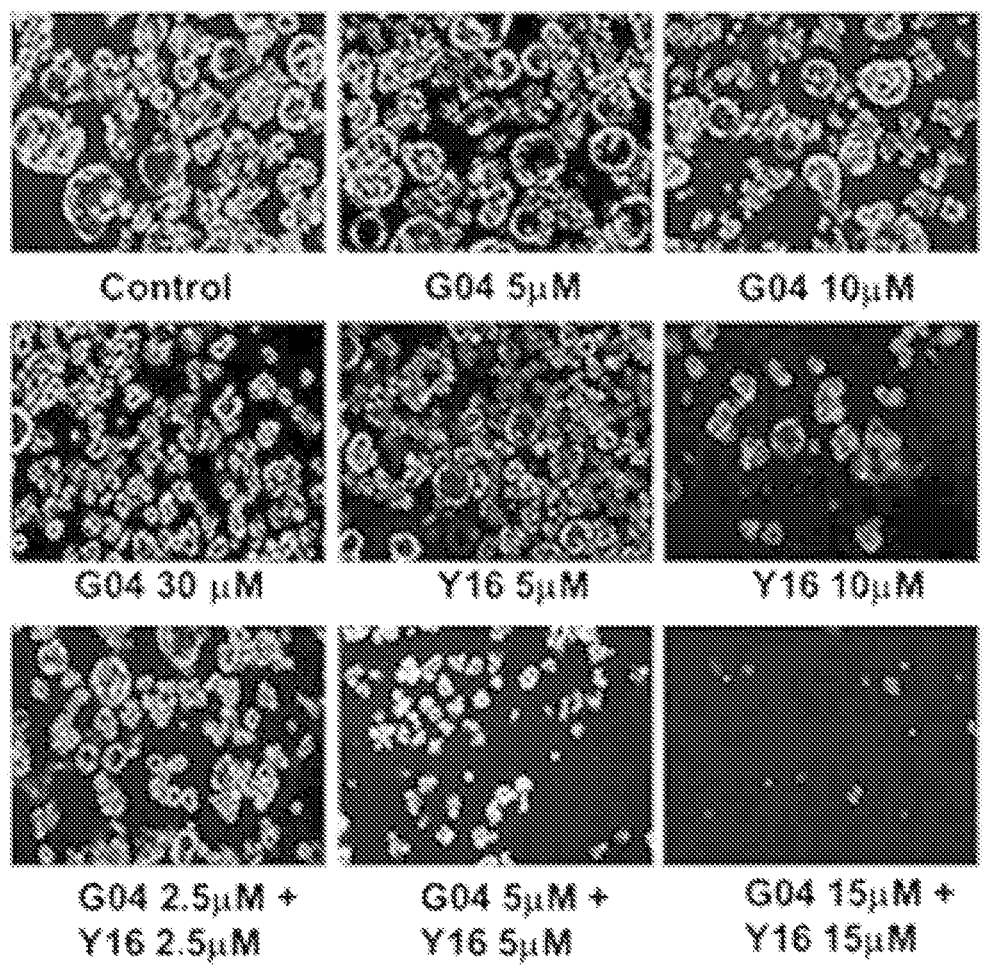

Y16 Effectively Inhibits the Growth, Migration, and Invasion Activities of Breast Cancer Cells The effect of Y16 on the growth, migration, and invasion, as well as mammosphere formation, activities of breast cancer cells, properties associated with tumorigenic potential (25), were tested. Y16 inhibited MCF7 breast cancer cell growth, migration, and invasion, and the RhoA inhibitor Rosin/G04 (FIG. 5 A-C). The Y16-treated MCF7 cells also yielded smaller size and reduced number of mammospheres dose dependently (FIG. 5E). Thus, Y16 is capable of suppressing breast cancer cell behaviors.

To examine whether Y16 could worked synergistically with Rhosin/G04 to more effectively suppress cancer cell activities, combinations of Y16 with Rhosin/G04 at micromolar working concentrations were tested. Combined treatment of Y16 and Rhosin/G04 at 5 µM each could inhibit cell growth, migration, invasion, and mammosphere formation activities (FIG. 5 A-E and FIG. 14), showing a synergy over the effects when each inhibitor was used alone. Accompanying the manifested cell activity inhibitions, RhoA-GTP and downstream signaling of RhoA, measured by p-MLC level, showed a dose-dependent reduction in the Rhosin/G04- or Y16-treated mammospheres (FIG. 5D). Although Rhosin/G04 or Y16 administration alone caused ~50% inhibition of RhoA activity at 10 µM, combined Rhosin/G04 and Y16 reached ~70% inhibition of RhoA-GTP or the downstream p-MLC when each was at 2.5 µM (FIG. 5D). These results indicate that Y16 and Rhosin/G04, each capable of selectively inhibiting one target of the RhoGEF-RhoA enzyme-substrate pair, can act synergistically to inhibit RhoA activity and RhoA-regulated breast cancer cell behaviors.

The information in FIG. 5 was obtained by the following procedures. (A) Y16, G04, or G04+Y16 combination inhibits MCF7 breast cell growth. MCF7 cells were plated at $1.5 \times 10^4$/24 well in the presence of Y16, G04, or G04+Y16 combination. Cell numbers were determined at the indicated times. (B) MCF7 cells were subjected migration assays in the presence of Y16, G04, or G04+Y16 combination. (C) The invasive activities were assayed in a Matrigel-coated transwell. (D) Y16, G04, or G04+Y16 combination inhibits RhoA and its downstream signaling activities in MCF7-derived mammospheres. (Upper) MCF7-derived mammospheres were treated with Y16, G04, or G04+Y16 combination at the indicated concentrations. Spheres were collected, and the RhoA activity was examined. Relative amounts of GTP-bound form of RhoA were quantified by densitometry measurements and normalized to those of the untreated cells. (Lower) Western blots are of p-MLC of MCF7-derived mammospheres. Y16, G04, or G04+Y16 combination inhibits MCF-7 cell-derived mammosphere formation. (E) MCF-7 cells were treated with Y16, G04, or G04+Y16 combination at the indicated concentrations for 24 h in serum-free media. MCF7 cells were dissociated to single cells with trypsin and cultured for 10 d at the density of $2 \times 10^4$/mL in suspension in the media containing G04 or Y16 at the indicated concentration. Photographs were taken after a 10-d culture. Images shown are representative of 5-10 fields containing a total of at least 100 spheres, which were chosen randomly.

Figure 14:
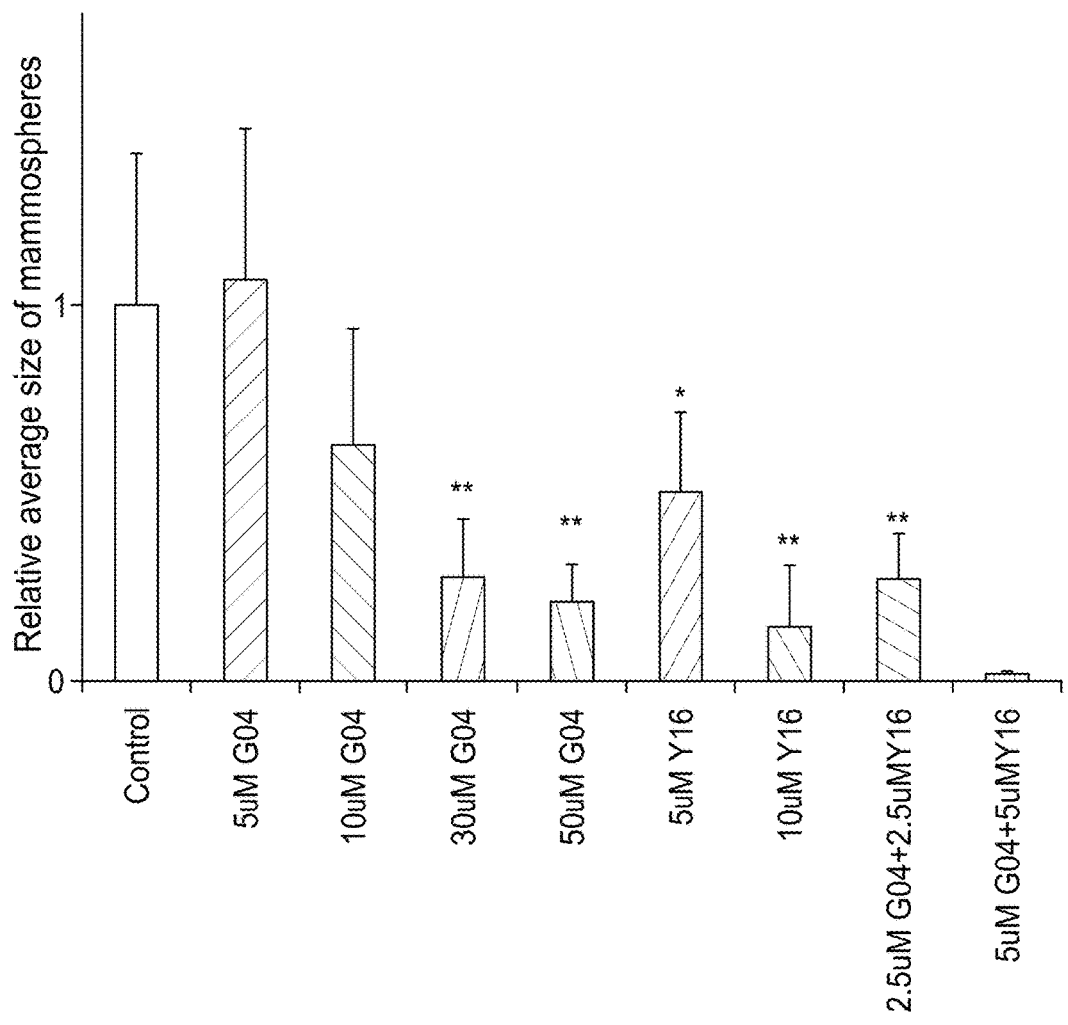
FIG. 14: Shows data indicating Effects of Y16, G04, or G04+Y16 combination on MCF-7 cell-derived mammosphere formation.

The information in FIG. 14 was obtained by the following procedures. MCF-7 cells were treated with Y16, G04, or G04+Y16 combination at the indicated concentrations for 24 h in serum-free media. MCF7 cells were dissociated to single cells with trypsin and cultured for 10 d at the density of $2 \times 10^4$/mL in suspension in the media containing G04 or Y16 at the indicated concentration. The average size of the mammosphere was measured and normalized to the control. All experimental data were analyzed and compared for statistically significant differences by two-tailed Student t test (**$P<0.01$; *$P<0.05$). More than 100 mammospheres were examined for each experimental condition.

Example 6

A HTS Platform Screening for LARG Enzymatic Inhibitors

Figure 7:
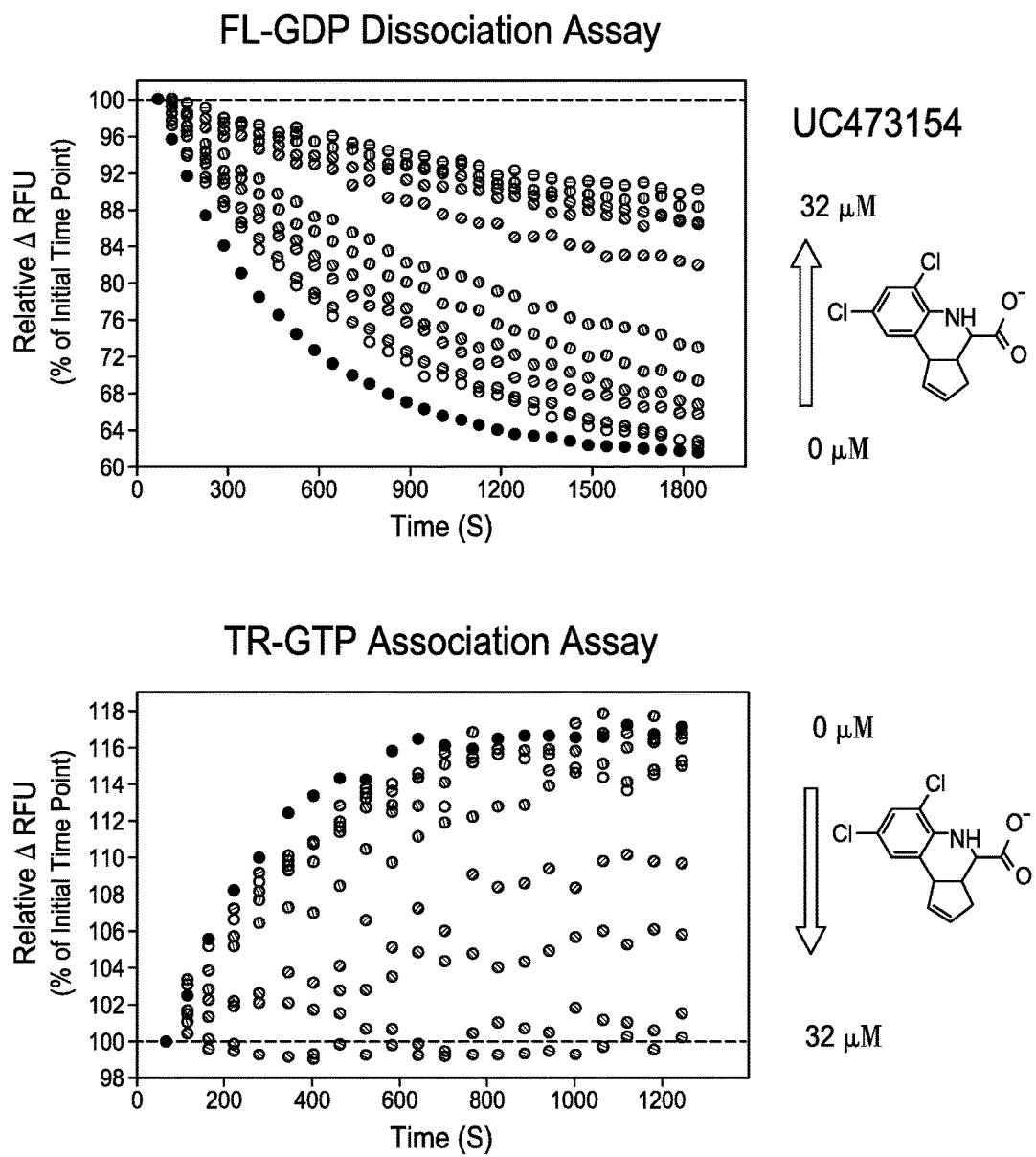
FIG. 7. Provides an example of dose-dependent inhibition using compound UC473154 showing relative GDP-dissociation and GTP-association of RhoA catalyzed by LARG.

The protocol shown in FIG. 6 was developed as follows. To establish an experimental screen for LARG-inhibitors, two complementary, fluorescence GTP-loading/GDP-dissociation assays are used to monitor in real time the LARG catalyzed RhoA guanine nucleotide exchange reaction in 384-well format. Additionally, FIG. 7 shows UC473154 dose-dependently inhibited LARG-catalyzed FL-GDP dissociation and TR-GTP binding to RhoA. Similar control assays using the RhoA-related Rac1 GEF reactions indicate the specificity of the compound.

The GTP-loading assay utilized the BODIPY-Texas Red (TR)-GTP nucleotide and measured an increase in red fluorescence over time, reflective of the GEF-mediated association of GTP with RhoA. In the GDP-dissociation assay, the BODIPY-Fluorescein(FL)-GDP nucleotide was used and decrease in green fluorescence was measured over time (FIG. 6), reflecting the GEF-mediated dissociation of GDP from RhoA.

Using first the FL-based GDP-dissociation assay, an experimental primary screen of the 1,912 candidate compounds was carried out at a dose of 32 M (Table 1). Results of the primary screen yielded 150 hits for a 7.8% hit rate using a 30% inhibition cutoff (Table 1). Next, a confirmation screen in triplicate was carried out at a dose of 32 M utilizing both the FL-GDP and TR-GTP based nucleotide exchange assays. 132 hit compounds were confirmed, for a hit rate of 6.9% that showed ≥30% inhibition in either or both assays (Table 1). Finally, a 10-dose serial two-fold dose response screen in triplicate (between 32 µM and 0.0625 µM) was carried out in both assays, as exemplified in FIG. 7. Using a cutoff of an IC50 of ≤16 µM for DH-PH and DH domain targeting compounds and ≤32 µM for PH domain targeting compounds, 33 candidate compounds for a final hit rate of 1.7% from 13 different structural chemical classes were identified (Table 1).

Based on the HTS results, lead compounds can be selected that rationally target the DH-PH, DH, or PH domain of LARG. Based on the dose-response results, a compound displayed dose-dependent inhibition of LARG-catalyzed GEF reaction in both fluorescence-based assays (FIG. 7). This HTS assay well suited for screening chemical libraries.

TABLE 1

Summary of a HTS of LARG experimental hits

| # of Compounds | Total Compounds Tested [UC-DDC Library] | Targeted Virtual Screen Hits [DH-PH Domain of LARG] | Primary Screen Hits [FL Assay] | Confirmation Screen Hits [FL and/or TR Assay] | Dose Response Hits [FL and TR Assay] |
| --- | --- | --- | --- | --- | --- |
| TOTAL | 350,000 | 1,912 | 150 (7.8% Hit Rate) | 132 (6.9% Hit Rate) | 33 (1.7% Hit Rate) |
| Target Domain: [DH-PH] | ... | 1,042 | 75 | 67 | 18 |
| Target Domain: [DH] | ... | 638 | 45 | 41 | 9 |
| Target Domain: [PH] | ... | 192 | 22 | 16 | 5 |
| Target Domain: [DH-PH, DH] | ... | 14 | 3 | 3 | 0 |
| Target Domain: [DH-PH, PH] | ... | 3 | 1 | 1 | 0 |
| Target Domain: [DH, PH] | ... | 22 | 3 | 3 | 1 |
| Target Domain: [DH-PH, DH, PH] | ... | 1 | 1 | 1 | 0 |

TABLE S2

Relative Inhibitory Activities of the Structural Analogs of Y16 on RhoA-LARG Interaction

| Compound # | Structure | Relative binding inhibition, % |
| --- | --- | --- |
| 1 | 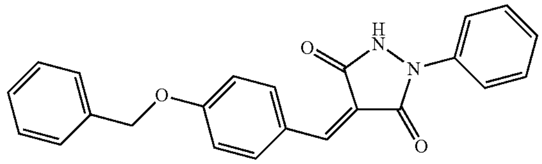 [SMILES: O=C1NN(c2ccccc2)C(=O)/C1=C/c1ccc(OCc2ccccc2)cc1] | 27.12 |
| 2 | 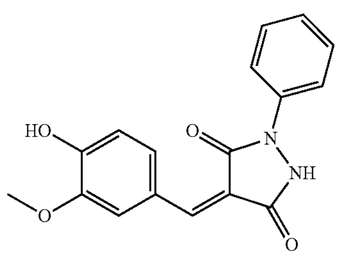 [SMILES: COc1cc(/C=C2/C(=O)NN(c3ccccc3)C2=O)ccc1O] | 12.97 |
| 3 | 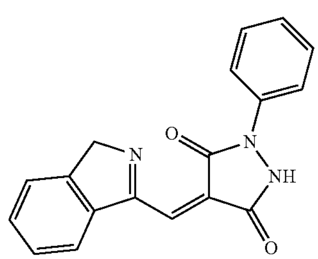 [SMILES: O=C1NN(c2ccccc2)C(=O)/C1=C\C1=NCc2ccccc21] | 6.75 |

TABLE S2-continued

Relative Inhibitory Activities of the Structural Analogs of Y16 on RhoA-LARG Interaction

| Compound # | Structure | Relative binding inhibition, % |
|---|---|---|
| 4 | 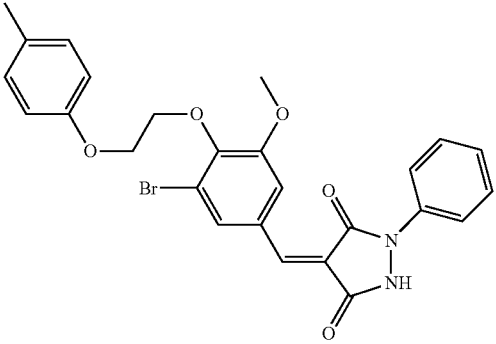 [SMILES: COc1cc(/C=C2/C(=O)NN(c3ccccc3)C2=O)cc(Br)c1OCCOc1ccc(C)cc1] | 13.77 |
| 5 | 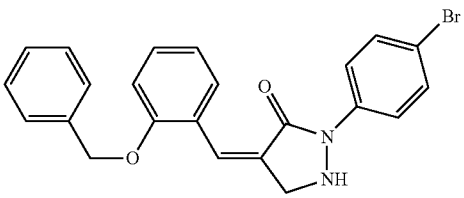 [SMILES: O=C1/C(=C\c2ccccc2OCc2ccccc2)CNN1c1ccc(Br)cc1] | 7.34 |

The inhibitory effects of the analogs were tested in a complex formation assay. (His)6-tagged LARG PH-DH (1 µg) was incubated with GST alone or GST-RhoA conjugated with glutathione agarose beads in the presence or absence of 100 µM indicated compounds. After an incubation at 4° C. for 1 h, the beads-associated (His)6-LARG PH-DH was detected by anti-His Western blotting. The relative inhibition of each analog was normalized to the inhibitory effect of Y16 of the same concentration.

REFERENCES

1. Etienne-Manneville S, Hall A (2002) Rho GTPases in cell biology. *Nature* 420(6916): 629-635.
2. Ridley A J (2001) Rho family proteins: Coordinating cell responses. *Trends Cell Biol* 11 (12):471-477.
3. Zohn I M, Campbell S L, Khosravi-Far R, Rossman K L, Der C J (1998) Rho family proteins and Ras transformation: The RHOad less traveled gets congested. *Oncogene* 17(11 Reviews):1415-1438.
4. Jaffe A B, Hall A (2005) Rho GTPases: Biochemistry and biology. *Annu Rev Cell Dev Biol* 21:247-269.
5. Rossman K L, Der C J, Sondek J (2005) GEF means go: Turning on RHO GTPases with guanine nucleotide-exchange factors. *Nat Rev Mol Cell Biol* 6(2): 167-180.
6. Vigil D, Cherfils J, Rossman K L, Der C J (2010) Ras superfamily GEFs and GAPs: Validated and tractable targets for cancer therapy? *Nat Rev Cancer* 10(12): 842-857.
7. Zheng Y (2001) Dbl family guanine nucleotide exchange factors. *Trends Biochem Sci* 26(12):724-732.
8. Hart M J, Eva A, Evans T, Aaronson S A, Cerione R A (1991) Catalysis of guanine nucleotide exchange on the CDC42Hs protein by the dbl oncogene product. *Nature* 354 (6351):311-314.
9. Cerione R A, Zheng Y (1996) The Dbl family of oncogenes. *Curr Opin Cell Biol* 8(2):216-222.
10. Hart M J, et al. (1994) Cellular transformation and guanine nucleotide exchange activity are catalyzed by a common domain on the dbl oncogene product. *J Biol Chem* 269(1):62-65.
11. Chikumi H, et al. (2004) Homo- and hetero-oligomerization of PDZ-RhoGEF, LARG and p115RhoGEF by their C-terminal region regulates their in vivo Rho GEF activity and transforming potential. *Oncogene* 23(1):233-240.
12. Hart M J, et al. (1998) Direct stimulation of the guanine nucleotide exchange activity of p115 RhoGEF by Galpha13. *Science* 280(5372):2112-2114.
13. Fukuhara S, Murga C, Zohar M, Igishi T, Gutkind J S (1999) A novel PDZ domain containing guanine nucleotide exchange factor links heterotrimeric G proteins to Rho. *J Biol Chem* 274(9):5868-5879.
14. Fukuhara S, Chikumi H, Gutkind J S (2001) RGS-containing RhoGEFs: The missing link between transforming G proteins and Rho? *Oncogene* 20(13):1661-1668.
15. Fukuhara S, Chikumi H, Gutkind J S (2000) Leukemia-associated Rho guanine nucleotide exchange factor (LARG) links heterotrimeric G proteins of the G(12) family to Rho. *FEBS Lett* 485(2-3):183-188.
16. Lappano R, Maggiolini M (2011) G protein-coupled receptors: Novel targets for drug discovery in cancer. *Nat Rev Drug Discov* 10(1):47-60.
17. Verdine G L, Walensky L D (2007) The challenge of drugging undruggable targets in cancer: Lessons learned from targeting BCL-2 family members. *Clin Cancer Res* 13(24): 7264-7270.
18. Hopkins A L, Groom C R (2002) The druggable genome. *Nat Rev Drug Discov* 1(9):727-730.
19. Hopkins A L, Groom C R (2003) Target analysis: A priori assessment of druggability. *Ernst Schering Res Found Workshop* 42(42): 11-17.

20. Russ A P, Lampel S (2005) The druggable genome: An update. *Drug Discov Today* 10 (23-24):1607-1610.
21. Kristelly R, Gao G, Tesmer J J (2004) Structural determinants of RhoA binding and nucleotide exchange in leukemia-associated Rho guanine-nucleotide exchange factor. *J Biol Chem* 279(45):47352-47362.
22. Irwin J J, Sterling T, Mysinger M M, Bolstad E S, Coleman R G (2012) ZINC: A free tool to discover chemistry for biology. *J Chem Inf Model* 2012 (June): 15.
23. Krieger E, Darden T, Nabuurs S B, Finkelstein A, Vriend G (2004) Making optimal use of empirical energy functions: Force-field parameterization in crystal space. *Proteins* 57 (4):678-683.
24. Duhr S, Braun D (2006) Why molecules move along a temperature gradient. *Proc Natl Acad Sci USA* 103(52): 19678-19682.
25. Dontu G, et al. (2003) In vitro propagation and transcriptional profiling of human mammary stem/progenitor cells. *Genes Dev* 17(10): 1253-1270.
26. Shang X, et al. (2012) Rational design of small molecule inhibitors targeting RhoA subfamily Rho GTPases. *Chem Biol* 19(6):699-710.
27. Hawkins P C, Skillman A G, Warren G L, Ellingson B A, Stahl M T (2010) Conformer generation with OMEGA: Algorithm and validation using high quality structures from the Protein Databank and Cambridge Structural Database. *J Chem Inf Model* 50(4): 572-584.
28. Wienken C J, Baaske P, Rothbauer U, Braun D, Duhr S (2010) Protein-binding assays in biological liquids using microscale thermophoresis. *Nat Commun* 1:100.
29. Gao Y, Dickerson J B, Guo F, Zheng J, Zheng Y (2004) Rational design and characterization of a Rac GTPase-specific small molecule inhibitor. *Proc Natl Acad Sci USA* 101 (20):7618-7623.

What is claimed is:

1. A method of inhibiting Rho GTPase activation comprising contacting a RhoGEF with a compound having the structure of Formula Ia:

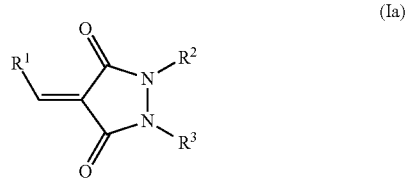

(Ia)

or a pharmaceutically acceptable salt thereof, wherein:

$R^1$ is

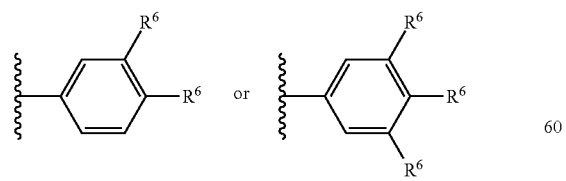

or 1H-isoindolyl;

each $R^6$ is independently selected from the group consisting of hydroxy, fluoro, chloro, $C_{1-3}$ alkyl, $C_{1-3}$ alkoxy, and $C_{1-4}$ alkoxy substituted with $R^{1B}$;

each $R^{1B}$ is independently selected from the group consisting of —$OR^{1C}$, aryl, and heteroaryl, said aryl or heteroaryl each optionally substituted with one or more $R^{1D}$;

each $R^{1C}$ is independently selected from the group consisting of aryl, and heteroaryl, said aryl or heteroaryl each optionally substituted with one or more $R^{1E}$;

each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is phenyl; and $R^3$ is H (hydrogen).

2. The method of claim 1, wherein a therapeutically effective amount of the compound having the structure of Formula I is administered to a subject in need of treatment for breast cancer, leukemia or lung cancer.

3. The method of claim 2, where the a compound having the structure of Formula I has the structure:

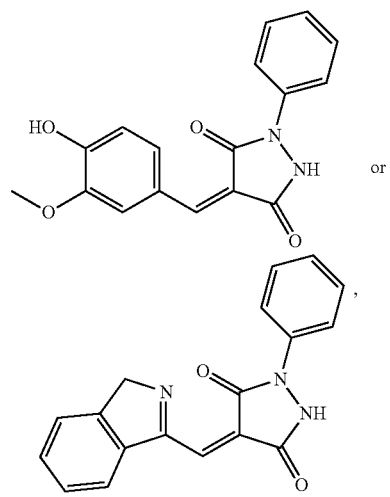

or a pharmaceutically acceptable salt thereof.

4. A method of inhibiting Rho GTPase activation comprising contacting a RhoGEF with a compound having the structure of Formula I:

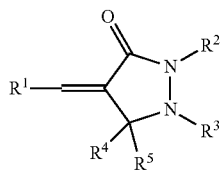

or a pharmaceutically acceptable salt thereof,
wherein:
R¹ is

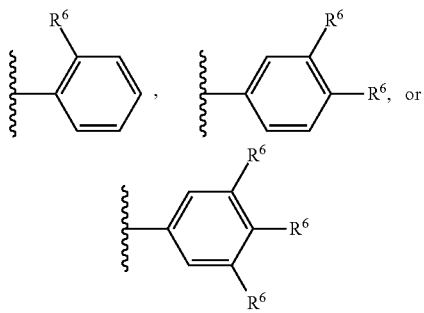

or 1H-isoindolyl;
  each R⁶ is independently selected from the group consisting of fluoro, chloro, methyl, ethoxy, and $C_{1-3}$ alkoxy substituted with $R^{1B}$;
  each $R^{1B}$ is independently selected from the group consisting of —$OR^{1C}$, aryl, and heteroaryl, said aryl or heteroaryl each optionally substituted with one or more $R^{1D}$;
  each $R^{1C}$ is independently selected from the group consisting of aryl, and heteroaryl, said aryl or heteroaryl each optionally substituted with one or more $R^{1E}$;
  each $R^{1D}$ is independently selected from the group consisting of hydroxy, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, and $C_{1-6}$ alkoxy optionally substituted with up to 5 fluoro;
  each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;
R² is H (hydrogen), aryl, or heteroaryl, said aryl or heteroaryl each optionally substituted with one or more $R^{2A}$;
  each $R^{2A}$ is independently selected from the group consisting of hydroxy, halo, cyano, optionally substituted $C_{3-7}$ cycloalkyl, optionally substituted aryl, optionally substituted heteroaryl, optionally substituted heterocyclyl, $C_{1-6}$ alkyl substituted with up to 5 fluoro, and $C_{1-6}$ alkoxy optionally substituted with up to 5 fluoro; and
R³ is H (hydrogen), aryl, or heteroaryl, said aryl or heteroaryl each optionally substituted with one or more $R^{3A}$, provided that one of R² and R³ is H (hydrogen) and one of R² and R³ is not H (hydrogen);
  each $R^{3A}$ is independently selected from the group consisting of hydroxy, halo, cyano, optionally substituted $C_{3-7}$ cycloalkyl, optionally substituted aryl, optionally substituted heteroaryl, optionally substituted heterocyclyl, $C_{1-6}$ alkyl substituted with up to 5 fluoro, and $C_{1-6}$ alkoxy optionally substituted with up to 5 fluoro;
R⁴ is H (hydrogen), or $C_{1-6}$ alkyl; and
R⁵ is H (hydrogen), or $C_{1-6}$ alkyl, or optionally R⁴ and R⁵ together are oxo.

5. The method of claim 4, wherein R³ is H (hydrogen).

6. The method of claim 5, wherein R² is phenyl optionally substituted with one or more $R^{2A}$; and each $R^{2A}$ is independently selected from the group consisting of halo, $C_{1-6}$ alkyl substituted with up to 5 fluoro, and $C_{1-6}$ alkoxy optionally substituted with up to 5 fluoro.

7. The method of claim 6, wherein R² is

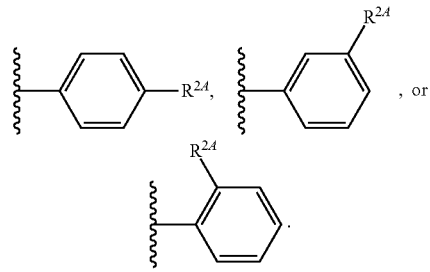

8. The method of claim 7, wherein $R^{2A}$ is fluoro, chloro, bromo, methoxy, ethoxy, trifluoromethyl, or trifluoromethoxy.

9. The method of claim 4, wherein R³ is phenyl optionally substituted with one or more $R^{3A}$; and each $R^{3A}$ is independently selected from the group consisting of halo, $C_{1-6}$ alkyl substituted with up to 5 fluoro, and $C_{1-6}$ alkoxy optionally substituted with up to 5 fluoro.

10. The method of claim 9, wherein R³ is

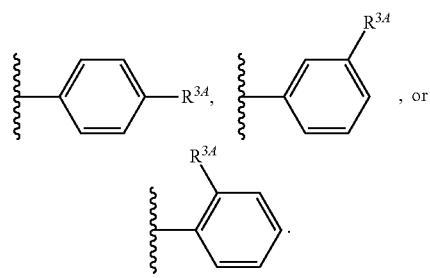

11. The method of claim 10, wherein $R^{3A}$ is fluoro, chloro, bromo, methoxy, ethoxy, trifluoromethyl, or trifluoromethoxy.

12. The method of claim 4, where the a compound having the structure of Formula I has the structure:

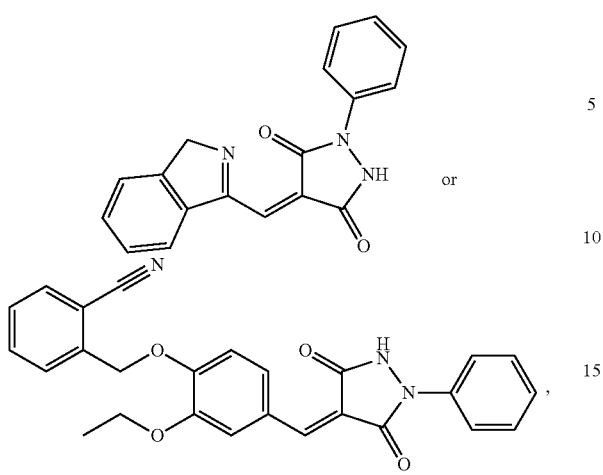

or a pharmaceutically acceptable salt thereof.

13. A method of inhibiting Rho GTPase activation comprising contacting a RhoGEF with a compound having the structure of Formula Ia:

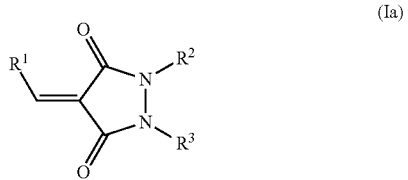

(Ia)

or a pharmaceutically acceptable salt thereof, wherein:
$R^1$ is

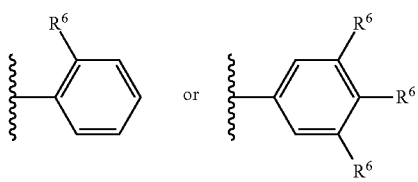

or 1H-isoindolyl;
each $R^6$ is independently selected from the group consisting of fluoro, chloro, bromo, methyl, methoxy, and $C_{1-4}$ alkoxy substituted with $R^{1B}$;
each $R^{1B}$ is independently selected from the group consisting of —$OR^{1C}$, aryl, and heteroaryl, said aryl or heteroaryl each optionally substituted with one or more $R^{1D}$;
each $R^{1C}$ is independently selected from the group consisting of aryl, and heteroaryl, said aryl or heteroaryl each optionally substituted with one or more $R^{1E}$;
each $R^{1D}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

each $R^{1E}$ is independently selected from the group consisting of hydroxy, halo, cyano, nitro, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, amino, optionally substituted $C_{3-7}$ cycloalkyl, optionally substituted aryl, optionally substituted heteroaryl, optionally substituted heterocyclyl, $C_{1-6}$ alkyl optionally substituted with up to 5 fluoro, and $C_{1-6}$ alkoxy optionally substituted with up to 5 fluoro;

$R^2$ is aryl optionally substituted with one or more $R^{2A}$;
each $R^{2A}$ is independently selected from the group consisting of hydroxy, bromo, cyano, optionally substituted $C_{3-7}$ cycloalkyl, optionally substituted aryl, optionally substituted heteroaryl, optionally substituted heterocyclyl, $C_{1-6}$ alkyl substituted with up to 5 fluoro, and $C_{1-6}$ alkoxy optionally substituted with up to 5 fluoro; and $R^3$ is H (hydrogen);
each $R^{3A}$ is independently selected from the group consisting of hydroxy, bromo, cyano, optionally substituted $C_{3-7}$ cycloalkyl, optionally substituted aryl, optionally substituted heteroaryl, optionally substituted heterocyclyl, $C_{1-6}$ alkyl substituted with up to 5 fluoro, and $C_{1-6}$ alkoxy optionally substituted with up to 5 fluoro;

$R^4$ is H (hydrogen), or $C_{1-6}$ alkyl; and
$R^5$ is H (hydrogen), or $C_{1-6}$ alkyl, or optionally $R^4$ and $R^5$ together are oxo.

14. The method of claim 13, wherein $R^3$ is H (hydrogen).

15. The method of claim 14, wherein $R^2$ is phenyl optionally substituted with one or more $R^{2A}$; and each $R^{2A}$ is independently selected from the group consisting of halo, $C_{1-6}$ alkyl substituted with up to 5 fluoro, and $C_{1-6}$ alkoxy optionally substituted with up to 5 fluoro.

16. The method of claim 15, wherein $R^2$ is

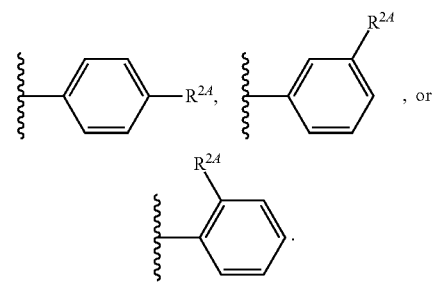

17. The method of claim 16, wherein $R^{2A}$ is fluoro, chloro, bromo, methoxy, ethoxy, trifluoromethyl, or trifluoromethoxy.

18. The method of claim 13, where the a compound having the structure of Formula I has the structure:

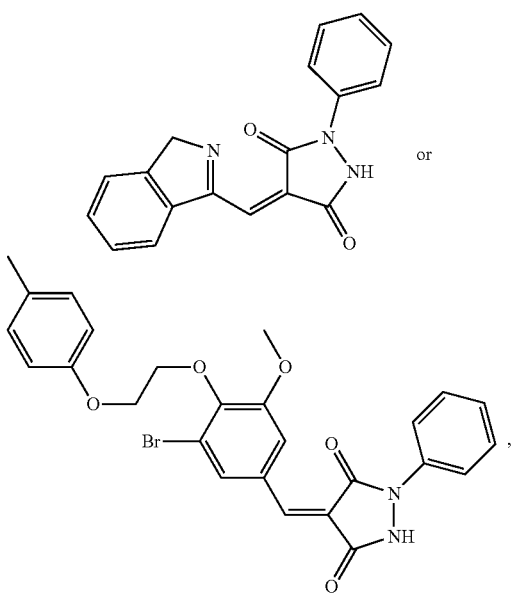
or a pharmaceutically acceptable salt thereof.
19. A method of inhibiting Rho GTPase activation comprising contacting a RhoGEF with a compound having the structure
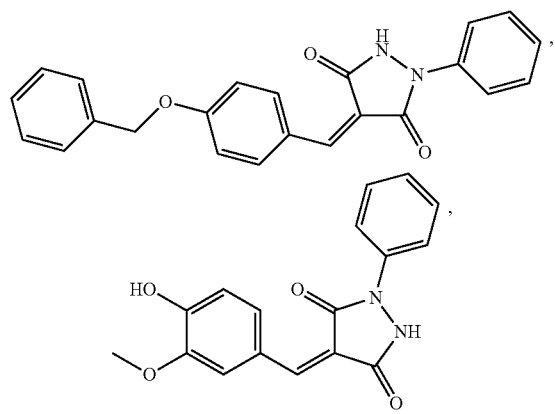
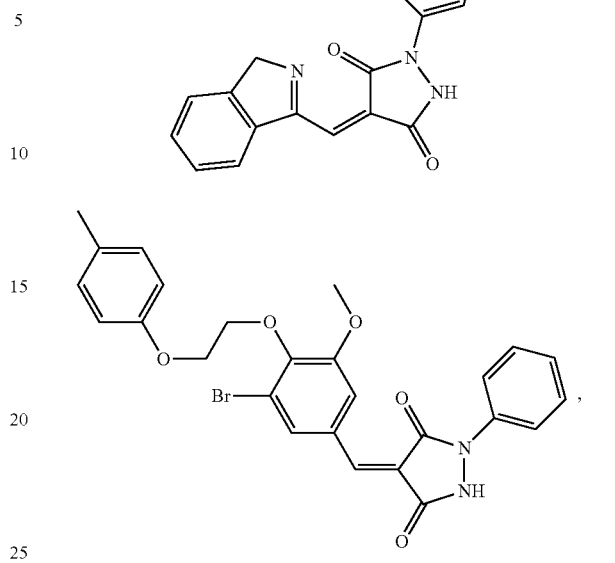
or a pharmaceutically acceptable salt thereof.
* * * * *